(12) United States Patent
Hill

(10) Patent No.: US 6,330,065 B1
(45) Date of Patent: *Dec. 11, 2001

(54) GAS INSENSITIVE INTERFEROMETRIC APPARATUS AND METHODS

(75) Inventor: Henry Allen Hill, Tucson, AZ (US)

(73) Assignee: Zygo Corporation, Middlefield, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/301,475

(22) Filed: Apr. 28, 1999

Related U.S. Application Data

(63) Continuation-in-part of application No. 09/232,515, filed on Jan. 16, 1999, which is a continuation-in-part of application No. 09/176,442, filed on Oct. 21, 1998, which is a continuation-in-part of application No. 08/942,848, filed on Oct. 2, 1997.
(60) Provisional application No. 60/075,595, filed on Feb. 23, 1998.

(51) Int. Cl.$^7$ .................................... G01B 9/02
(52) U.S. Cl. .................. 356/485; 356/511; 356/517
(58) Field of Search ................... 356/450, 484, 356/517, 491, 485, 486, 487, 498, 496

(56) References Cited

U.S. PATENT DOCUMENTS

| | | |
|---|---|---|
| 3,647,302 | 3/1972 | Zipin et al. . |
| 4,215,938 | 8/1980 | Farrand et al. . |
| 4,685,803 | 8/1987 | Sommargren . |
| 4,733,967 | 3/1988 | Sommargren . |
| 4,813,783 | 3/1989 | Torge . |
| 4,948,254 | 8/1990 | Ishida . |
| 5,218,426 | 6/1993 | Hall et al. . |
| 5,404,222 | 4/1995 | Lis . |
| 5,483,343 | 1/1996 | Iwamato et al. . |
| 5,537,209 | 7/1996 | Lis . |
| 5,663,793 | 9/1997 | de Groot . |

FOREIGN PATENT DOCUMENTS

| | | |
|---|---|---|
| 0 094 836 A | 11/1983 | (EP) . |
| WO 91/03729 A | 3/1991 | (WO) . |

OTHER PUBLICATIONS

Erikson, Kent E., Long–Path Interferometry through an Uncontrolled Atmosphere, Journal of the Optical Society of America, vol. 52, No. 7 (Jul. 1962), pp. 781–787.

Bender, Peter L. and Owens, James C., Correction Of Optical Distance Measurements for the Fluctuating Atmospheric Index of Refraction, Journal of Geophysical Research, vol. 70, No. 10 (May 15, 1965), pp. 2461–2462.

Edlen, Bengt, The Refractive Index of Air, *Metrologia*, vol. 2, No. 2 (1966). pp. 71–80.

Earnshaw, K. B. and Hernandez, E. Norman, Two–Laser Optical Distance–Measuring Instrument That Corrects For The Atmospheric Index Of Refraction, Applied Optics, vol. 11, No. 4 (Apr. 1972), pp. 749–754.

(List continued on next page.)

*Primary Examiner*—Robert H. Kim
*Assistant Examiner*—Andrew H. Lee
(74) *Attorney, Agent, or Firm*—Francis J. Caufield

(57) ABSTRACT

Displacement measuring interferometers (DMI) are disclosed for use in conjunction with apparatus for measuring and monitoring the intrinsic optical properties of the gas in the measurement leg of a DMI to compensate for variations in the refractive index of the gas that would otherwise render subsequent displacement calculations less accurate. The DMIs may be used for either linear or angular displacements. Cyclic error compensation, wavelength monitoring and correction, and phase redundancy features are included to further enhance the accuracy with which displacement determinations may be made and are particularly suitable for use in photolithographic applications.

97 Claims, 17 Drawing Sheets

OTHER PUBLICATIONS

Hernandez, E. N. and Earhshaw, K. B., Field Tests of a Two–Laser (4416A And 6328A) Optical Distance–Measuring Instrument Correcting for the Atmospheric Index of Refraction, Journal of Geophysical Research, vol. 77, No. 35, (Dec. 10, 1972), pp. 6994–6998.

Slater, L. E. and Huggett, G. R., A Multiwavelength Distance–Measuring Instrument for Geophysical Experiments, Journal of Geophysical Research, vol. 81, No. 35 (Dec. 10, 1976), pp. 6299–6306.

Berg, Eduard and Carter, Jerry A., Distance Corrections for Single– and Dual–Color Lasers by Ray Tracing, Journal of Geophysical Research, vol. 85, No. B11, (Nov. 10, 1980), pp. 6513–6520.

Jones, Frank E., The Refractivity of Air, Jorunal of Research of the National Bureau of STandards, vol. 86, No. 1, (Jan.–Feb. 1981), pp 27–32.

Matsumoto, Hirokazu and Tsukahara, Koichi, Effects of the atmospheric phase fluctuation on long–distance measurement, Applied Optics, vol. 23, No. 19, (Oct. 1, 1984), pp 3388–3394.

Gibson, G. N.; Heyman, J., Lugten, J., Fitelson, W., and Townes, C. H., Optical path length fluctuations in the atmosphere, App. Optics, vol. 23, No. 23, (Dec. 1, 1984), pp 4383–4389.

Estler, W. Tyler, High–accuracy displacement interferometry in air, Applied Optics, vol. 24, (Mar. 15, 1985), pp. 808–815.

Bobroff, Norman, Residual errors in laser interferometry form air turbulence and nonlinearity, Applied Optics, vol. 26, No. 13, (Jul. 1, 1987), pp. 2676–2682.

Ishida, Akira, Two–Wavelength Displacement–Measuring Interferometer Using Second–Harmonic Light to Eliminate Air–Turbulence–Induced Errors, Japanese Journal of Applied Physics, vol. 28(3), (Mar. 1989), pp. L473–L475.

Birch, K. P. and Downs, M. J., Error sources in the determination of the refractive index of air, Applied Optics, vol. 28, No. 5, (Mar. 1, 1989), pp. 825–826.

Howe, Uwe and Kerl, Klaus, Interferometric measurements of the dipole polarizability [alpha] of molecules between 300K and 1100K, Molercular Physics, vol. 69 (1990), pp. 803–817.

Zhu, Yucong; Matsumoto, Hirokazu; and O'ishi, Tadanao, Long–arm two–color interferometer for measuring the change of air refractive index, SPIE, vol. 1319, Optics in Complex Systems (1990), pp 538–539.

Achtermann, H. J. and Magnus, G., Refractivity virial coefficients of gaseous $CH_4$, $C_2H_4$, $C_2H_6$, $CO_2$, $SF_6$, $H_2$, $N_2$, He, and Ar, J. Chem, Phys., 94(8), (Apr. 15, 1991), pp. 5669–5684.

Beers, J. and Doiron, T., Verification of Revised Water Vapour Correction to the Index of Refraction of Air, Metrologia, 29 (1992), pp. 315–316.

Bobroff, Norman, Recent advances in displacement measuring interferometry, Measurement Science and Technology, vol. 4, No. 9 (Sep. 1993), pp. 907–926.

Lis, Steven A., An Air Turbulence Compensated Interferometer For IC Manufacturing, SPIE, Conf. 2440 (Feb. 24, 1995).

GAS INSENSITIVE INTERFEROMETRIC APPARATUS AND METHODS

CROSS REFERENCE TO RELATED APPLICATIONS

This application is a continuation-in-part of commonly owned U.S. patent application Ser. No. 09/232, 515 entitled APPARATUS AND METHODS FOR MEASURING INTRINSIC OPTICAL PROPERTIES OF A GAS filed on Jan. 16, 1999 which, in turn, is a continuation-in-part of commonly owned U.S. patent application Ser. No. 09/176, 442 entitled "INTERFEROMETRIC METHOD AND APPARATUS FOR MEASURING INTRINSIC OPTICAL PROPERTIES OF A GAS" and filed on Oct. 21, 1998 which, in turn, is a continuation-in-part U.S. Patent Application Ser. No. 08/942,848 filed on Oct. 2, 1997 in the name of Henry Allen Hill for "APPARATUS AND METHODS FOR MEASURING INTRINSIC OPTICAL PROPERTIES OF A GAS" and also claims priority from U.S. Provisional Patent Application No. 60/075,595 entitled "APPARATUS AND METHODS FOR MEASURING INTRINSIC OPTICAL PROPERTIES OF A GAS" filed on Feb. 23, 1998.

BACKGROUND OF THE INVENTION

The present invention relates, in general, to optical metrology, and, in particular, to interferometric displacement measurement independent of the optical path length effects of the refractive index of a gas in a measurement path, including the effects of refractive index fluctuations.

A frequently encountered problem in precision interferometric metrology is the need to have accurate knowledge about the refractive index of a gas in a measurement path and/or the change in optical path length of the measurement path due to the gas. This is especially true where the refractive index of the gas may be fluctuating, e.g. the gas is turbulent, and/or the physical length of the measuring path may be changing. With accurate information about the index and its effects on changes in the optical path, it is possible to correct for errors caused by such effects in the determination of physical displacements in length and angle.

Several techniques exist for measuring the index under highly controlled circumstances, such as when an air column is contained in a sample cell and is monitored for temperature, pressure, and physical dimension. However, measuring index under uncontrolled conditions is technically challenging, particularly where high accuracies are required. Perhaps the most difficult measurement related to the refractive index of air is the measurement of refractive index fluctuations over a measurement path of unknown or variable length, with uncontrolled temperature and pressure. Such circumstances arise frequently in high-precision distance measuring interferometry, such as is employed in micro-lithographic fabrication of integrated circuits. See for example an article entitled "Residual errors in laser interferometry from air turbulence and non-linearity," by N. Bobroff, *Appl. Opt.* 26(13), 2676–2682 (1987), and an article entitled "Recent advances in displacement measuring interferometry," also by N. Bobroff, *Measurement Science & Tech.* 4 (9), 907–926 (1993).

As is known, interferometric displacement measurements in air are subject to environmental uncertainties, particularly to changes in air pressure and temperature; to uncertainties in air composition such as resulting from changes in humidity; and to the effects of turbulence in the air. Such factors alter the wavelength of the light used to measure the displacement.

Under normal conditions, the refractive index of air is approximately 1.0003 with a variation of the order of $1\times10^{-5}$ to $1\times10^{-4}$. However, in many applications the refractive index of air must be known with a relative precision of less than 0.1 ppm (parts per million) to 0.003 ppm, these two relative precisions corresponding to a displacement measurement accuracy of 100 nm and 3 nm, respectively, for a one meter interferometric displacement measurement.

One way to detect refractive index fluctuations is to measure changes in pressure and temperature along a measurement path and calculate the effect on the optical path length of the measurement path. Mathematical equations for effecting this calculation are disclosed in an article entitled "The Refractivity Of Air," by F. E. Jones, *J. Res. NBS* 86(1), 27–32 (1981). An implementation of the technique is described in an article entitled "High-Accuracy Displacement Interferometry In Air," by W. T. Estler, *Appl. Opt.* 24(6), 808–815 (1985). Unfortunately, this technique provides only approximate values, is cumbersome, and corrects only for slow, global fluctuations in air density.

Another, more direct way to detect the effects of a fluctuating refractive index over a measurement path is by multiple-wavelength distance measurement. The basic principle may be understood as follows. Interferometers and laser radar measure the optical path length between a reference and an object, most often in open air. The optical path length is the integrated product of the refractive index and the physical path traversed by a measurement beam. In that the refractive index varies with wavelength, but the physical path is independent of wavelength, it is generally possible to determine the physical path length from the optical path length, particularly the contributions of fluctuations in refractive index, provided that the instrument employs at least two wavelengths and the intrinsic optical properties of the gas are knowable. Since the variation of refractive index with wavelength is known in the art as dispersion, this technique is often referred to as the dispersion technique.

The dispersion technique for refractive index measurement has a long history in optical interference phase detection for shorter distances. In U.S. Pat. No. 3,647,302 issued in 1972 to R. B. Zipin and J. T. Zalusky, entitled "Apparatus For And Method Of Obtaining Precision Dimensional Measurements," there is disclosed an interferometric displacement-measuring system employing multiple wavelengths to compensate for variations in ambient conditions such as temperature, pressure, and humidity. The instrument is specifically designed for operation with a movable object, that is, with a variable physical path length. However, the phase-detection means of Zipin and Zalusky appears to be insufficiently accurate for high-precision measurement.

A recent attempt at high-precision interferometry for micro-lithography is represented by U.S. Pat. No. 4,948,254 issued to A. Ishida (1990). A similar device is described by Ishida in an article entitled "Two Wavelength Displacement-Measuring Interferometer Using Second-Harmonic Light To Eliminate Air-Turbulence-Induced Errors," *Jpn. J. Appl. Phys.* 28(3), L473–475 (1989). In the article, a displacement-measuring interferometer is disclosed which eliminates errors caused by fluctuations in the refractive index by means of two-wavelength dispersion detection.

In U.S. Pat. No. 5,404,222 entitled "Interferometric Measuring System With Air Turbulence Compensation," issued to S. A. Lis (1995), there is disclosed a two-wavelength interferometer employing the dispersion technique for detecting and compensating refractive index fluctuations. A similar device is described by Lis in an article entitled "An Air Turbulence Compensated Interferometer For IC Manufacturing," *SPIE* 2440 (1995). However, both Ishida and Lis rely on externally supplied data about the value of the reciprocal dispersive power of the gas occupying the measurement path.

It is clear from the foregoing, that the prior art does not provide a practical, high-speed, high-precision method and corresponding means for measuring refractive index of air and measuring and compensating for the optical path length effects of the air in a measuring path, particularly the effects due to fluctuations in the refractive index of the air. The limitations in the prior art arise principally from the following, unresolved technical difficulties: (1) Prior-art heterodyne and superheterodyne interferometers are limited in accuracy by fluctuations in the refractive index of air; (2) Prior-art dispersion techniques for measuring index fluctuations require extremely high accuracy in interference phase measurement, typically exceeding by an order of magnitude the typical accuracy of high-precision distance-measuring interferometers; (3) Obvious modifications to prior-art interferometers to improve phase-measuring accuracy would increase the measurement time to an extent incompatible with the rapidity of stage motion in modern micro-lithography equipment; (4) Prior-art dispersion techniques require at least two extremely stable laser sources, or a single source emitting multiple, phase-locked wavelengths; (5) Prior-art dispersion techniques in micro-lithography applications are sensitive to stage motion during the measurement, resulting in systematic errors; and (6) Prior-art dispersion techniques that employ doubling crystals (e.g. U.S. Pat. No. 5,404,222 to Lis) as part of the detection system are expensive and complicated.

These deficiencies in the prior art have led to the absence of any practical interferometric system for performing displacement measurement for micro-lithography in the presence of a gas in a measurement path where there are typically refractive index fluctuations and the measurement path is comprised of a changing physical length.

Accordingly, it is an object of the invention to provide a displacement measuring interferometric system by which the refractive index of a gas in a measurement path and/or the optical path length effects of the gas are rapidly and accurately measured and monitored wherein the refractive index may be fluctuating and/or the physical length of the measurement path may be changing.

It is another object of the invention to provide a displacement measuring interferometric system and method by which the refractive index of a gas in a measurement path and/or the optical path length effects of the gas are rapidly and accurately measured and monitored wherein the accuracy of measurements and monitoring of the refractive index of the gas and/or of the optical path length effects of the gas are substantially not compromised by a rapid change in physical length of measurement path.

It is another object of the invention to provide a displacement interferometric system and method by which the refractive index of a gas in a measurement path and/or the optical path length effects of the gas are rapidly and accurately measured and monitored wherein the system and method does not require measurement and monitoring of environmental conditions such as temperature and pressure.

It is another object of the invention to provide a displacement measuring interferometric system and method by which the refractive index of a gas in a measurement path and/or the optical path length effects of the gas are rapidly and accurately measured and monitored wherein the system and may, but does not require, use of two or more optical beams of differing wavelengths which are phase locked.

It is another object of the invention to provide displacement measuring interferometric systems and methods by which the refractive index of a gas in the measurement path and/or the optical path length effects of the gas are rapidly and accurately measured, monitored and used to accurately determine physical displacement by compensating for refractive index effects in the measurement path.

It is another object of the invention to provide displacement measuring interferometric systems and methods by which changes in the refractive index of a gas in the measurement path and/or the optical path length effects of the gas are accurately measured, monitored and used to accurately determine physical displacement by compensating for refractive index effects in the measurement path.

Other objects of the invention will, in part, be obvious and will, in part, appear hereinafter. The invention accordingly comprises methods and apparatus possessing the construction, steps, combination of elements, and arrangement of parts exemplified in the detailed description to follow when read in connection with the drawings.

SUMMARY OF THE INVENTION

The present invention generally relates to interferometric apparatus and methods for precisely measuring displacement (linear and/or angular) in at least one measurement path while contemporaneously measuring and monitoring the refractive index of a gas in the measurement path and/or the change in optical path length of the measurement path due to the gas to obtain information about the impact that such refractive effects have on the accuracy of displacement determinations and compensate for those effects. The refractive index of the gas in the measurement path may be fluctuating, e.g. the gas is turbulent, and/or the physical length of the measuring path may be changing. The present invention also relates to apparatus and methods for use in electro-optical metrology and other applications. More specifically, the invention operates to provide measurements of dispersion of the refractive index, the dispersion being substantially proportional to the density of the gas, and/or measurements of dispersion of the optical path length, the dispersion of the optical path length being related to the dispersion of the refractive index and the physical length of the measurement path. The refractive index of the gas and/or the optical path length effects of the gas are subsequently computed from the measured dispersion of the refractive index and/or the measured dispersion of the optical path length, respectively. The information generated by the inventive apparatus is particularly suitable for use in interferometric distance measuring instruments (DMI) to compensate for errors related to refractive index of gas in at least one measurement path brought about by environmental effects and turbulence induced by rapid stage slew rates.

Several embodiments of the invention have been made having different interferometric architectures for the generation of extrinsic displacement signals containing information about the optical path length of the measurement path and signals containing information about the intrinsic properties of the gas that is used to compensate for errors in displacement calculations that would otherwise be present absent knowledge about the intrinsic optical properties of the gas.

Other features of inventive embodiments relate to various means by which light beams of different wavelengths can be generated and monitored, the relationship of the values of those wavelengths, methods and apparatus for compensating for phase redundancy, cyclic errors, Doppler shift effects due to stage motion, and/or shear effects. In addition, different approaches to signal processing are described, including the use of direct phase measurement and homodyne, heterodyne, and superheterodyne techniques.

BRIEF DESCRIPTION OF THE DRAWINGS

The structure and operation of the invention, together with other objects and advantages thereof, may best be understood by reading the detailed description in conjunction with the drawings wherein the invention's parts have an assigned reference numeral that is used to identify them in all of the drawings in which they appear and wherein:

FIG. 1b shows a more detailed representation of the electronic processor of FIG. 1a;

FIG. 2b is a more detailed diagrammatic representation of the electronic processor of FIG. 2a;

FIG. 3f depicts in more detail the electronic processor of FIG. 3a;

FIGS. 5a–5c relate to lithography and its application to manufacturing integrated circuits wherein FIG. 5a is a schematic drawing of a lithography exposure system employing the interferometry system, and FIGS. 5b and 5c are flow charts describing steps in manufacturing integrated circuits.

DETAILED DESCRIPTION OF THE INVENTION

The present invention relates to interferometric apparatus and methods by which the effect of changes in the refractive index of a gas in the measurement path of an interferometer can be compensated for in making accurate displacement determinations for measurements taken during a period during which the index may be changing simultaneously with changes in the physical length of the measurement path. The refractive index changes that are compensated may be due to changes in the composition of the gas and/or fluctuations in the gas due to rapid changes in the measurement leg such as those that occur in lithographic processes for fabricating semiconductor circuits.

Figure 1:
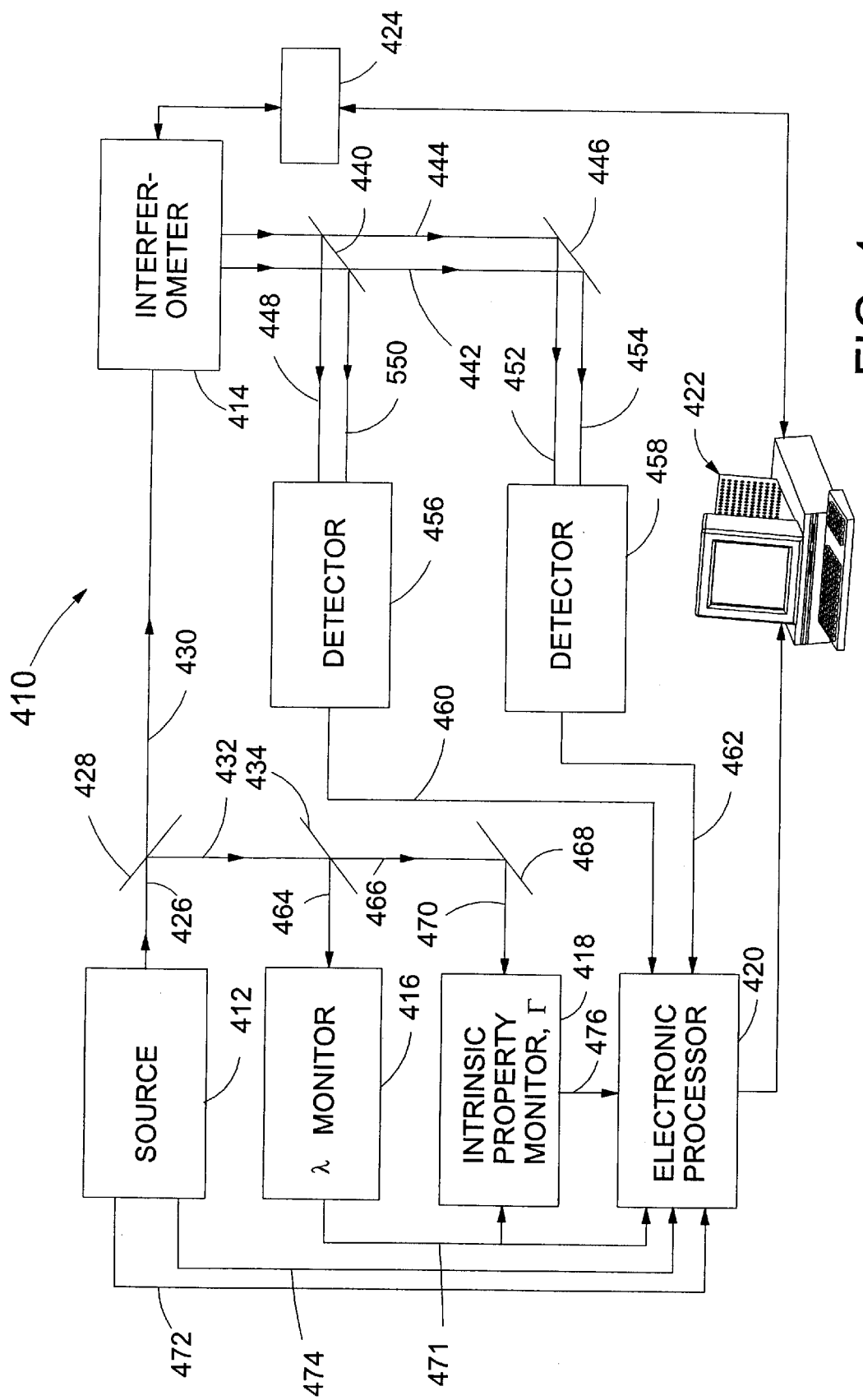
FIG. 1 is a diagrammatic, high level chart showing the major elements of apparatus of the invention, their functions and relationships to one another, and various kinds of information which they generate and process to make precision displacement measurements for use in a variety of downstream applications.

Reference is now made to FIG. 1 which diagrammatically shows the major elements of a generalized apparatus 410 of the invention. The major elements of apparatus 410 are seen to comprise a source 412 for generating beams of radiation of different wavelengths, a dispersion interferometer 414 that may assume a variety of architectures, a wavelength monitor 416 for measuring the accuracy of the wavelengths of various beams generated by source 412, an instrument 418 that operates to measure and monitor intrinsic optical properties of the gas in the measurement leg of the dispersion interferometer 412, an electronic processor 420 for receiving and operating on various electrical signals generated elsewhere in apparatus 410, a computer 422 or equivalent microprocessor that is supplied with software programs for performing control, housekeeping, and computational functions as will become apparent hereinafter, and a block 424 representing various downstream applications that beneficially use the upstream results generated by the other elements of apparatus 410. For example, block 424 may be any sensible application requiring accurate displacement information and preferably is part of equipment of the type to be subsequently described for use in lithographic processes for manufacturing semiconductor devices In such applications, the lithographic equipment may be linked to interferometer 414 and computer 422 in well-known manners.

Source 412 generates at least two light beams 426 of different wavelengths to provide reference and measurement beams for use in interferometer 414. Beams 426, depending on the details of the means of generation, may be polarized and coextensive, polarized and spatially separated, spatially separated, harmonically related, result from second harmonic generation, frequency shifted, originate from one or more lasers or other appropriate means for the generation of sources that are preferably coherent.

After emerging from source 412, beams 426 are intercepted by a beamsplitter 428 that transmits a portion of them to interferometer 414 as beams 430 and reflects a portion as beams 432 for travel to a beamsplitter 434.

Interferometer 414 may be any well-known type of amplitude splitting dispersion interferometer such as a Michelson, modified Michelson, plane mirror, differential plane mirror interferometer, Mach-Zehnder, angle compensating, or other type readily known to those skilled in the art.

Interferometer 414 is provided with means not shown in FIG. 1 for dividing beams 430 into reference and measurement beams for travel along reference and measurements legs (also not shown here) of interferometer 414. The measurement leg is variable and is at least in part occupied by a gas. It may be coupled with, for example, a stage that forms part of a lithographic process whose displacement must be accurately determined. While commonly of fixed length, the reference leg need not be fixed but may also vary and may also be in part occupied by the gas.

After traveling along the reference and measurement legs of interferometer 414, interferometer 414 generates output reference beam 436 and output measurement beam 438 at both wavelengths. Beams 436 and 438 are intercepted by a beamsplitter 440 which separates on the basis of wavelength for travel as beams 48 and 450 at one wavelength to a detector 456 and beams 442 and 444 at another wavelength to a detector 458. Detector 456 operates to convert the input optical beams 48 and 450 to an electrical signal 460 that is sent to electronic processor 420, and detector 458 likewise operates to convert optical signals 452 and 454 to an electrical signal 462 that is passed along to electronic processor 420

Electrical signals 460 and 462 non-intrinsic phase information about the differences in optical path length experienced by reference and measurement beams at both wavelengths as they traveled through interferometer 414. The non-intrinsic phase information, such as index of refraction and refractivity which depends on the column density of the gas, as is well-known, is insufficient to accurately calculate displacement, linear and/or angular, using a dispersion interferometer. The invention, however, by way of intrinsic property monitor 418 and/or wavelength monitor 416 is able to compensate for the deficiencies in the non-intrinsic information provided by interferometer 414.

More particularly, and as subsequently pointed out in connection the description of the various detailed embodiments to follow, intrinsic property monitor 418 provides information about the relative refractivities and/or the reciprocal relative dispersion, $\Gamma$, of the gas, and this information is used in subsequent calculations of displacement to compensate for errors that would otherwise be uncompensated with the customary dispersion interferometry To further enhance the accuracy of such displacement calculations, wavelength monitor 416 receives a portion of beams 432 as beams 464, which have been provided by reflection from beamsplitter 434. Beamsplitter 434 also transmits a portion of beams 432 as beams 466, which are reflected from mirror 468 for travel to intrinsic property monitor 418 as beams 470. Wavelength monitor 416 assesses the accuracy of the wavelengths of beams 464 and provides information about that accuracy as signal 471 for use by intrinsic property monitor 418 and electronic processor 420.

In addition, source 412 provides information about the wavelengths generated thereby in the form of signals 472 and 474 that are sent to electronic processor 420 for use in either correcting calculations or providing feedback control signals to improve the accuracy of the wavelengths of the beams generated by source 412, and/or eliminating phase redundancy.

Intrinsic property monitor 418 generates a signal 476 containing information about the intrinsic optical properties of the gas, and this information is used in conjunction with the other information provided to electronic processor 420 to either calculate the corrected displacement in the measurement leg of interferometer 414 or is sent to computer 422 for similar use. For details of various forms for intrinsic optical property monitor 418 and wavelength monitor 416 reference may be made to commonly owned U.S. patent application Ser. No. 09/232,515 entitled APPARATUS AND METHODS FOR MEASURING INTRINSIC OPTICAL PROPERTIES OF A GAS which was filed on Jan. 19, 1999 in the name of Henry Allen Hill and which is specifically incorporated herein by reference in its entirety.

As will be seen, electronic processor 420 may also be provided with means for compensating for cyclic errors in the dispersion term and/or the dispersion term and fundamental phase terms available from dispersion interferometer 414.

In practice, intrinsic property monitor 418 is preferably placed as close to the measurement leg of interferometer 414 as sensible, and if a stream of gas is directed over the measurement leg, as is commonly the case in lithographic processes, monitor 418 is preferably placed upstream, or upwind, of the measurement leg.

The output signal 476 of monitor may also be monitored to develop statistical information about its variation or rate of variation in time, and if appropriate, the most recent or the historical data may be updated to reflect changes that exceed predetermined control limits.

Having described the invention in general terms, specific detailed embodiments will now be taken up.

Figure 1A:
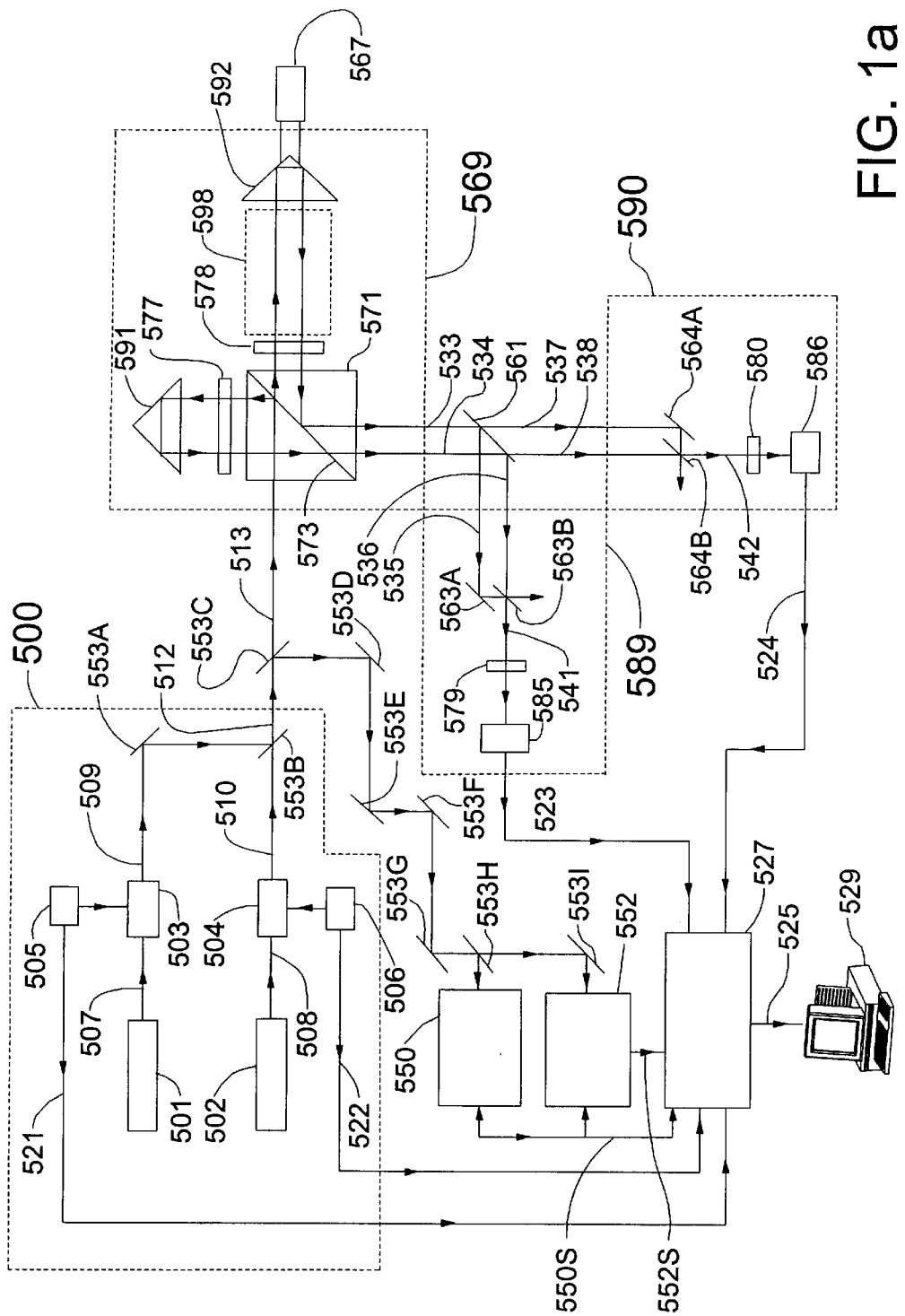
FIG. 1a shows in diagrammatic form a first detailed embodiment of the invention for measuring and monitoring the refractivity of a gas in at least one of a measurement path and a reference path and/or the relative change in optical path length of the measurement and reference paths due to the gas.
Figure 1B:
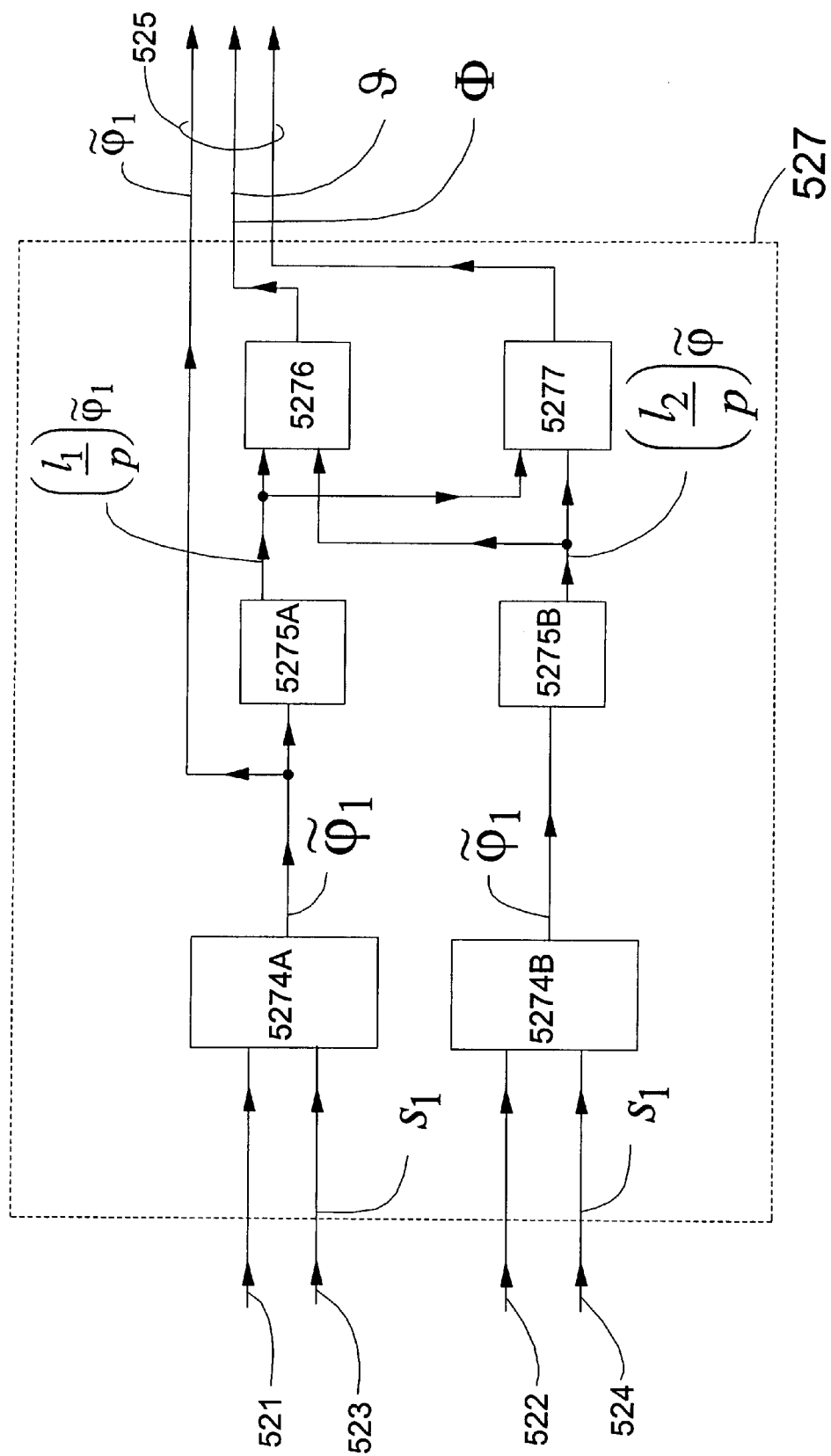

Reference is now made to FIGS. 1a and 1b which depict in schematic form a first embodiment of the present invention for measuring and monitoring the refractivity of a gas in at least one of a measurement path and a reference path and/or the relative change in the optical path length of the measurement and reference paths due to the gas. Either or both the refractive index of the gas and the relative physical length of the measurement and reference paths may be changing. For some end use applications, the effects of cyclic errors in corrections for effects of the gas in the at least one of the measuring and reference paths, corrections generated from optical dispersion related signals, are compensated to a certain level of accuracy. The certain level of accuracy is determined in part by the magnitude of cyclic error effects in measured values of relative measurement and reference path lengths at the respective wavelengths of the optical dispersion related signals. While the apparatus has application for a wide range of radiation sources, the following description is taken by way of example with respect to an optical measuring system.

The first embodiment comprises, as shown in FIG. 1a, a source 500, an interferometer 569, detectors 589 and 590, a monitor 550 of the reciprocal dispersive power $\Gamma$ of the gas in the at least one of the measurement and reference paths of interferometer 569, a monitor 552 of the wavelengths of the different wavelength components of an output beam of source 500, an electronic processor 527, and a computer 529.

Referring to source 500 as shown in FIG. 1a, a light beam 507 emitted from source 501 passes through a modulator 503 becoming light beam 509. Modulator 503 is excited by a driver 505. Source 501 is preferably a laser or like source of coherent radiation, preferably polarized, and having a wavelength $\lambda_1$. Modulator 503 may, for example, be an acousto-optical device or a combination of acousto-optical devices with additional optics for selectively modulating polarization components of beam 507. Modulator 503 preferably shifts the oscillation frequency of one linearly polarized component of beam 507 an amount $f_1$ with respect to an orthogonally linearly polarized component. The directions of polarizations of the components of beam 507, denoted herein as x and y, are parallel and orthogonal, respectively, to the plane of FIG. 1a. The oscillation frequency $f_1$ is determined by the driver 505.

In a next step, a light beam 508 emitted from a source 502 passes through a modulator 504 becoming light beam 510. Modulator 504 is excited by an electronic driver 506 similar to the excitation of modulator 503 by electronic driver 505, respectively. Source 502, similar to source 501, is preferably a laser or like source of polarized, coherent radiation, but preferably at a different wavelength, $\lambda_2$. Modulator 504 preferably shifts the oscillation frequency of one linearly polarized component of beam 508 an amount $f_2$ with respect to an orthogonally linearly polarized component, the directions of polarizations of the components being in x and y directions, respectively. The oscillation frequency $f_2$ is determined by electronic driver 506. The magnitude of frequency shifts $f_1$ and $f_2$ are generally much smaller than the magnitude of the difference in optical frequencies of beams 507 and 508.

Light sources 501 and 502 and modulators 503 and 504 can be any of a variety of frequency modulation apparatus and/or lasers. For example, the laser can be a gas laser, e.g., a HeNe laser, stabilized in any of a variety of conventional techniques known to those skilled in the art, see for example, T. Baer et al., "Frequency Stabilization of a 0.633 μm He—Ne-longitudinal Zeeman Laser," *Applied Optics,* 19, 3173–3177 (1980); Burgwald et al., U.S. Pat. No. 3,889,207, issued Jun. 10, 1975; and Sandstrom et al., U.S. Pat. No. 3,662,279, issued May 9, 1972. Alternatively, the laser can be a diode laser frequency stabilized in one of a variety of conventional techniques known to those skilled in the art, see for example, T. Okoshi and K. Kikuchi, "Frequency Stabilization of Semiconductor Lasers for Heterodyne-type Optical Communication Systems," *Electronic Letters,* 16, 179–181 (1980) and S. Yamaqguchi and M. Suzuki, "Simultaneous Stabilization of the Frequency and Power of an AlGaAs Semiconductor Laser by Use of the Optogalvanic Effect of Krypton," *IEEE J. Quantum Electronics,* QE-19, 1514–1519 (1983).

Two optical frequencies may be produced by one of the following techniques: (1) use of a Zeeman split laser, see for example, Bagley et al., U.S. Pat. No. 3,458,259, issued Jul. 29, 1969; G. Bouwhuis, "Interferometrie Mit Gaslasers," Ned. T. Natuurk, 34, 225–232 (August 1968); Bagley et al., U.S. Pat. No. 3,656,853, issued Apr. 18, 1972; and H. Matsumoto, "Recent interferometric measurements using stabilized lasers," *Precision Engineering,* 6 (2), 87–94 (1984); (2) use of a pair of acousto-optical Bragg cells, see for example, Y. Ohtsuka and K. Itoh, "Two-frequency Laser Interferometer for Small Displacement Measurements in a Low Frequency Range," *Applied Optics,* 18(2), 219–224 (1979); N. Massie et al., "Measuring Laser Flow Fields With a 64-Channel Heterodyne Interferometer," *Applied Optics,* 22 (14), 2141–2151 (1983); Y. Ohtsuka and M. Tsubokawa, "Dynamic Two-frequency Interferometry for Small Displacement Measurements," *Optics and Laser Technology,* 16, 25–29 (1984); H. Matsumoto, ibid.; P. Dirksen, et al., U.S. Pat. No. 5,485,272, issued Jan. 16, 1996; N. A. Riza and M. M. K. Howlader, "Acousto-optic system for the generation and control of tunable low-frequency signals," *Opt. Eng.,* 35 (4), 920–925 (1996); (3) use of a single acousto-optic Bragg cell, see for example, G. E. Sommargren, commonly owned U.S. Pat. No. 4,684,828, issued Aug. 4, 1987; G. E. Sommargren, commonly owned U.S. Pat. No. 4,687,958, issued Aug. 18, 1987; P. Dirksen, et al., ibid.; (4) use of two longitudinal modes of a randomly polarized HeNe laser, see for example, J. B. Ferguson and R. H. Morris, "Single Mode Collapse in 6328 Å HeNe Lasers," *Applied Optics,* 17 (18), 2924–2929 (1978); (5) use of birefringent elements or the like internal to the laser, see for example, V. Evtuhov and A. E. Siegman, "A "Twisted-Mode" Technique for Obtaining Axially Uniform Energy Density in a Laser Cavity," *Applied Optics,* 4 (1), 142–143 (1965); or the use of the systems described in commonly owned U.S. patent application with Ser. No. 09/061,928 filed Apr. 17, 1998 entitled "Apparatus to Transform Two Non-Parallel Propagating Optical Beam Components into Two Orthogonally Polarized Beam Components" by H. A. Hill, the contents of which are incorporated herein by reference.

The generation of beams by a single laser with two widely separated wavelengths and for each beam, a pair of orthogonally polarized components, one component of each pair frequency shifted with respect to the second component of the corresponding pair, is described in U.S. Pat. No. 5,732,095 entitled "Dual Harmonic-Wavelength Split-Frequency Laser" and issued March 1998 to P. Zorabedian.

The specific device used for the sources of beams 509 and 510 will determine the diameters and divergences of beams 509 and 510. For some sources, e.g., a diode laser, it will likely be necessary to use conventional beam-shaping optics, e.g., a conventional microscope objective, to provide beams 509 and 510 with suitable diameters and divergences for elements that follow. When a source is a HeNe laser, for example, beam-shaping optics may not be required.

The ratio of the wavelengths $(\lambda_1/\lambda_2)$ has a known approximate ratio value $l_1/l_2$, i.e.

$$(\lambda_1/\lambda_2) \cong (l_1/l_2), \tag{1}$$

where $l_1$ and $l_2$ comprise low order nonzero integer values or at least one non-integer nonzero value having a low order of magnitude. The x polarized components of beams 509 and 510 have oscillation frequencies shifted by amounts $f_1$ and $f_2$, respectively, with respect to the y polarized components of beams 509 and 510, respectively. In addition, the directions of the frequency shifts of the x components of beams 509 and 510 are the same.

It will be further appreciated by those skilled in the art that both the x and y polarization components of beam 509 and/or of beam 510 may be frequency shifted without departing from the scope and spirit of the invention, $f_1$ remaining the difference in frequencies of the x and y polarization components of beam 509 and $f_2$ remaining the difference in frequencies of the x and y polarization components of beam 510. Improved isolation of an interferometer and a laser source is generally possible by frequency shifting both x and y polarization components of a beam, the degree of improved isolation depending in part on the means used for generating the frequency shifts.

In a next step, beam 509 is reflected by mirror 553A and a portion thereof reflected by dichroic non-polarizing beam splitter 553B to become a $\lambda_1$ component of beam 512. A portion of beam 510 is transmitted by dichroic non-polarizing beam splitter 553B to become a second component, a $\lambda_2$ component, of beam 512 wherein the $\lambda_2$ component is preferably parallel and coextensive with the $\lambda_1$ component.

Next, a first portion of beam 512 is transmitted by non-polarizing beam splitter 553C as beam 513. Beam 513 propagates to an interferometer 569 comprised of optical means for introducing a phase shift $\phi_1$ between x and y polarization components of the $\lambda_1$ component of beam 513 and a phase shift $\phi_2$ between x and y polarization components of the $\lambda_2$ component of beam 513. In a further step, a second portion of beam 512 is reflected by non-polarizing beam splitter 553C and, after subsequent reflections by mirrors 553D, 553E, 553F, and 553G, a first portion thereof is reflected by non-polarizing beam splitter 553H as an input beam to monitor 550 and a second portion thereof is transmitted by non-polarizing beam splitter 553H as an input beam to monitor 552.

Monitors 550 and 552 are wavelength and Γ monitors, respectively. The Γ monitor 552 is shown in FIG. 1a as physically displaced from interferometer 569. In practice it is preferably located in close proximity to the at least one of the measurement and reference paths occupied by the gas. If there is in the environment of interferometer 569 an air flow with a known air flow pattern, it is further preferable to locate Γ monitor 552 up stream, as defined by the known air flow pattern, of the at least one of the measurement and reference paths occupied by the gas. In addition, the location of Γ monitor 552 is preferably up stream of sources of contaminants that may alter a local value of Γ. For example, when the apparatus of the present invention is part of a lithographic system, a potential source of local contaminants is gas effluents from the photoresist on a wafer during an exposure process.

The magnitude of phase shifts $\phi_1$ and $\phi_2$ are related to round-trip physical length L of measurement path 598 according to the formulae $$\phi_i = Lpk_i n_i, \quad i=1 \text{ and } 2, \tag{2}$$

where p is the number of passes through the respective reference and measurement legs for a multiple pass interferometer, and $n_i$ is the refractive index of gas in measurement path 598 corresponding to wavenumber $k_i = (2\pi)\lambda_i$. Eq. (2) includes the effect of the gas in only the measurement path so as to present the function of the present invention in the simplest manner without departing from the scope and spirit of the present invention. The generalization of Eq. (2) to include the effect of gas in the reference leg is a straight forward procedure for those skilled in the art.

As shown in FIG. 1a, interferometer 569 comprises a reference retroreflector 591, an object retroreflector 592 with a position controlled by translator 567, quarter-wave phase retardation plates 577 and 578, and a polarizing beam splitter 571. This configuration is known in the art as a polarized Michelson interferometer and is shown as a simple illustration with p=1.

Eqs. (2) are valid for the case where the paths in the gas for beams with one wavelength and the paths for beams with the second wavelength are substantially coextensive, a case chosen to illustrate in the simplest manner the function of the invention in the first embodiment. To those skilled in the art, the generalization to the case where the respective paths for beams with the two different wavelengths are not substantially coextensive is a straight forward procedure.

After passing through interferometer 569, the portion of beam 513 passing through the measurement path becomes a phase-shifted beam 533 and the portion of beam 513 passing through the reference path containing retroreflector 591 becomes phase-shifted beam 534. The measurement beam 533 and the reference beam 534 have each traversed twice quarter-wave phase retardation plates 678 and 677, respectively, rotating the polarizations of each of the measurement and reference beams by 90°. Phase-shifted beams 533 and 534 are polarized orthogonal to the plane and in the plane of FIG. 1a, respectively. A conventional dichroic beam splitter 561 separates those portions of beam 533 corresponding to wavelengths $\lambda_1$ and $\lambda_2$ into beams 535 and 537, respectively, and those portions of beam 534 corresponding to wavelengths $\lambda_1$ and $\lambda_2$ into beams 536 and 538, respectively. Beams 535 and 536 enter detector system 589 and beams 537 and 538 enter detector system 590.

In detector system 589 as shown in FIG. 1a, beam 535 is first reflected by mirror 563A and then reflected by polarizing beam splitter 563B to form one component of beam 541. Beam 536 is transmitted by polarizing beam splitter 563B to become a second component of beam 541. In detector system 590, beam 537 is first reflected by mirror 564A and then reflected by polarizing beam splitter 564B to form one component of beam 542. Beam 538 is transmitted by polarizing beam splitter 564B to become a second component of beam 542. Beams 541 and 542 pass through polarizers 579 and 580, respectively, impinge upon photodetectors 585 and 586, respectively, and generate preferably by photoelectric detection two electrical interference signals. The two electrical interference signals comprise two heterodyne signals $s_1$ and $s_2$, respectively. Polarizers 579 and 580 are preferably oriented so as to mix x and y polarization components of beams 541 and 542, respectively. Heterodyne signals $s_1$ and $s_2$ correspond to wavelengths $\lambda_1$ and $\lambda_2$, respectively, and are transmitted to electronic processor 527 for analysis as electronic signals 523 and 524, respectively, in either digital or analog format, preferably in digital format.

Signals $s_i$, i=1 and 2, have the form $$s_i = A_i(t) \cos[\alpha_i(t)], \quad i=1 \text{ and } 2. \tag{3}$$

Time-dependent arguments $\alpha_i(t)$ are given by $$\alpha_i(t) = 2\pi f_i t + \phi_i + \Lambda_i, \quad i=1 \text{ and } 2, \tag{4}$$

where phase offsets $\zeta_i$ comprise all contributions to arguments $\alpha_i$ that are not related or associated with measurement path 598 or reference paths and not related or associated with nonlinear errors and the $\Lambda_i$ comprise the nonlinear errors including cyclic error terms.

Signal $s_i$ is the real part, $\hat{s}_{i,R}$, of a complex number $\hat{s}_i$ where $s_i$ comprises a causal, stable, i.e., absolutely summable, real sequence. Thus, the Fourier transform $S_{i,R}(j\omega)$ of $s_i$ completely defines $S_i(j\omega)$ [see Chapter 10 "Discrete Hilbert Transforms" in *Discrete-Time Signal Processing*, (Prentice Hall, 1989) by A. V. Oppenheim and R. W. Schafer] where $$S_i(j\omega) = S_{i,R}(j\omega) + iS_{i,I}(j\omega), \quad i=1 \text{ and } 2, \tag{5}$$

$S_{i,I}(j\omega)$ is the imaginary component of $S_i(j\omega)$, $\omega$ is an angular frequency, and j is the imaginary number $\sqrt{(-1)}$. The imaginary component $\hat{s}_{i,I}$ of $\hat{s}_i$ is obtained from the inverse Fourier transform of $S_{i,I}(j\omega)$ with $$\hat{s}_{i,I} = A_i(t) \sin[\alpha_i(t)], \quad i=1 \text{ and } 2. \tag{6}$$

The phase $\alpha_i(t)$ can be obtained from $\hat{s}_{i,R}$ and $\hat{s}_{i,I}$ according to the formulae $$\alpha_i(t) = \arctan\left(\frac{s_{i,I}}{s_{i,R}}\right), \quad i = 1 \text{ and } 2. \tag{7}$$

Referring now to FIG. 1b, electronic processor 527 comprises electronic processors 5274A and 5274B to determine measured phases $\phi_1$ and $\phi_2$, respectively, from measured phases $\alpha_1$ and $\alpha_2$, respectively, $$\phi_i = \phi_i + \zeta_i + \Lambda_i, \quad i=1 \text{ and } 2, \tag{8}$$

by either digital or analog signal processes, preferably digital processes, using time-based phase detection such as a digital Hilbert transform phase detector (R. E. Best, ibid.) or the like and the phase of electronic drivers 505 and 506, respectively.

The phases of electronic drivers 505 and 506 are transmitted by electrical signals, reference signals 521 and 522, respectively, in either digital or analog format, preferably in digital format, to electronic processor 527. Reference signals, alternatives to reference signals 521 and 522, may also be generated by an optical pick off means and detectors (not shown in figures) by splitting off portions of beams 509 and 510 with beam splitters, preferably non-polarizing beam splitters, mixing the respective portions of beam 509 and beam 510 that are split off, and detecting the mixed portions to produce alternative heterodyne reference signals. It may be desirable to transmit the different polarization components of beams from source 500 to interferometer 569 as spatially separated components (not shown in FIG. 1a) so as to effect, e.g., a reduction of certain cyclic errors components of $\Lambda_1$ and $\Lambda_2$. For the case of separated beam transport from source 500 to interferometer 569, the optical pick off means is preferably located in close proximity to the input to interferometer 569.

Referring again to FIG. 1b, phase $\phi_1$ and phase $\phi_2$ are next multiplied by $l_1/p$ and $l_2/p$, respectively, in electronic processors 5275A and 5275B, respectively, preferably by digital processing, to produce phases $(l_1/p)\phi_1$ and $(l_2/p)\phi_2$, respectively. Phases $(l_1/p)\phi_1$ and $(l_2/p)\phi_2$ are next added together in electronic processor 5276 and subtracted one from the other in electronic processor 5277, preferably by digital processes, to create the phases $\Theta$ and $\Phi$, respectively. Formally, $$\vartheta = \left(\frac{l_2}{p}\tilde{\varphi}_2 + \frac{l_1}{p}\tilde{\varphi}_1\right), \tag{9}$$

$$\Phi = \left(\frac{l_2}{p}\tilde{\varphi}_2 - \frac{l_1}{p}\tilde{\varphi}_1\right). \tag{10}$$

Using the definitions given by Eqs. (8), phases $\Theta$ and $\Phi$ can also be written as $$\vartheta = \{L[\chi(n_2+n_1) + K(n_2-n_1)] + \left(\frac{1}{p}\right)(l_2\zeta_2 + l_1\zeta_1) + \left(\frac{1}{p}\right)[l_2\Lambda_2(\varphi_2) + l_1\Lambda_1(\varphi_1)]\}, \tag{11}$$

$$\Phi = \{L[\chi(n_2-n_1) + K(n_2+n_1)] + \left(\frac{1}{p}\right)(l_2\zeta_2 - l_1\zeta_1) + \left(\frac{1}{p}\right)[l_2\Lambda_2(\varphi_2) - l_1\Lambda_1(\varphi_1)]\}, \tag{12}$$

where $$\chi(l_2k_2+l_1k_1)/2, \tag{13}$$

$$K(l_2k_2-l_1k_1)/2. \tag{14}$$

The phases $\phi_1$, $\Theta$ and $\Phi$ are transmitted to computer 529 as signal 525, in either digital or analog format, preferably in digital format.

The noncyclic non-linearity $\eta_i$ is not addressed further in the first embodiment and thus omitted in subsequent description of the first embodiment.

For a measuring path comprised of a vacuum, phase $\Phi$ should substantially be a constant independent of Doppler shifts due to a motion of retroreflector 592. This may not be the case in practice due to differences in the group delay experienced by heterodyne signals $s_1$ and $s_2$. Group delay, often called envelope delay, describes the delay of a packet of frequencies and the group delay at a particular frequency is defined as the negative of the slope of the phase curve at the particular frequency [see H. J. Blinchikoff and A. I. Zverev, *Filtering in the Time and Frequency Domains*, Section 2.6, 1976 (Wiley, N.Y.)]. If phase $\Phi$ is not a constant for a measuring path comprised of a vacuum, techniques known to those skilled in the art can be used to compensate for departures of phase $\Phi$ from a constant (cf. Blinchikoff and Zveriv, ibid.). It is important to note that the group delay effects in $\Phi$ can not only be detected but can also be determined by measuring $\Phi$ as a function of different translational velocities of retroreflector 592 produced by translator 567 for a measuring path comprising a vacuum. It is also important to note that the group delay effects in $\Phi$ can be significantly reduced by performing analog-to-digital conversion of signals $s_1$ and $s_2$ as close as practical to the photoelectric detectors in detectors 585 and 586, respectively, followed by digital signal processing as opposed to transmitting signals $s_1$ and $s_2$ as analog signals for subsequent analog signal processing and/or analog-to-digital conversion downstream. The compensation for a particular group delay can generally be introduced before or after, or in part before and in part after, the processing elements producing the particular group delay.

The dispersion $(n_2-n_1)$ of the gas can be determined from $\Theta$ and $\Phi$ using the formula $$(n_2-n_1) = \frac{1}{\chi L[1-(K/\chi)^2]}\{[\Phi - \vartheta(K/\chi)] + Q_\psi + Q\}, \tag{15}$$

where $$Q_\psi = \xi_\psi(K/\chi) - Z_\psi, \tag{16}$$

$$\xi_\psi = \left(\frac{l_2}{p}\psi_2 + \frac{l_1}{p}\psi_1\right), \tag{17}$$

$$Z_\psi = \left(\frac{l_2}{p}\psi_2 - \frac{l_1}{p}\psi_1\right), \tag{18}$$

$$Q = \xi(K/\chi) - Z, \tag{19}$$

$$\xi = \left(\frac{l_2}{p}\zeta_2 + \frac{l_1}{p}\zeta_1\right), \tag{20}$$

$$Z = \left(\frac{l_2}{p}\zeta_2 - \frac{l_1}{p}\zeta_1\right). \tag{21}$$

For those applications related to distance measuring interferometry, the heterodyne phase $\phi_1$ and phases $\Theta$ and $\Phi$ may be used to determine the distance L as a quantity independent of the effects of the refractive index of the gas in the measuring path of the distance measuring interferometer using the formula $$L = \frac{1}{(\chi-K)}\left\{\begin{array}{l}\frac{l_1}{p}(\tilde{\varphi}_1 - \zeta_1 - \psi_1) - \\ \frac{\Gamma}{[1+(K/\chi)]}[\Phi - (K/\chi)\vartheta + Q_\psi + Q]\end{array}\right\} \tag{22}$$

where $\Gamma$, the reciprocal dispersive power of the gas, is defined as $$\Gamma = \frac{(n_1-1)}{(n_2-n_1)}. \tag{23}$$

It is evident from the definition of K given by Eq. (14) that $(K/\chi)=0$ corresponds to the wavelengths $\lambda_1$ and $\lambda_2$ being strictly harmonically related according to the known ratio $l_1/l_2$. For an application where $|K/\chi|>0$ and the value of $(K/\chi)$ must be known to a certain precision in the use of Eqs. (15) and/or (22) to meet an end use requirement, $(K/\chi)$ is measured by wavelength monitor 550. For an application where the value of $\chi$ must be known to another certain precision in the use of Eqs. (15) and/or (22), $\chi$ is measured by wavelength monitor 550. Measured values of $(K/\chi)$ and χ are transmitted as signal 551 to electronic processor 527 as required as well to Γ monitor 552 as required for use in determination of Γ, preferably in digital format.

The reciprocal dispersive power Γ is measured and monitored by monitor 552. The preferred embodiment for Γ monitor 552 is from the second group of Γ monitor embodiments subsequently described herein. Measured values of Γ are transmitted as signal 553 to electronic processor 527, preferably in digital format.

The relative precision to which the dispersion $(n_2-n_1)$ can be determined is limited in part by the effect of cyclic errors, the magnitude of the effect, according to Eq. (15), being of the order of $$\left[\left(\frac{l_i}{p}\right)|\psi_i|\right] / L\chi(n_2 - n_1), i = 1 \text{ and } 2. \quad (24)$$

Consider for example, an application where $\lambda_1=0.6334$ μm, $\lambda_1=2\lambda_2$, p=1, L=0.5 m, and the gas is comprised of air at 25° C. and a pressure of one atmosphere. For the example conditions, the magnitude of the contribution of $\psi_1$, to the relative precision as expressed by Eq. (24) is $$\approx 0.017|\psi_1|, \quad (25)$$

$\psi_1$ being expressed in radians and $|\psi_1|$ indicating the absolute value of $\psi_1$. Continuing with the example, for a specific cyclic error of $|\psi_1|=0.1$ radians, a cyclic error in phase corresponding in the example to a cyclic error in a distance measurement of 5 nm, the specific cyclic error limits the relative precision to which the dispersion $(n_2-n_1)$ can be measured to ≈0.2%. If a source for the $\lambda_1$ beam is a NbYAG laser with $\lambda_1=1.06$ μm, the corresponding limits on the relative precision to which the dispersion $(n_2-n_1)$ can be measured is ≈0.5%.

The limitations of effects of cyclic errors on the relative precision to which the dispersion $(n_2-n_1)$ can be determined propagate directly to limitations of the effects of cyclic errors on corrections for refractivity effects of gas in a measurement path of a distance measuring interferometer using dispersion interferometry. From inspection of Eq. (22), it is evident that the magnitude of the cyclic error contribution of $\psi_i$ entering through $Q_\psi$ is $\equiv \Gamma|\psi_i|$ relative to the magnitude of the cyclic error contribution $|\psi_1|$ entering through $\phi_1$. For the two cases of $\lambda_1=0.633$ μm with $\lambda_1=2\lambda_2$ and $\lambda_1=1.062$ μm also with $\lambda_1=2\lambda_2$, the values for Γ are 21.4 and 64.6, respectively. Thus the effects of cyclic error contributions to the correction term in Eq. (22) for the refractivity of a gas in a measuring path must be reduced by approximately one and a half or more orders of magnitude if the effects of the cyclic error contributions resulting from the correction term are to be of the order of or less than the effects of the cyclic error contributions resulting directly from $\phi_1$.

A spectral representation of the cyclic non-linearity $\psi_i$, in terms of $\phi_1$ and $\phi_2$, can be based on different families of orthogonal polynomials and functions. Two examples are a series comprising Fourier sine and cosine functions and a series comprising Chebyshev polynomial functions. Without departing from the spirit and scope of the present invention, the Fourier sine and cosine series spectral representation of $\psi_i$ will be used in the subsequent embodiments and in the first embodiment is expressed as:

$$\psi_i(\varphi_i) = \left(\sum_{r=1} a_{ir}\cos r\varphi_i + \sum_{r=1} b_{ir}\sin r\varphi_i\right), i = 1 \text{ and } 2. \quad (26)$$

The $\psi_i$ are written in Eqs. (26) in terms of cosine and sine series terms with arguments of the series terms being harmonics of $\phi_i$. For some configurations of interferometers, in particular multiple pass interferometers, it is possible for a system comprising a source, interferometer, and detector to generate cyclic nonlinearities that are subharmonics of $\phi_i$. Should subharmonic cyclic errors be present in a system, Eqs. (26) are augmented so as to include cosine and sine series terms with arguments that are subharmonics $\phi_i$. The subsequent description of procedures for the determination of the coefficients in the cosine and sine series will be in terms of the series representations given by Eqs. (26) without departing from the spirit and scope of the present invention.

It is possible for a system comprising a source, interferometer, detector, and digital signal processing to generate cyclic non-linearities that are neither subharmonics or harmonics of $\phi_i$. The non-subharmonic, non-harmonic cyclic errors are produced for example by aliasing in the digital signal processing and have frequencies which are aliases of harmonics and subharmonics of $\phi_i$. Should non-subharmonic, non-harmonic cyclic errors be present in a system, Eqs. (26) are augmented so as to include cosine and sine series terms with arguments that are the appropriate aliases of harmonics and/or subharmonics of $\phi_i$. The subsequent description of procedures to determine the coefficients in the cosine and sine series will be in terms of the series representations given by Eqs. (26) without departing from the spirit and scope of the present invention.

The spectral representation given by Eqs. (26) is in general valid for an interferometer where the phase of the heterodyne signal is changing at substantially a constant rate. The coefficients of the spectral representation given by Eqs. (26) will in general depend on the rate of change of the phase as a result, for example, of the properties of group delay experienced by a heterodyne signal (see discussion of group delay with respect to a frequency dependence of Φ).

In a next step, Φ is measured as a function of $\phi_1$ and $\phi_2$ over a certain range of values of $\phi_1$ and $\phi_2$. The measured values of Φ can be written, according to Eq. (12), as $$\Phi = L_\chi(n_2-n_1)+LK(n_2+n_1)+Z_\psi+Z. \quad (27)$$

The cyclic error terms $Z_\psi$ given by Eq. (18) can be expressed as $$\left(\frac{1}{p}\right)[l_2\psi_2(\varphi_2) - l_1\psi_1(\varphi_1)]. \quad (28)$$

For changes in L of the order of $10\lambda_1$ to $100\lambda_1$, it is evident from Eq. (27) that, for the condition $K/\chi \leq [(n_2-n_1)/n_2+n_1)]$, the $Z_\psi$ term is the dominant term with respect generating changes in Φ, typically by several orders of magnitude, other terms K, χ, and Z being constants and $[(n_2-n_1)/n_2+n_1)] \leq 1/(2 \times 10^5)$ for air at 25° C. and at a pressure of one atmosphere, $\lambda_1 \geq 0.6$ μm, and $\lambda_1 \equiv 2\lambda_2$. As a consequence, the measured values of Φ can be used directly in an effective procedure for determination of $Z_\psi$.

The ratio of the wavelengths $\lambda_1/\lambda_2$ in the first embodiment can be expressed as the ratio $l_1/l_2$ as per Eq. (1) with a certain relative precision. The ratio of $\phi_1/\phi_2$ can therefore be expressed as $$\frac{\varphi_1}{\varphi_2} = \frac{l_2}{l_1} \quad (29)$$

with the same certain relative precision. The two parameter representation of $Z_\psi$, the two parameters being $\phi_1$ and $\phi_2$ according to Eqs. (18) and (26), can be reduced to a one parameter representation by using Eq. (29) to eliminate either $\phi_1$ or $\phi_2$ in the two parameter representation of $Z_\psi$. The subsequent description of the first embodiment will be in terms of the elimination of $\phi_2$, although the elimination of $\phi_1$ could have been chosen as the parameter to eliminate yielding substantially the same end results in terms of the determination of $Z_\psi$. The resulting one parameter representation for $Z_\psi$, a reduced representation $\hat{Z}_\psi$, is $$\hat{Z}_\psi = \left(\frac{l_2}{p}\right)\left[\sum_{r=1} a_{2,r}\cos r\left(\frac{l_1}{l_2}\right)\varphi_1 + \sum_{r=1} b_{2,r}\sin r\left(\frac{l_1}{l_2}\right)\varphi_1\right] - \left(\frac{l_1}{p}\right)\left(\sum_{r=1} a_{1,r}\cos r\varphi_1 + \sum_{r=1} b_{1,r}\sin r\varphi_1\right). \quad (30)$$

The accuracy of the reduced representation $\hat{Z}_\psi$ of $Z_\psi$ is determined in part by the certain relative precision that $\lambda_1/\lambda_2$ is expressed as the ratio $l_1/l_2$.

The procedure for evaluation of the Fourier coefficients of the reduced representation $\hat{Z}_\psi$ uses $\phi_1$ as the variable of integration in the Fourier analysis of $Z_\psi$. The interval of integration in the Fourier analysis is an interval of $\phi_1$, $\Delta\phi_1$, such that $\Delta\phi_1$ is a multiple of $2\pi$ and, in addition, $l_1\Delta\phi_1/l_2$ is a multiple of $2\pi$ to a certain accuracy. The relative precision to which the cyclic error term $Z_\psi$ can be determined by the first embodiment will have a magnitude of the order of magnitude of ½ the cyclic error, expressed in radians, in $\phi_1$, or if larger, the effect of the certain relative precision that the ratio of wavelengths ($\lambda_1/\lambda_2$) is expressed as the ratio of $l_1/l_2$ and/or the certain accuracy that $l_1\Delta\phi_1/l_2$ is a multiple of $2\pi$. Thus the residual contribution of cyclic errors to $\Phi$ post correction for cyclic error effects will enter as a second order effect, first order in the cyclic errors in $\Phi$ and some combination of first order effects such as the cyclic errors in $\phi_1$, the certain relative precision that the ratio of wavelengths ($\lambda_1/\lambda_2$) is expressed as the ratio of $l_1/l_2$, and the certain accuracy that $l_1\Delta\phi_1/l_2$ is a multiple of $2\pi$. Accordingly, the residual contribution of cyclic errors to the compensation for the gas in the measurement path 598 will enter as $\Gamma$ times the second order effect.

Computer 529 computes dispersion $(n_2-n_1)$ and physical displacement L as required for an end use application using Eqs. (15) and (22), respectively, and the respective measured quantities. The refractivity $(n_1-1)$ is computed using the Eqs. (15) and (23) and the measured value for $\Gamma$.

A first variant of the first embodiment of the present invention is described wherein the description of the first variant of the first embodiment is the same as that given for the description of the first embodiment except with respect to the treatment of cyclic errors. In the first variant of the first embodiment, the phase $\Phi$ given by Eq. (27) is filtered by either an integral transform of $\Phi$ with respect to $\phi_1$ over an interval of $l_1\Delta\phi_1/l_2$ or multiples thereof or the integral transform of $\Phi$ with respect to $\phi_2$ over an interval of $l_2\Delta\phi_2/l_1$ or multiples thereof.

The design of the integral transform algorithm is based on the properties of the reduced representation $\hat{Z}_\psi$. The residual contribution of cyclic errors to $\Phi$ post filtering by an integral transform will enter as a second order effect, first order in the cyclic errors in $\Phi$ and some other combination of first order effects in the cyclic errors in either $\phi_1$ or $\phi_2$ depending upon which of $\phi_1$ and $\phi_2$ are used in execution of the integral transform, the effect of the certain relative precision that the ratio of wavelengths ($\lambda_{11}/\lambda_{12}$) is expressed as the ratio of $l_{11}/l_{12}$, and the certain accuracy that $l_1\Delta\phi_1/l_2$ is a multiple of $2\pi$ or the certain accuracy that $l_1\Delta\phi_1/l_2$ is a multiple of $2\pi$, whichever one is used in the integral transform. For an optimal integral transform, the residual second order effect will have an order of magnitude of $Z_\psi$ multiplied by either ½ the magnitude of the some other combination of cyclic errors, expressed in radians, in either $\phi_1$ or $\phi_2$ whichever one is used in the integral transform, the effect of the certain relative precision that the ratio of wavelengths ($\lambda_{11}/\lambda_{12}$) is expressed as the ratio of $l_{11}/l_{12}$, and the certain accuracy that $l_1\Delta\phi_1/l_2$ is a multiple of $2\pi$ or the certain accuracy that $l_2\Delta\phi_2/l_1$ is a multiple of $2\pi$, whichever one is used in the integral transform.

The integral transform $\Phi_i^I$ of $\Phi$ is given by the formula $$\Phi_i^I = \frac{\int \Phi d\tilde{\varphi}_i}{\int d\tilde{\varphi}_i}, \, i = 1 \text{ and } 2, \quad (31)$$

where the range of integration over $\phi_i$ is such that $l_1\Delta\phi_1/l_2$ is a multiple of $2\pi$ for i=1 and such that $l_2\Delta\phi_2/l_1$ is a multiple of $2\pi$ for i=2.

The integral filter in Eq. (31) will, in practice, generally be implemented as a digital filter by a digital signal processor [see, e.g., J. G. Proakis and D. G. Manolakis, *DIGITAL SIGNAL PROCESSING: Principles, Algorithms, and Applications,* Second Edition, (Macmillan, N.Y.) 1992].

The first variant of the first embodiment does not place any restrictions on the motion of the mirror 592 in order to be effective other than that there be some motion initially corresponding to either $\Delta\phi_1$ or $\Delta\phi_2$, depending which phase variable is used in the integral transform procedure of the filter, or respective multiples thereof and that the cyclic errors do not change significantly between the periods when mirror 592 is moved over a distance corresponding to the phase space of $\Delta\phi_1$ or $\Delta\phi_2$ or respective multiples thereof used in the integral transform procedure of the filter. The reduction of cyclic errors by filtering in the first variant of the first embodiment effectively eliminates problems encountered in prior art based on filtering methods wherein there is an integration over fixed periods of time.

It is important to note that in the first variant of the first embodiment that the effects of turbulence in the gas do not effect the efficacy of the filtering procedure in the reduction of cyclic error effects except in third and higher order effects. The insensitivity of the efficacy of the filtering procedure is a consequence of the substantially coextensive paths of the different wavelength components of the measurement beam in the gas.

The remaining description of the first variant of the first embodiment is the same as corresponding portions of the description given for the first embodiment.

Figure 2A:
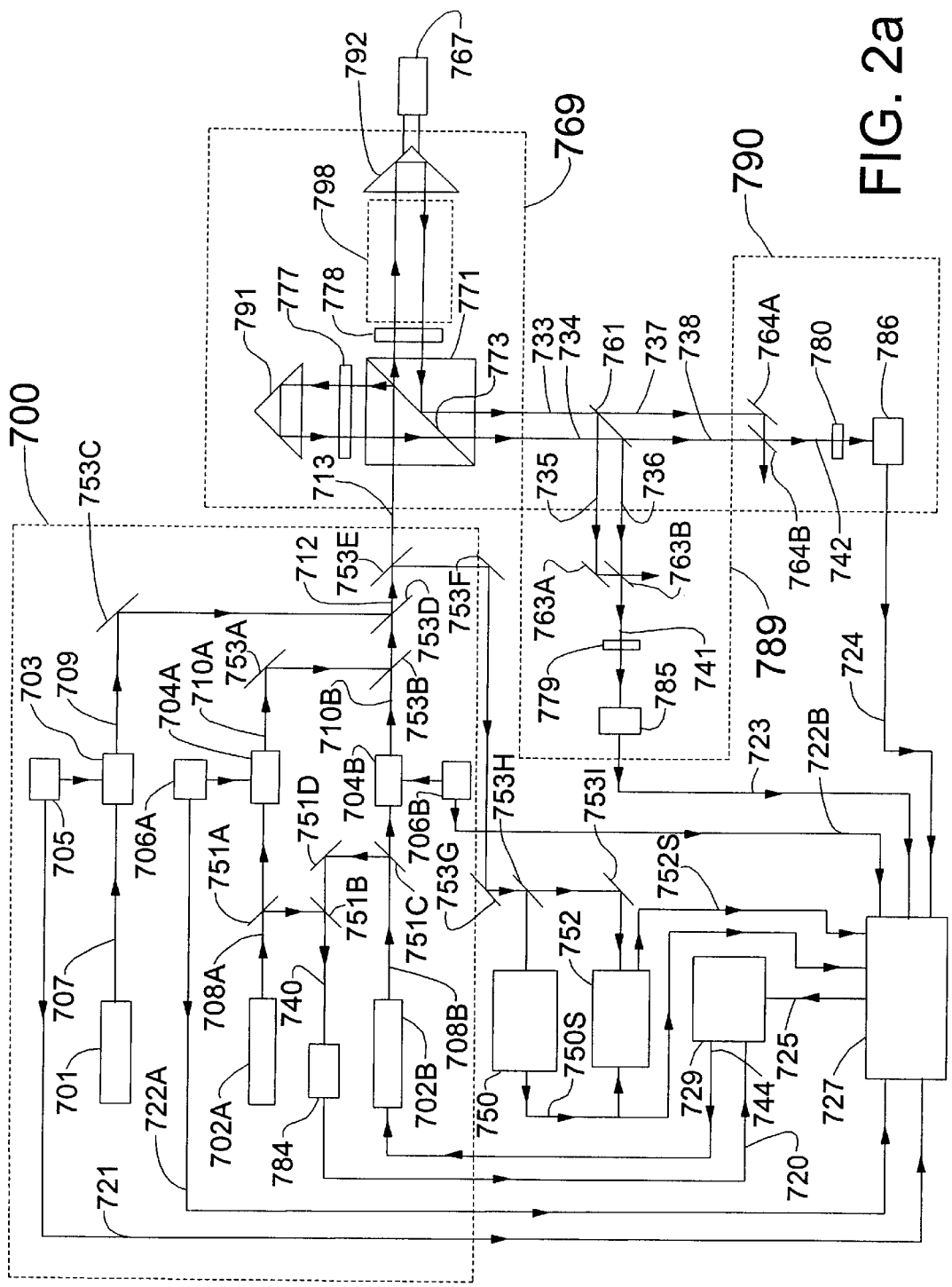
FIG. 2a depicts in diagrammatic form a second preferred embodiment of the present invention for measuring and correcting for effects of gas in at least one of a measurement path and a reference path of an angular or a linear displacement interferometer and correcting for effects of cyclic errors in both the measured phase used for determination of changes in relative optical path length of the measurement and reference paths and the associated optical dispersion related signal used to correct the changes in relative optical path length for effects of gas in the at least one of the measurement and reference paths.
Figure 2B:
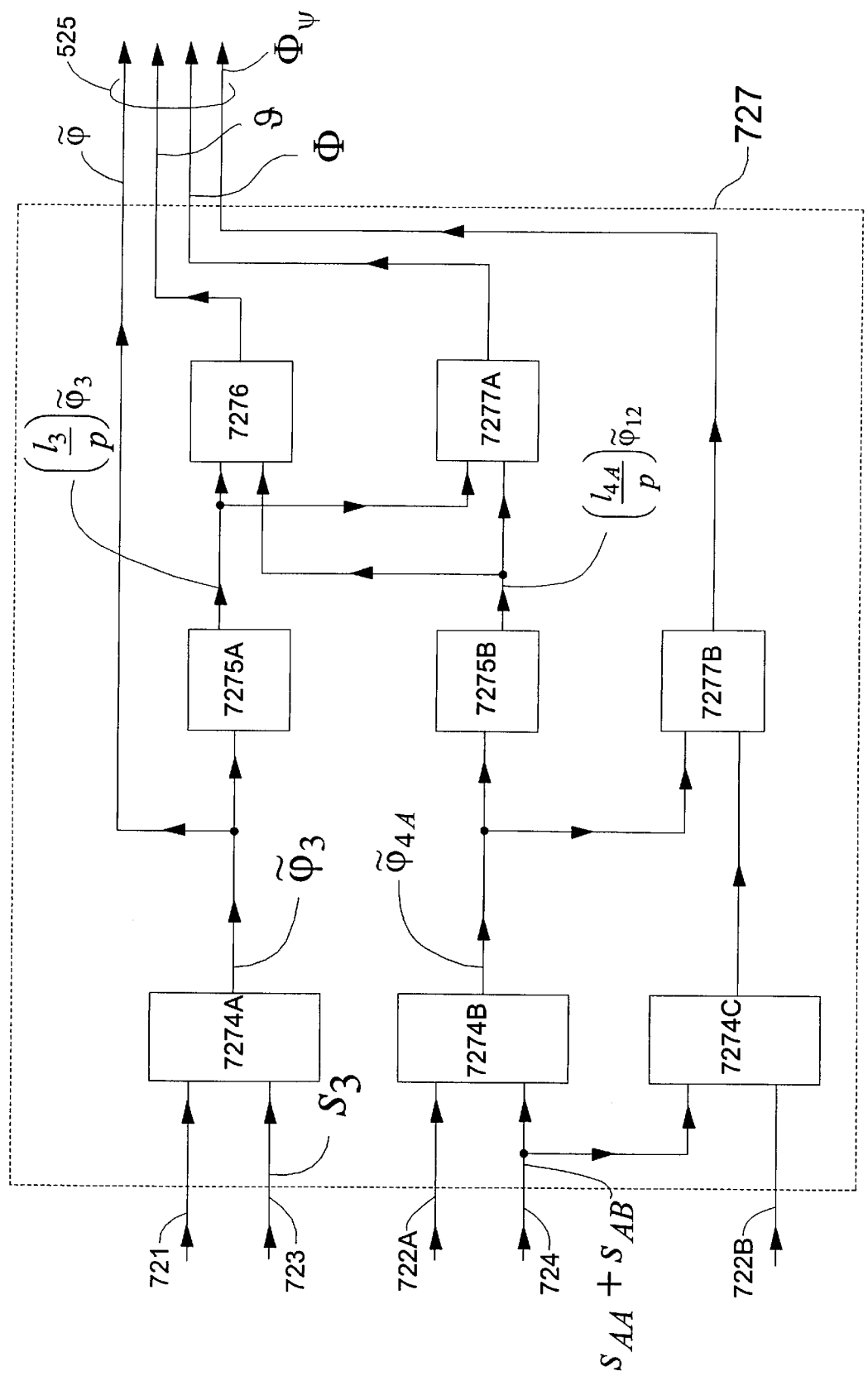

FIGS. 2a and 2b depict, in schematic form, a second preferred embodiment of the present invention. The second embodiment comprises apparatus and methods for measuring and correcting for effects of gas in at least one of a measurement path and a reference path of an angular or a linear displacement interferometer and correcting for effects of cyclic errors in both the measured phase used for determination of changes in relative optical path length of the measurement and reference paths and the associated optical dispersion related signal used to correct the changes in relative optical path length for effects of gas in the at least one of the measurement and reference paths. Either or both the refractive index of the gas and the relative physical length of the measurement and reference paths may be changing.

The interferometry system of the second embodiment comprises, as shown in FIG. 2a, a source system 700, an interferometer system 769, detectors 789 and 790, wavelength monitors 750 and 784, a Γ monitor 752, an electronic processor 727, and a computer and controller 729. This configuration is known in the art as a polarized Michelson interferometer and is shown as a simple illustration with p=1.

Many elements of the second embodiment shown in FIGS. 2a and 2b perform like functions as elements of the first embodiment in FIGS. 1a and 1b and unless indicated otherwise, the number of an element of the second embodiment in FIGS. 2a and 2b performing a like function as an element of the first embodiment being equal to the number of the element of the first embodiment in either FIG. 1a or 1b incremented by 200 and 2000, respectively. The descriptions of sources 701 and 702A are the same as corresponding portions of the descriptions given for sources 501 and 502, respectively, of the first embodiment. The description of source 702B is the same as corresponding portions of the description given for source 502 of the first embodiment except that the wavelength of source 702B is not fixed. Sources 701, 702A, and 702B generate beams 707, 708A, and 708B, respectively, with wavelengths $\lambda_3$, $\lambda_{4A}$, and $\lambda_{4B}$, respectively. Beams 707, 708A, and 708B are polarized in the plane of FIG. 2a.

Wavelength $\lambda_{4B}$ of the beam from source 702B is controlled by error signal 744 from computer and controller 729. For the second embodiment, $(\lambda_{4A}-\lambda_{4B})>0$ and $|\lambda_{4A}-\lambda_{4B}|<<\lambda_{4A}$ in order to illustrate in a simple manner the present invention. The second embodiment may be configured to be operative for negative values for $(\lambda_{4A}-\lambda_{4B})$ and/or for $\lambda_3$, $|\lambda_{4A}-\lambda_{4B}| \not\ll \lambda_{4A}$ without departing from the scope and spirit of the present invention. For configurations of the apparatus of the second embodiment where the condition $|\lambda_{4A}-\lambda_{4B}|<<\lambda_{4A}$ is not applicable, it may be desirable to change certain of the non-polarizing beam splitters described for the second embodiment to dichroic beam splitters to improve overall efficiency of the source system and interferometer system.

As shown in FIG. 2a, a first portion of beam 708A is reflected by non-polarizing beam splitter 751A and a portion thereof reflected by a non-polarizing beam splitter 751B to form a first component of beam 740. In a next step, a first portion of beam 708B is reflected by non-polarizing beam splitter 751C, reflected by mirror 751D, and a portion thereof transmitted by non-polarizing beam splitter 751B to form a second component of beam 740. Beam 740 impinges on wavelength monitor 784 configured to monitor the ratio $(\lambda_{4A}/\lambda_{4B})$. The measured value of the ratio $(\lambda_{4A}/\lambda_{4B})$ is transmitted to computer and controller 729 as electronic signal 720. Wavelength monitor 784 may comprise, for example, interferometers with or without a vacuum in a measurement leg and/or nonlinear elements such as β-BaBO$_3$ to double the frequency of a beam by second harmonic generation, SHG.

Computer and controller 729 generates error signal 744 related to the difference between the measured value of wavelength ratio $(\lambda_{4A}/\lambda_{4B})$, the ratio transmitted by signal 720, and a ratio specified by computer and controller 729. The wavelength of source 702B is controlled by error signal 744. Error signal 744 may control, for example, the wavelength of a laser by controlling the length of the laser cavity with a piezoelectric transducer or the wavelength of a diode laser by controlling the injection current of the diode laser.

Continuing with FIG. 2a, a second portion of beam 708A is transmitted by non-polarizing beam splitter 751A, enters modulator 704A, and exits modulator 704A as beam 710A comprised of two coextensive frequency components. Beam 710A is reflected by mirror 753A, a portion thereof reflected by non-polarizing beam splitter 753B, and a portion thereof transmitted by dichroic beam splitter 753D to form the $\lambda_{4A}$ component and frequency shifted $\lambda_{4A}$ component of beam 712. A second portion of beam 708B is transmitted by non-polarizing beam splitter 751C, enters modulator 704B, and exits modulator 704B as beam 710 B comprised of two coextensive frequency components. A portion of beam 710B is transmitted by non-polarizing beam splitter 753B and a portion thereof transmitted by dichroic beam splitter 753D to form the $\lambda_{4B}$ component and frequency shifted $\lambda_{4B}$ component of beam 712. Beam 707 enters and exits modulator 703 as beam 709 comprised of two coextensive frequency components. Beam 709 is reflected by mirror 753C and a portion thereof reflected by dichroic beam splitter 753D to form the $\lambda_3$ component and frequency shifted $\lambda_3$ component of beam 712.

The ratio of the wavelengths $(\lambda_3/\lambda_{4A})$ has a known approximate ratio value $l_3/l_{4A}$, i.e.

$$(\lambda_3/\lambda_{4A}) \equiv (l_3/l_{4A}), \tag{32}$$

where $l_3$ and $l_{4A}$ comprise low order non-zero integer values or at least one non-integer non-zero value having a low order of magnitude.

The descriptions of the modulators 703, 704A, and 704B and associated drivers 705, 706A, and 706B are the same as corresponding portions of descriptions given for drivers 503 and 504 and associated drivers 505 and 506 of the first embodiment. The frequency shifts introduced by modulators 703, 704A, and 704B are $f_1$, $f_{2A}$, and $f_{2B}$, respectively. The non-frequency-shifted components of beam 712 are polarized in the plane of FIG. 2A and the frequency-shifted components of beam 712 are polarized orthogonal to the plane of FIG. 2a. Frequency shifts $f_{2A}$ and $f_{2B}$ are different one from the other.

Next, a first portion of beam 712 is transmitted by non-polarizing beam splitter 753E as beam 713. Beam 713 propagates to an interferometer system 769 comprised of optical means for introducing a phase shift $\phi_3$ between x and y polarization components of the $\lambda_3$ component of beam 713, a phase shift $\phi_{4A}$ between x and y polarization components of the $\lambda_{4A}$ component of beam 713, and a phase shift $\phi_{4B}$ between the x and y polarization components of the $\lambda_{4B}$ component of beam 713. In a further step, a second portion of beam 712 is reflected by non-polarizing beam splitter 753E and, after subsequent reflections by mirrors 753F and 753G, a first portion thereof is reflected by non-polarizing beam splitter 753H as an input beam to wavelength monitor 750 and a second portion thereof is transmitted by non-polarizing beam splitter 753H as an input beam to Γ monitor 752.

The Γ monitor 752 is shown in FIG. 2a as physically displaced from interferometer system 769. In practice, the selection of the location of the Γ monitor relative to interferometer system 769 may be an important consideration with respect to performance of the second embodiment. In general, Γ monitor 752 is preferably located in close proximity to the at least one of the measurement and reference paths occupied by the gas. If the environment of interferometer system 769 comprises an air flow with a known air flow pattern, it is further preferable to locate Γ monitor 752 up stream, as defined by the known air flow pattern, of the at least one of the measurement and reference paths occupied by the gas.

The description of the propagation of beam 713 through interferometer system 769 and the generation of electrical interference signals, comprising heterodyne signal $s_3$ transmitted as signal 723 and heterodyne signals $s_{4A}$ and $s_{4B}$ transmitted as signal 724, is the same as corresponding portions of the description given for the first embodiment with respect to the propagation of beam 513 through interferometer 569 and the generation of electrical interference signals $s_1$ and $s_2$ transmitted as signals 523 and 524, respectively.

The descriptions of properties of heterodyne signals $s_3$ and $s_{4A}$ and respective phases $\phi_3$ and $\phi_{4A}$ are the same as the corresponding portions of the descriptions given for the properties of heterodyne signals $s_1$ and $s_2$ and respective phases $\phi_1$ and $\phi_2$ of the first embodiment. Further, equations for the second embodiment corresponding to Eqs. (1) through (23) for the first embodiment are obtained from Eqs. (1) through (23) by the replacement of all subscripts 1 with subscripts 3 and the replacement of all subscripts 2 with subscripts 4A. The corresponding equations are used to determine the dispersion of the gas in the at least one of the measurement and reference paths occupied by the gas and to determine the contribution of the gas to the relative path length of the measurement and reference paths.

The remaining heterodyne signals $s_{4A}$ and $s_{4B}$ and respective phases $\phi_{4A}$ and $\phi_{4B}$ are used to determine the cyclic errors in $\phi_{4A}$ and $\phi_{4B}$. One of the phases $\phi_{4A}$ or $\phi_{4B}$ after compensation for cyclic errors is used in a determination of the cyclic errors in $\phi_3$.

Signal 724 comprises heterodyne signals $s_{4A}$, $s_{4B}$, and two other heterodyne signals. Heterodyne signals $s_{4A}$ and $s_{4B}$ have heterodyne frequencies equal to frequency $f_{4A}$ and $f_{4B}$, respectively. The heterodyne frequencies for the two other heterodyne signals are $|\Delta f| \pm f_{4A}$ and $|\Delta f| \pm f_{4B}$, respectively, where $$\Delta f \equiv c\left(\frac{1}{\lambda_{4A}} - \frac{1}{\lambda_{4B}}\right) = \left(\frac{c}{\lambda_{4A}}\right)\left(\frac{\lambda_{4A}}{\lambda_{4B}} - 1\right) \tag{33}$$

and c is the speed of light in a vacuum. The apparatus and method of the second embodiment are operated such that $$|\Delta f| \gg |f_{4A}|, |f_{4B}|. \tag{34}$$

With the condition of Eq. (34) operative, the two other heterodyne signals, although they could be processed for additional information, are easily separated from heterodyne signals $s_{4A}$ and $s_{4B}$ and eliminated in detector 786 and/or in electronic processor 727 by electronic filtering.

The heterodyne signals $s_{4A}$ and $s_{4B}$ generated in detector 786 have the forms $$s_i = A_i(t)\cos[\alpha_i(t)], \; i=4A \text{ and } 4B. \tag{35}$$

The time-dependent arguments $\alpha_i(t)$ are given by $$\alpha_i(t) = 2\pi f_i t + \phi_i + \zeta_i + \Lambda_i, \; i=4A \text{ and } 4B, \tag{36}$$

where phase offsets $\zeta_i$ comprise all contributions to $\alpha_i$ that are not related or associated with the optical path of the measurement path 798 or reference path and not related or associated with nonlinear errors, and $\Lambda_i$ comprise the nonlinear errors including cyclic error effects. The description of the representations of $s_{4A}$ and $S_{4B}$ by Eqs. (35) is the same as the description given of the corresponding representations of $s_1$ and $s_2$ of the first embodiment by Eqs. (3). Heterodyne signals $s_{4A}$ and $s_{4B}$ are transmitted to electronic processor 727 for analysis as electronic signal 424 in either digital or analog format, preferably in digital format.

Referring now to FIG. 2b, electronic processor 727 comprises electronic processors 7274C and 7274D to determine measured phases $\phi_{4A}$ and $\phi_{4B}$, respectively, $$\phi_i\phi_i + \zeta_i + \Lambda_i(\phi_i), \; i=4A \text{ and } 4B, \tag{37}$$

using the phases of drivers 706A and 706B transmitted by signals 722A and 722B, respectively. Electronic processor 7277B subtracts $\phi_{4A}$ from $\phi_{4B}$ to form $\Phi_{104}$, i.e.

$$\Phi_\psi = (\phi_{4B} - \phi_{4A}). \tag{38}$$

Phase $\Phi_\psi$ may be expressed in terms of other quantities as $$\Phi_\psi = pk_{4A}(n_{4B}L_{4B} - n_{4A}L_{4A}) + pn_{4B}L_{4B}(2\pi\Delta f/c) + (\zeta_{4B} - \zeta_{4A}) + [\psi_{4B}(\phi_{4B}) - \psi_{4A}(\phi_{4A})], \tag{39}$$

where the non-linearity terms $\eta_{4A}$ and $\eta_{4B}$ have been omitted as per description given with respect to the first embodiment.

The effects of turbulence on the refractive index of the gas in the measuring path cancel out in $\Phi_\psi$ as well the effects of Doppler shifts produced by the translation of mirror 792 by translator 767. The turbulence effects on the refractive index of the gas in the measuring path cancel out in $\Phi_\psi$ because of the wavelength condition $|\lambda_{4A} - \lambda_{4B}| \ll \lambda_{4A}$ and because the measurement beam components of beam 737, components which are used in the generation of heterodyne signals $s_{4A}$ and $s_{4B}$, are derived from different frequency components of measurement beams which are substantially coextensive in measurement path 798. In addition, $L_{4A}$ and $L_{4B}$ can be made equal to a high level of accuracy.

Cyclic non-linearities $\psi_{4A}$ and $\psi_{4B}$ can to a high order of accuracy be written as $$\psi_{4A} = \sum_{r=1} a_{4A,r} \cos r\varphi_{4A} + \sum_{r=1} b_{4A,r} \sin r\varphi_{4A}, \tag{40}$$

$$\psi_{4B} = \sum_{r=1} a_{4B,r} \cos r\varphi_{4B} + \sum_{r=1} b_{4B,r} \sin r\varphi_{4B}.$$

Cyclic non-linearities $\psi_{4A}$ and $\psi_{4B}$ are written in Eqs. (40) in terms of cosine and sine series terms of harmonics of $\phi_{4A}$ and $\phi_{4B}$, respectively. For some configurations of interferometers, in particular multiple pass interferometers, it is possible for a system comprising a source, interferometer, and detector to generate cyclic nonlinearities that are subharmonics of $\phi_{4A}$ and/or $\phi_{4B}$. Should subharmonic cyclic errors be present in the system, Eqs. (40) are augmented so as to include cosine and sine series terms with arguments that are subharmonics of $\phi_{4A}$ and/or $\phi_{4B}$. The subsequent description of procedures to determine the coefficients in the cosine and sine series will be in terms of the series representations given by Eqs. (40) without departing from the spirit and scope of the present invention.

It is possible for a system comprising a source, interferometer, detector, and digital signal processing to generate cyclic non-linearities that are neither subharmonics or harmonics of $\phi_{4A}$ or $\phi_{4B}$. The non-subharmonic, non-harmonic cyclic errors are produced for example by aliasing in the digital signal processing and have frequencies which are aliases of harmonics and subharmonics of $\phi_{4A}$ and $\phi_{4B}$. Should non-subharmonic, nonharmonic cyclic errors be present in a system, Eqs. (40) are augmented so as to include cosine and sine series terms with arguments that are the appropriate aliases of harmonics and/or subharmonics of $\phi_{4A}$ and $(\phi_{4B}$. The subsequent description of procedures to determine the coefficients in the cosine and sine series will be in terms of the series representations given by Eqs. (40) without departing from the spirit and scope of the present invention.

The equation for cyclic nonlinearity $\psi_{4B}$ from Eqs. (40) may be rewritten in the form $$\psi_{4B} = \sum_{r=1} a_{4B,r}\cos r\,[\varphi_{4A} + pn_{4B}(2\pi\Delta f/c)L_{4B}] + \qquad (41)$$
$$\sum_{r=1} b_{4B,r}\sin r\,[\varphi_{4A} + pn_{4B}(2\pi\Delta f/c)L_{4B}]$$

noting that to a good approximation, $$\phi_{4B} = \phi_{4A} + pn_{4B}(2\pi\Delta f/c)L_{4B}. \qquad (42)$$

A term $pk_{4A}(L_{4B}n_{4B}-L_{4A}n_{4A})$ has been omitted in Eq. (42), this term being, for example, of the order of $10^{-4}$ radians for a $\Delta f=500$ Mhz, $L_{4B}=1$ m, and the gas comprised of air at room temperature and at atmospheric pressure. The terms in Eq. (41) may be expanded using trigonometric identities and rearranged according to the formula $$\psi_{4B} = \sum_{r=1} \cos r\varphi_{4A} \left\{ \begin{array}{l} a_{4B,r}\cos r[pn_{4B}(2\pi\Delta f/c)L_{4B}] + \\ b_{4B,r}\sin r[pn_{4B}(2\pi\Delta f/c)L_{4B}] \end{array} \right\} + \qquad (43)$$
$$\sum_{r=1} \sin r\varphi_{4A} \left\{ \begin{array}{l} -a_{4B,r}\sin r[pn_{4B}(2\pi\Delta f/c)L_{4B}] + \\ b_{4B,r}\cos r[pn_{4B}(2\pi\Delta f/c)L_{4B}] \end{array} \right\}.$$

In a next step, $\Phi_\psi$ is measured as a function $\phi_{4A}$ and for a set of values for $\Delta f$ [defined in Eq. (33)], the required number of different values of $\Delta f$ being dependent on the complexity of $\psi_{4B}$ and the precision required for the measured values of $\psi_{4B}$. From the measured values of $[\Phi_\psi - pn_{4B}L_{4B}(2\pi\Delta f/c)]$, measured values of the quantity $$\psi_{4B}(\phi_{4B}, \Delta f) - \psi_{4B}(\Phi_{4B}, \Delta f_0) \qquad (44)$$

are generated where $\Delta f_0$ is an initial value of $\Delta f$

The difference of cyclic errors $\psi_{4B}(\phi_{4B}, \Delta f) - \psi_{4B}(\Phi_{4B}, \Delta f_0)$ of Eq. (44) is written in terms of other quantities using Eq. (43) as $$\psi_{4B}(\varphi_{4B}, \Delta f) - \psi_{4B}(\varphi_{4B}, \Delta f_0) = \qquad (45)$$
$$\sum_{r=1} \cos r\varphi_{4A} \left( \begin{array}{l} a_{4B,r}\{\cos r[n_{4B}(2\pi\Delta f/c)L_{4B}] - \cos r[n_{4B}(2\pi\Delta f_0/c)L_{4B}]\} \\ b_{4B,r}\{\sin r[n_{4B}(2\pi\Delta f/c)L_{4B}] - \sin r[n_{4B}(2\pi\Delta f_0/c)L_{4B}]\} \end{array} \right) +$$
$$\sum_{r=1} \sin r\varphi_{4A} \left( \begin{array}{l} -a_{4B,r}\{\sin r[n_{4B}(2\pi\Delta f/c)L_{4B}] - \sin r[n_{4B}(2\pi\Delta f_0/c)L_{4B}]\} \\ b_{4B,r}\{\cos r[n_{4B}(2\pi\Delta f/c)L_{4B}] - \cos r[n_{4B}(2\pi\Delta f_0/c)L_{4B}]\} \end{array} \right).$$

The Fourier coefficients $a_{4A,r}$, $b_{4A,r}$, $a_{4B,r}$, and $b_{4B,r}$ can be determined by a procedure comprising a sequence of iterative procedures. The first step in the procedure is to obtain a first solution for $a_{4B,r}$ and $b_{4B,r}$, $r>1$, from an analysis of $\psi_{4B}(\phi_{4B}, \Delta f) - \psi_{4B}(\Phi_{4B}, \Delta f_0)$ The analysis comprises Fourier analyses of $\psi_{4B}(\phi_{4B}, \Delta f) - \psi_{4B}(\Phi_{4B}, \Delta f_0)$ wherein $\phi_{4A}$ is used as the variable of integration to yield values of the coefficients of $\cos r\phi_{4A}$ and $\sin r\phi_{4A}$ in Eq. (45) as functions of $\Delta f$. The values of coefficients of $\cos r\phi_{4A}$ and $\sin r\phi_{4A}$ in Eq. (45) generate a set of simultaneous equations in $a_{4B,r}$ and $b_{4B,r}$, $r<1$, and the set of simultaneous equations are solved for the first solution for $a_{4B,r}$ and $b_{4B,r}$, $r<1$. The absolute precision to which the first solution for $a_{4B,r}$ and $b_{4B,r}$, $r<1$, can be determined will have a magnitude of the order of magnitude of the product of the cyclic error term $|\psi_{4A}|/2$ expressed in radians and the cyclic error term $|\psi_{4B}|$ expressed in radians. The combined effect of cyclic error terms $|\psi_{4A}|$ and $|\psi_{4B}|$ enters as a second order effect in the absolute precision to which $\psi_{4B}$ can be determined.

The second step in the procedure is to generate a first iterated solution for $a_{4A,r}$ and $b_{4A,r}$, $r\geq 1$. The second step comprises iterated Fourier analyses of $[\Phi_\psi - pn_{4B}L_{4B}(2\pi\Delta f/c)]$ minus a $\psi_{4B}$ based on the first solution for $a_{4B,r}$ and $b_{4B,r}$, $r\leq 1$, wherein $\phi_{4B}$, corrected for a $\psi_{4B}$ based on the first solution for $a_{4B,r}$ and $b_{4B,r}$, $r\leq 1$, is used as the variable of integration in the iterated Fourier analyses.

The absolute precision to which the first solution iterated solution for $a_{4A,r}$ and $b_{4A,r}$ can be determined will have a magnitude of the order of magnitude of the product of the cyclic error term $|\psi_{4A}|$ expressed in radians and the absolute precision to which cyclic error term $|\psi_{4B}|$ expressed in radians is determined by the first solution for $a_{4B,r}$ and $b_{4B,r}$, $r\leq 1$. The combined effect of cyclic error terms $|\psi_{4A}|$ and $|\psi_{4B}|$ enters as a third order effect in the absolute precision to which $|\psi_{4A}|$ can be determined, second order in the magnitude of $|\psi_{4A}|$ expressed in radians and first order in the magnitude of $|\psi_{4B}|$ expressed in radians.

The third step in the procedure is obtain a second solution for $a_{4B,r}$ and $b_{4B,r}$, $r\geq 1$, from an analysis of $\psi_{4B}(\phi_{4B}, \Delta f) - \psi_{4B}(\Phi_{4B}, \Delta f_0)$. The third step is the same as the first step except that the variable of integration used in the Fourier analyses of the first step is replaced in the third step by $\phi_{4A}$ corrected for $\psi_{4A}$ based on the first iterated solution for $\psi_{4A}$. The absolute precision to which the second solution for $a_{4B,r}$ and $b_{4B,r}$, $r\leq 1$, can be determined will have a magnitude of the order of magnitude of the product the cyclic error term expressed in $|\psi_{4B}|$ expressed in radians and the absolute precision to which cyclic error term $|\psi_{4A}|$ expressed in radians is determined by the first iterated solution for $a_{4A,r}$ and $b_{4A,r}$, $r\leq 1$. The combined effect of cyclic error terms $|\psi_{4A}|$ and $|\psi_{4B}|$ enters as a fourth order effect in the absolute precision to which $\psi_{4A}$ can be determined, second order in the magnitude of $|\psi_{4A}|$ expressed in radians and second order in the magnitude of $|\psi_{4B}|$ expressed in radians.

The fourth step in the procedure is obtain a second iterated solution for $a_{4A,r}$ and $b_{4A,r}$, $r\geq 1$. The fourth step comprises iterated Fourier analyses of $[\Phi_\psi - pn_{4B}L_{4B}(2\pi\Delta f/c)]$ minus a $\psi_{4B}$ based on the second solution for $a_{4B,r}$ and $b_{4B,r}$, $r\leq 1$, wherein $\phi_{4B}$, corrected for a $\psi_{4B}$ based on the second solution for $a_{4A,r}$ and $b_{4A,r}$, $r\leq 1$, is used as the variable of integration in the iterated Fourier analyses. The fourth step is the same as the second step except for the variable of integration used in the respective Fourier analyses. The absolute precision to which the second iterated solution for $a_{4A,r}$ and $b_{4A,r}$, $r \leq 1$, can be determined will have a magnitude of the order of magnitude of the product the cyclic error term $|\psi_{4A}|$ expressed in radians and the absolute precision to which cyclic error term $|\psi_{4B}|$ expressed in radians is determined by the second solution for $a_{4A,r}$ and $b_{4A,r}$, $r \leq 1$. The combined effect of cyclic error terms $|\psi_{4A}|$ and $|\psi_{4B}|$ enters as a fifth order effect in the absolute precision to which $\psi_{4A}$ can be determined, third order in the magnitude of $|\psi_{4A}|$ expressed in radians and second order in the magnitude of $|\psi_{4BA}|$ expressed in radians.

The iterative process in the sequence of iterative procedures as described is continued until the Fourier coefficients $a_{4A,r}$, $b_{4A,r}$, $a_{4B,r}$, and $b_{4B,r}$, $r \geq 1$, are determined to requisite precision for an end use application. The iterative procedure of the iterative process should converge in several cycles to desired precision for $|\psi_{4A}| \leq \frac{1}{3}$ and $\psi_{4B} \leq \frac{1}{3}$.

The remaining description of the second embodiment is the same as corresponding portions of the description given for the first embodiment and variant thereof.

The advantages of the second embodiment are the same as listed for the seventh embodiment with the following additional advantage. With the second embodiment, the distance measuring function and the dispersion based system for compensating for gas in the measuring path, including turbulence effects in the gas, can be executed with two fixed wavelengths, $\lambda_3$ and $\lambda_{4A}$, simultaneous with and independent of the cyclic error compensating procedure based on the variable wavelength $\lambda_{4B}$ and one of the fixed wavelengths, either $\lambda_3$ or $\lambda_{4A}$.

The first and second embodiments and variant thereof used three different procedures for the measurement, monitoring, reduction, and/or compensation, in part or in whole, of the effects of the cyclic errors present in measured phases of heterodyne signals. Other forms of measurement, monitoring, reduction, and/or compensation, in part or in whole, for the effects of cyclic errors may be incorporated, as required by an end use application, into the apparatus of the present invention, as when working with stages commonly encountered in the lithographic fabrication of integrated circuits, without departing from the spirit or scope of the present invention. The other forms comprise methods and apparatus such as described in G. Wilkening and W. Hou, U.S. Pat. No. 5,331,400 entitled "Heterodyne Interferometer Arrangement" issued Jul. 19, 1994; in copending, commonly owned U.S. patent application with Ser. No. 09/168,200 by S. R. Paterson, V. G. Bagdami, and C. A. Zanoni entitled "Interferometry System Having Reduced Cyclic Errors" filed Oct. 6, 1998; and in copending, commonly owned U.S. patent application with Ser. No. 09/268, 619by H. A. Hill entitled "Systems and Methods For Characterizing Cyclic Errors In Distance Measuring and Dispersion Interferometry" filed Mar. 5, 1999. The contents of the two copending applications are incorporated herein by reference in their entirety.

The descriptions of the first and second embodiments and variant thereof noted that the configurations of interferometers illustrated in FIGS. 1a and 2a are known in the art as polarized Michelson interferometers known in the art as. Other forms of the Michelson interferometer and forms of other interferometers such as the high stability plane mirror interferometer, or the differential plane mirror interferometer, or the angle-compensating interferometer or similar device such as is described in an article entitled "Differential interferometer arrangements for distance and angle measurements: Principles, advantages and applications" by C. Zanoni, *VDI Berichte Nr.* 749, 93–106 (1989), may be incorporated into the apparatus of the present invention as when working with stages commonly encountered in the lithographic fabrication of integrated circuits without departing from the spirit or scope of the present invention. The foregoing article is incorporated herein by reference.

FIGS. 3a–3f depict in diagrammatic form a third preferred embodiment of the present invention. The third embodiment comprises apparatus and methods for measuring the relative physical path length of a measurement path and reference path. A multiple optical pass system configuration of interferometers is used to reduce Doppler shift effects in dispersion related signals. Effects of gas in at least one of a measurement path and a reference path of a linear displacement interferometer are measured and compensated. Further, the effects of cyclic errors are measured and compensated in both the measured phase used for determination of the relative physical path length of the measurement and reference paths and the associated optical dispersion related signal used to correct the relative optical path length for effects of gas in the at least one of the measurement and reference paths. Either or both the refractive index of the gas and the relative physical length of the measurement and reference paths may be changing.

Figure 3A:
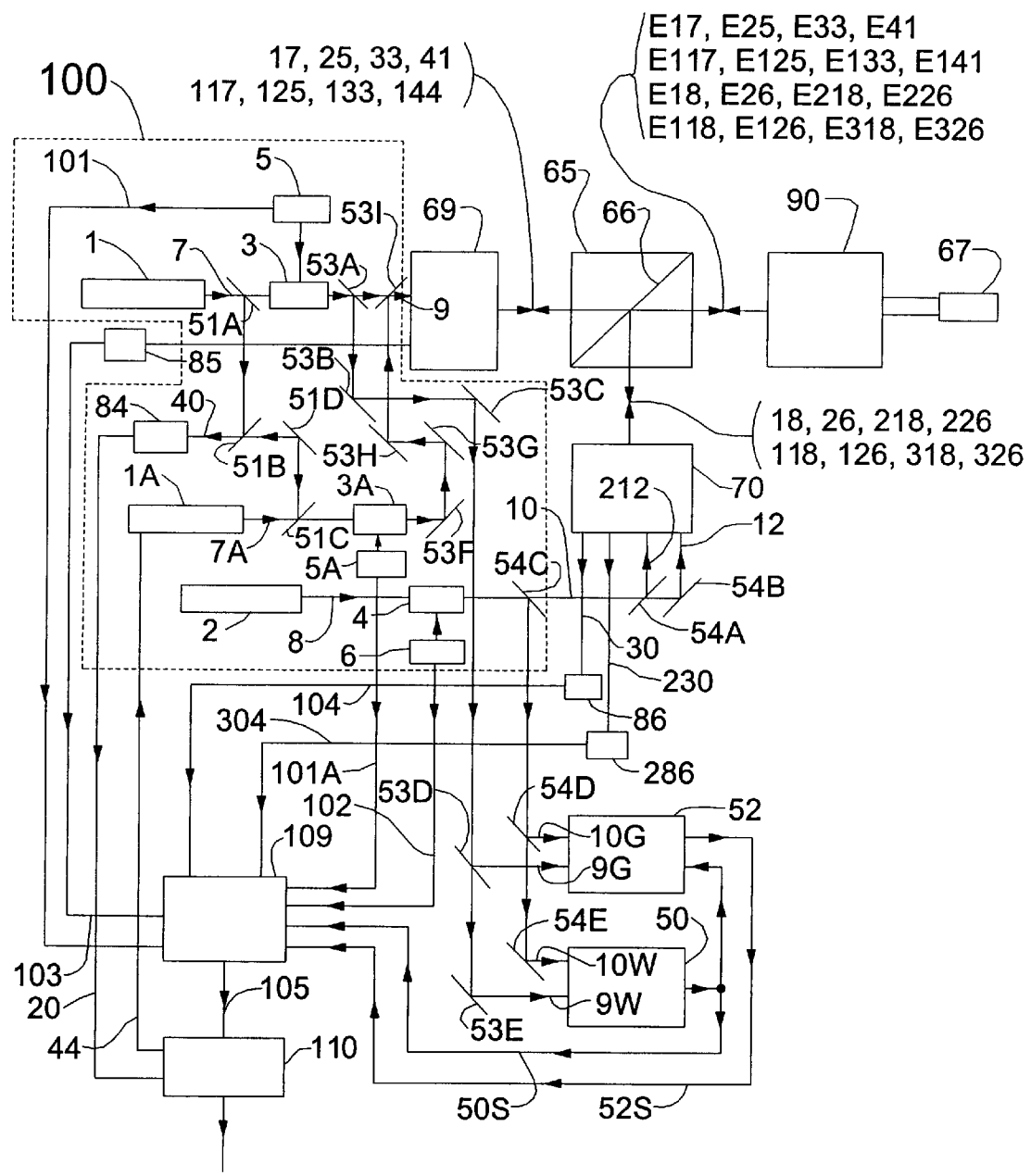
FIGS. 3a–3e depict in diagrammatic form a third preferred embodiment of the present invention for measuring the relative physical path length of a measurement path and reference path using a multiple optical pass system configuration to reduce Doppler shift effects in dispersion related signals.

The interferometry system of the third embodiment comprises, as shown in FIG. 3a, a source system 100, interferometer 69 and interferometer group 70, detectors 85, 86, and 286, wavelength monitors 50 and 84, a Γ monitor 52, an electronic processor 109, and a computer and controller 110. The configurations of interferometer 69 and the interferometers comprising interferometer group 70 are known in the art as differential plane mirror interferometers.

The source system of the third embodiment generates light beams 9 and 10. Many elements of source system 100 shown in FIG. 3a perform like functions as do like elements of source system 500 of the first embodiment shown in FIG. 1a. Unless indicated otherwise, the number of an element of source system 100 performing a like function as an element of source system 500 of the first embodiment is equal to the number of the element of the first embodiment shown in FIG. 1a decremented by 500. The descriptions of sources 1 and 2 are the same as corresponding portions of the descriptions given for sources 501 and 502, respectively, of the first embodiment. The description of source 1A is the same as corresponding portions of the description given for source 1 of the first embodiment except that the wavelength of source 1A is not fixed. Sources 1, 1A, and 2 generate beams 7, 7A, and 8, respectively, with wavelengths $\lambda_5$, $\lambda_{5A}$, and $\lambda_6$, respectively. Beams 7, 7A, and 8 are polarized in the plane of FIG. 3a.

The ratio of the wavelengths ($\lambda_5/\lambda_6$) has a known approximate ratio value $l_5/l_6$, i.e.

$$(\lambda_5/\lambda_6) \cong (l_5/l_6), \quad (46)$$

where $l_5$ and $l_6$ comprise low order nonzero integer values or at least one non-integer nonzero value having a low order of magnitude.

Wavelength $\lambda_{5A}$ of the beam from source 1A is controlled by error signal 44 from computer and controller 110. For the third embodiment, $(\lambda_5-\lambda_{5A})>0$ and $|\lambda_5-\lambda_{5A}|<<\lambda_5$ in order to illustrate in a simple manner the present invention. The third embodiment may be configured to be operative for negative values for $(\lambda_5-\lambda_{5A})$ and/or for $|\lambda_5-\lambda_{5A}|<<\lambda_5$ without departing from the scope and spirit of the present invention. For configurations of the apparatus of the third embodiment where the condition $|\lambda_5-\lambda_{5A}|<<\lambda_5$ is not applicable, it may be desirable to change certain of the non-polarizing beam splitters described for the third embodiment to dichroic beam splitters to improve overall efficiency of the source system and interferometer system.

As shown in FIG. 3a, a first portion of beam 7 is reflected by non-polarizing beam splitter 51A and a portion thereof reflected by a non-polarizing beam splitter 51B to form a first component of beam 40. In a next step, a first portion of beam 7A is reflected by non-polarizing beam splitter 51C, reflected by mirror 51D, and a portion thereof transmitted by non-polarizing beam splitter 51B to form a second component of beam 40. Beam 40 impinges on wavelength monitor 84 configured to monitor the ratio ($\lambda_5/\lambda_{5A}$). The measured value of the ratio ($\lambda_5/\lambda_{5A}$) is transmitted to computer and controller 110 as electronic signal 20. Wavelength monitor 84 may comprise, or example, a photodetector for generating an electrical interference signal from the mixed beam 40, interferometers with or without a vacuum in a measurement leg and/or nonlinear elements such as $\beta$-BaBO$_3$ to double the frequency of a beam by second harmonic generation, SHG.

Computer and controller 110 generates error signal 44 related to the difference between the measured value of wavelength ratio ($\lambda_5/\lambda_{5A}$) the ratio transmitted by signal 20, and a ratio specified by computer and controller 110. The wavelength of source 1A is controlled by error signal 44. Error signal 44 may control, for example, the wavelength of a laser by controlling the length of the laser cavity with a piezoelectric transducer or the wavelength of a diode laser by controlling the injection current of the diode laser.

Continuing with FIG. 3a, a first portion of the beam exiting modulator 3 is transmitted by non-polarizing beam splitter 53A and a portion thereof transmitted as a $\lambda_5$ component of beam 9. A second portion of the beam exiting modulator 3 is reflected by non-polarizing beam splitter 53A, reflected by mirrors 53B and 53C, and a portion thereof reflected by non-polarizing beam splitter 53D as beam 9G. A second portion of the beam incident on non-polarizing beam splitter 53D is transmitted and then reflected by mirror 53E as beam 9W. Beams 9G and 9W have wavelengths $\lambda_5$. The beam exiting modulator 3A is reflected by mirrors 53F, 53G, and 53H and a portion hereof reflected by non-polarizing beam splitter 53I as a $\lambda_5$ component of beam 9.

As shown in FIG. 3a, a first portion of the beam exiting modulator 4 is transmitted by non-polarizing beam splitter 54C as beam 10. A second portion of the beam exiting modulator 4 is reflected by non-polarizing beam splitter 54C and a portion thereof reflected by non-polarizing beam splitter 54D as beam 10G. A second portion of the beam incident on non-polarizing beam splitter 54D is transmitted by non-polarizing beam splitter 54D and then reflected by mirror 54E as beam 10W. Beams 10G and 10W have wavelengths $\lambda_6$.

In a next step, a first portion of beam 10 is reflected by a non-polarizing beam splitter 54A as beam 212. A second portion of beam 10 is transmitted by non-polarizing beam splitter 54A and a portion thereof reflected by non-polarizing beam splitter 54B as beam 12. Beam 9 is incident on differential plane mirror interferometer 69 and beams 12 and 212 are incident on differential plane mirror interferometer group 70 comprising two differential plane mirror interferometers. Differential plane mirror interferometer 69 and differential plane mirror interferometer group 70 with beam splitter 65 and external mirrors furnished by external mirror system 90 comprise means for introducing a phase shift $\phi_5$ between the x and y components of beam 9 having wavelength $\lambda_5$, a phase shift $\phi_{5A}$ between the x and y components of beam 9 having wavelength $\lambda_{5A}$, a phase shift $\phi_6$ between the x and y components of beam 12 having wavelength $\lambda_6$, and a phase shift $\phi_7$ between the x and y components of beam 212 having wavelength $\lambda_6$.

Figure 3B:
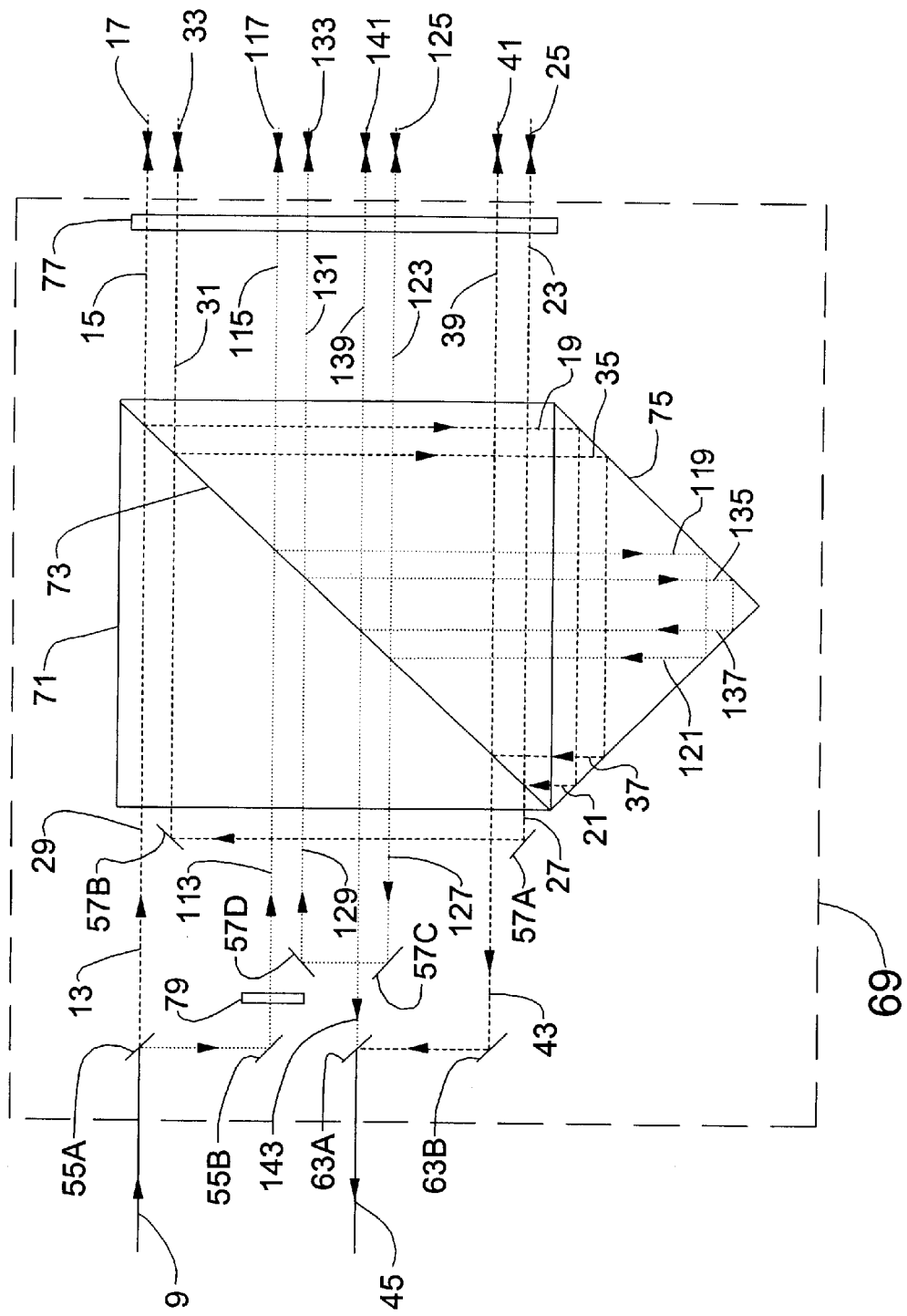

A differential plane mirror interferometer measures the optical path changes between two external plane mirrors. In addition, it is insensitive to thermal and mechanical disturbances that may occur in interferometer beam splitting cube and associated optical components. Differential plane mirror interferometer 69 as shown in FIG. 3b has eight exit/return beams 17, 25, 33, 41, 117, 125, 133, and 141. Beams 17, 25, 33, and 41 originating from one polarization component of beam 9, the first polarization component, comprise beams for a reference leg. Beams 117, 125, 133, and 141 originating from a second polarization component of beam 9 comprise beams for a measurement leg. Beams for which the first polarization component of beam 9 is the sole progenitor are indicated in FIG. 3b by dashed lines and beams for which the second polarization component of beam 9 is the sole progenitor are indicated in FIG. 3b by dotted lines.

Figure 3C:
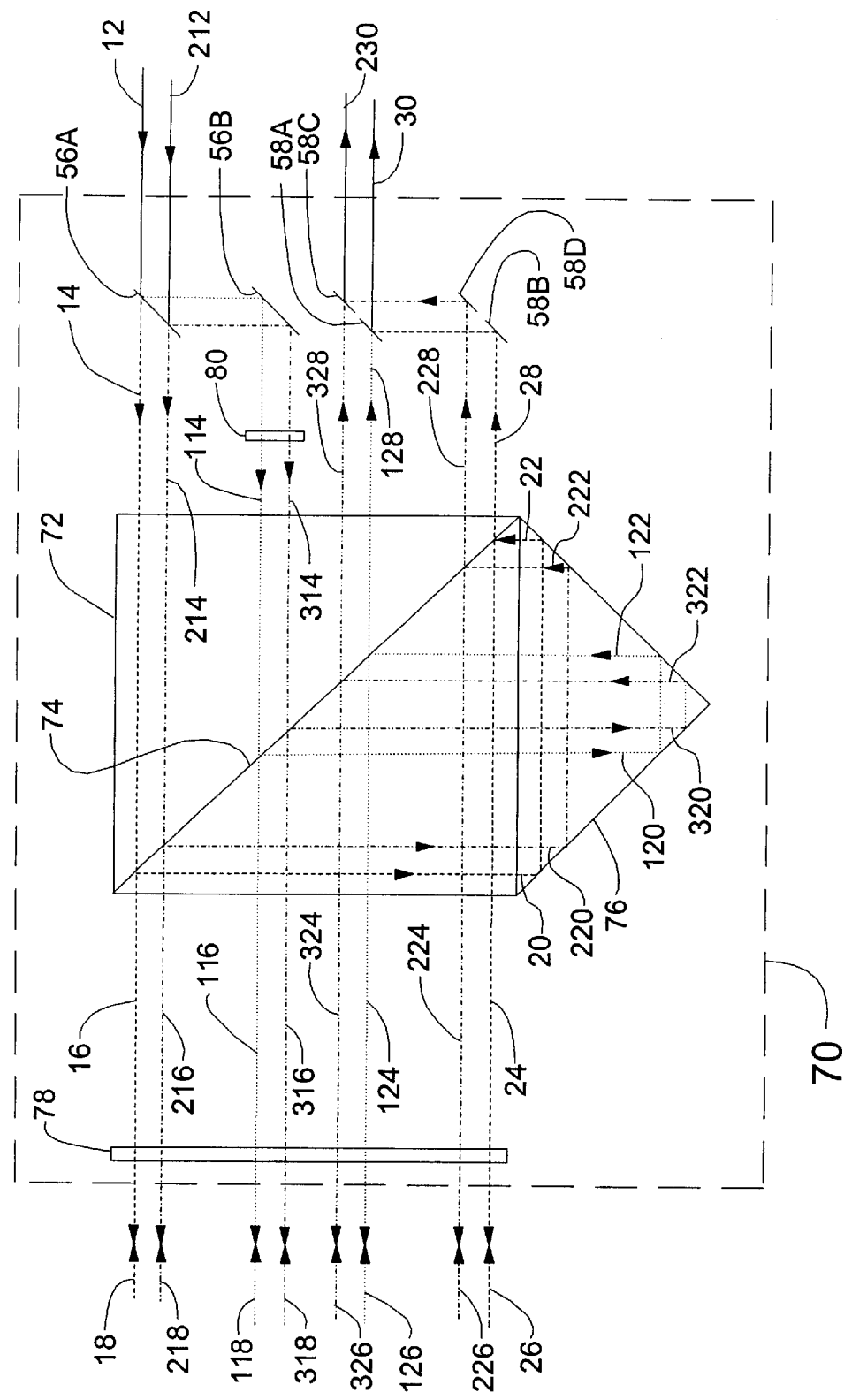

One differential plane mirror interferometer of differential plane mirror interferometer group 70 has four exit/return beams 18, 26, 118, and 126. Beams 18 and 26 originating from one polarization component, a first polarization component, of beam 12 comprise beams for a reference leg. Beams 118 and 126 originating from a second polarization component of beam 12 comprise beams for a measurement leg. Beams for which the first polarization component of beam 12 is the sole progenitor are indicated in FIG. 3c by dashed lines and beams for which the second polarization component of beam 12 is the sole progenitor are indicated in FIG. 3c by dotted lines. second differential plane mirror interferometer of differential plane mirror interferometer group 70 has four exit/return beams 218, 226, 318, and 326. Beams 218 and 226 originating from one polarization component, a first polarization component, of beam 212 comprise beams for a reference leg. Beams 318 and 326 originating from a second polarization component of beam 212 comprise beams for a measurement leg. Beams for which the first polarization component of beam 212 is the sole progenitor are indicated in FIG. 3c by lines comprised of alternating dots and dashes and beams for which the second polarization component of beam 212 is the sole progenitor are indicated in FIG. 3c by lines comprised of alternating dot pairs and dashes.

Beams 17, 25, 33, 41, 117, 125, 133, and 141 are incident on beam splitter 65 and are transmitted by dichroic beam splitter interface 66 as beams E17, E25, E33, E41, E117, E125, E133, and E141, respectively. Beams E17, E25, E33, E41, E117, E125, E133, and E141 are incident on external mirror system 90, illustrated in FIG. 1d, which results in beams 43 and 143. Beam 143 contains information at wavelengths $\lambda_5$ and $\lambda_{5A}$ about the optical path lengths through the gas in measuring path of external mirror system 90 and beam 43 contains information at wavelengths $\lambda_5$ and $\lambda_{5A}$ about the optical path lengths through a reference path. Likewise, beams 18, 26, 118, 126, 218, 226, 318, and 326 are incident on beam splitter 65 and reflected by dichroic beam splitter interface 66 as beams E18, E26, E118, E126, E218, E226, E318, and E326, respectively. Beams E18, E26, E118, E126, E218, E226, E318, and E326 are incident on external mirror system 90, illustrated in FIG. 3e, which results in beams 28, 128, 228, and 328, respectively. Beams 128 and 328 contain information at wavelength $\lambda_6$ about optical path lengths through the gas in respective measuring paths of external mirror system 90 and beams 28 and 128 contain information at wavelength $\lambda_6$ about optical path lengths through respective reference paths.

Beam 43 is reflected by mirror 63B and a portion thereof is reflected by non-polarizing beam splitter 63A to become one component of beam 45. A portion of beam 143 is transmitted by beam splitter 63A to become a second component of beam 45. Beam 45 is a mixed beam, the first and second components of beam 45 having the same linear polarizations. Beam 45 exits differential plane mirror interferometer 69.

Beam 28 is reflected by mirror 58B and a portion thereof is reflected by non-polarizing beam splitter 58A to become a first component of beam 30. A portion of beam 128 is transmitted by beam splitter 58A to become a second component of beam 30. Beam 30 is a mixed beam, the first and second components of beam 30 having the same linear polarizations.

Beam 228 is reflected by mirror 58D and a portion thereof is reflected by non-polarizing beam splitter 58C to become a first component of beam 230. A portion of beam 328 is transmitted by beam splitter 58C to become a second component of beam 230. Beam 230 is a mixed beam, the first and second components of beam 230 having the same linear polarizations. Beams 30 and 230 exit differential plane mirror interferometer group 70.

The magnitude of phase shifts $\phi_5$, $\phi_{5A}$, $\phi_6$, and $\phi_7$ are related to the difference $L_i$ between the round-trip physical length of path i of measurement path 98 and of reference paths, shown in FIGS. 3a–3e for the case of $p_1=2p_2$, according to the formulae $$\varphi_5(t) = \sum_{i=1}^{i=p_1} \varphi_{5,i}(t_i) = \sum_{i=1}^{i=p_1} L_i(t_i) k_5 n_{5,i},$$

$$\varphi_{5A}(t) = \sum_{i=1}^{i=p_1} \varphi_{5A,i}(t_i) = \sum_{i=1}^{i=p_1} L_i(t_i) k_{5A} n_{5A,i},$$

$$\varphi_6(t) = \sum_{i=1}^{i=p_2} \varphi_{6,i}(t_i) = \sum_{i=1}^{i=p_2} L_i(t_i) k_6 n_{6,i},$$

$$\varphi_7(t) = \sum_{i=p_2+1}^{i=p_1} \varphi_{7,i}(t_i) = \sum_{i=p_2+1}^{i=p_1} L_i(t_i) k_7 n_{7,i}, \quad (47)$$

where $n_{m,i}$ are the refractive indices of gas in path i of measurement path 98 corresponding to wavenumber $k_i=(2\pi)/\lambda_i$. The nominal value for $L_i$ corresponds to twice the spatial separation of mirror surfaces 95 and 96 in external mirror system 90 (see FIGS. 3d and 3e). To those skilled in the art, the generalization to case when $p_1 \neq 2p_2$ is a straight forward procedure. In FIGS. 3b–3e, differential plane mirror interferometer 69 and differential plane mirror interferometers of differential plane mirror group 70 are configured so that $p_1=4$ and $p_1=2$, respectively, so as to illustrate in the simplest manner a function of the apparatus of the first preferred embodiment of the present invention regarding the use of multiple pass configurations to reduce Doppler shift effects in dispersion related signals.

Eqs. (47) are valid for the case where the combined paths for wavelength $\lambda_5$ and the combined paths for wavelength $\lambda_6$ are substantially coextensive. To those skilled in the art, the generalization to the case where the respective combined paths for the two different wavelengths are not substantially coextensive is a straight forward procedure.

The average time delay for a light beam to travel from a first reflection by mirror 92 of external mirror system 90 to the point where the respective measurement and reference beams are mixed will in general be different for light beams of the shorter wavelength $\lambda_6$ and light beams of a longer wavelengths, either $\lambda_5$ or $\lambda_{5A}$. The difference in time delays arise because the number of multiple passes for a light beam with the shorter wavelength is different from the number of multiple passes for a light beam with the longer wavelength. The effect of the differences in the average time delay for light beams of the shorter and longer wavelengths has been omitted in Eqs. (47) so as to not unduly complicate the description of the third embodiment.

The effect of the differences in the average time delay for light beams of the shorter and longer wavelengths on the differences of respective phases is a higher order effect, the effect being proportional to the speed of mirror 92 of external mirror system 90, to approximately the instantaneous average value for $L_i$, and to respective heterodyne frequencies. For a speed of motion for mirror 92 of 2 m/s, a instantaneous average value of $L_i$ of 2 m, and a heterodyne frequency of 20 MHz, the differences of respective phases is approximately 1 radian and the rate of change of the difference is approximately 1 radian/sec. Changes in such phase differences occur at low frequencies, typically less than or of the order of 10 Hz. It will be apparent to those skilled in the art that such phase differences, the effect of the differences in the average time delay for light beams of the shorter and longer wavelengths, can be modeled and compensated with knowledge of the speed of mirror 92 and the approximate instantaneous average value for $L_i$ in subsequent signal processing to a required precision imposed on the output data by the final end use application.

In a next step as shown in FIG. 3a, beam 45 impinges on detector 85 resulting in heterodyne signals $s_5$ and $s_{5A}$ and two other heterodyne signals and beams 30 and 230 impinge upon photodetectors 86 and 286, respectively, resulting in two interference signals, heterodyne signals $s_6$ and $s_7$, respectively, preferably by photoelectric detection. Signals $s_5$ and $s_{5A}$ correspond to wavelengths $\lambda_5$ and $\lambda_{5A}$, respectively, and signals $s_6$ and $s_7$ correspond to wavelength $\lambda_6$.

Heterodyne signals $s_5$ and $s_{5A}$ have heterodyne frequencies equal to frequency $f_5$ and $f_{5A}$, respectively. The heterodyne frequencies for the two other heterodyne signals are $|\Delta f| \pm f_5$ and $|\Delta f| \pm f_{5A}$, respectively, where $$\Delta f \equiv c\left(\frac{1}{\lambda_5} - \frac{1}{\lambda_{5A}}\right) = \left(\frac{c}{\lambda_5}\right)\left(\frac{\lambda_5}{\lambda_{5A}} - 1\right) \quad (48)$$

and c is the speed of light in a vacuum. The apparatus and method of the third embodiment are operated such that $$|\Delta f| >> |f_5|, |f_{5A}| \quad (49)$$

With the condition of Eq. (49) operative, the two other heterodyne signals, although they could be processed for additional information, are easily separated from heterodyne signals $s_5$ and $s_{5A}$ and eliminated in detector and/or in subsequent signal processing in electronic processor 109 by electronic filtering.

Signals $s_i$ have the form $$s_i = A_i \cos[\alpha_i(t)], \quad i=5,5A, 6, \text{ and } 7, \quad (50)$$

where the time-dependent arguments $\alpha_i(t)$ are given by $$\alpha_5(t) = 2\pi f_5 t + \tilde{\phi}_5,$$

$$\alpha_{5A}(t) = 2\pi f_{5A} t + \tilde{\phi}_{5A},$$

$$\alpha_6(t) = 2\pi f_6 t + \tilde{\phi}_6,$$

$$\alpha_7(t) = 2\pi f_6 t + \tilde{\phi}_7, \quad (51)$$

with $$\phi_5 = \tilde{\phi}_5 + \Lambda_5 + \zeta_5,$$

$$\phi_{5A} = \tilde{\phi}_{5A} + \Lambda_{5A} + \zeta_{5A},$$

$$\phi_6 = \tilde{\phi}_6 + \Lambda_6 + \zeta_6,$$

$$\phi_7 = \tilde{\phi}_7 + \Lambda_7 + \zeta_7, \quad (52)$$

phase offsets $\zeta_i$ comprising all contributions to the phase shifts $\phi_i$ that are not related to the measurement path 98 or reference paths, and the $\Lambda_i$ comprising cyclic error terms. The description of the representations of $s_5$, $s_{5A}$, $s_6$, and $s_7$ by Eqs. (50) is the same as the description given of the corresponding representations of $s_1$ and $s_2$ of the first embodiment by Eqs. (50). Heterodyne signals $s_5$ and $s_{5A}$ are transmitted as electronic signal 103 and heterodyne signals $s_6$ and $s_7$ are transmitted as electronic signals 104, and 304, respectively, to electronic processor 109 for analysis in either digital or analog format, preferably in digital format.

Heterodyne signals $s_5$ and $s_{5A}$ are processed by electronic processor 109 and computer and controller 110 to measure and monitor the cyclic error contributions to measured phases $\phi_5$ and $\phi_{5A}$ respectively. The description of processing and procedure for the determination of the cyclic errors in $\phi_5$ and $\phi_{5A}$ of the third embodiment is the same as corresponding portions of the description given for the determination of the cyclic errors in $\phi_{4A}$ and $\phi_{4B}$ of the second embodiment.

The next step in the determination of cyclic errors is the determination of cyclic errors in measured phases $\phi_6$ and $\phi_7$. The cyclic errors in measured phases $\phi_6$ and $\phi_7$ are obtained by Fourier analyses of $\phi_6$ and $\phi_7$, respectively, using as the variable of integration $\phi_5$ corrected for cyclic errors by the preceding procedure or $\phi_{5A}$ corrected for cyclic errors by the preceding procedure. The description of the subsequent step in the determination of cyclic errors is the same as corresponding portions of the description given for the second embodiment.

Heterodyne signals $s_5$, $s_6$, and $s_7$ are processed by electronic processor 109 and computer and controller 110 to measure and monitor changes in a physical length that are insensitive to the effects of a gas in the at least one of the measurement and reference paths.

A preferred method for electronically processing the heterodyne signals $s_5$, $s_6$, and $s_7$ is presented herewithin for the case when $l_5$ and/or $l_6$ are not low order integers. For the case when $l_5$ and $l_6$ are both low order integers and the ratio of the wavelengths matched to the ratio ($l_5/l_6$) with a relative precision sufficient to meet a certain required precision imposed on the output data by an end use application, the preferred procedure for electronically processing the heterodyne signals $s_5$, $s_6$, and $s_7$ is the same as the one subsequently set down for the second variant of the third embodiment of the present invention.

Figure 3D:
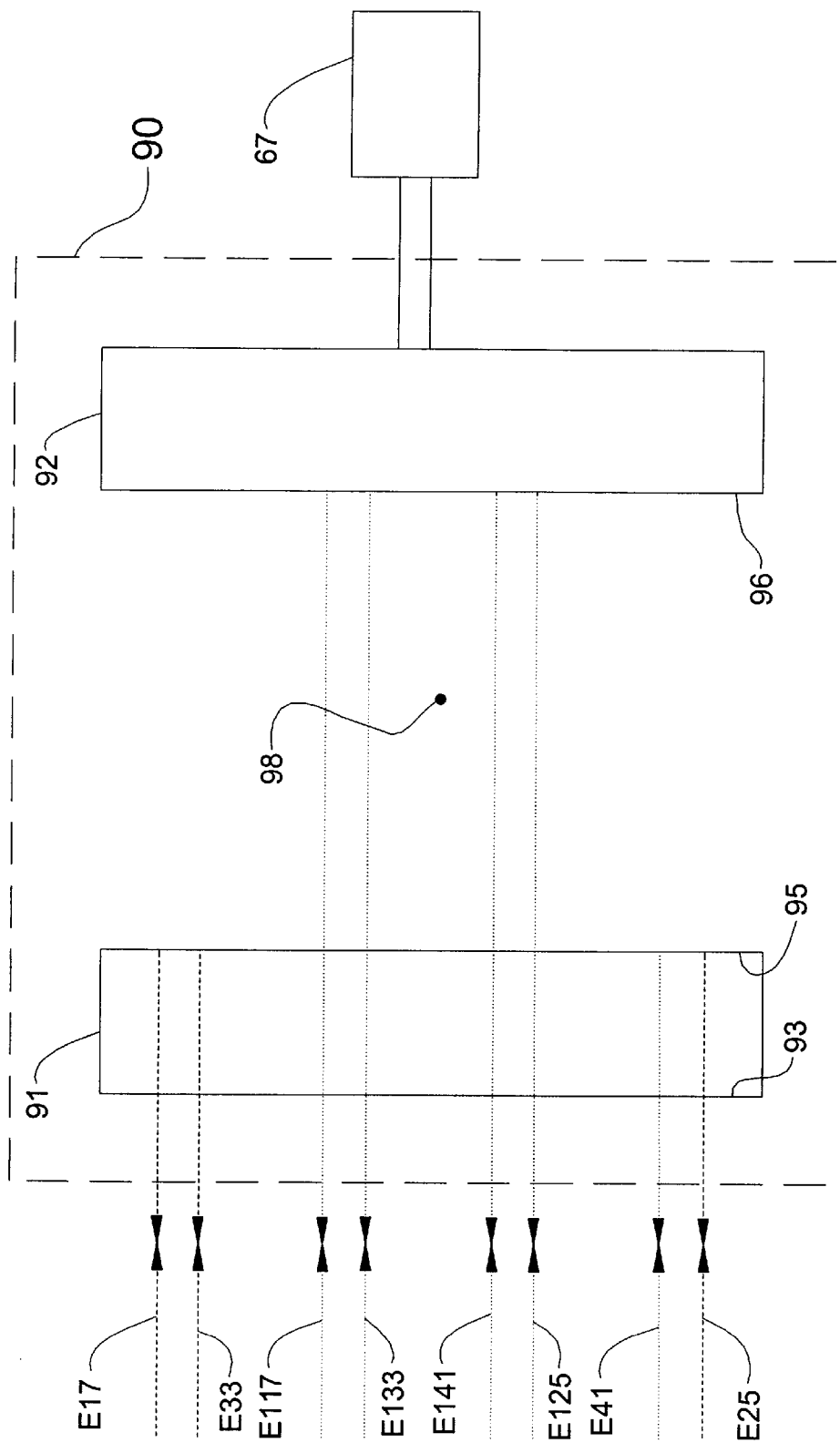
Figure 3E:
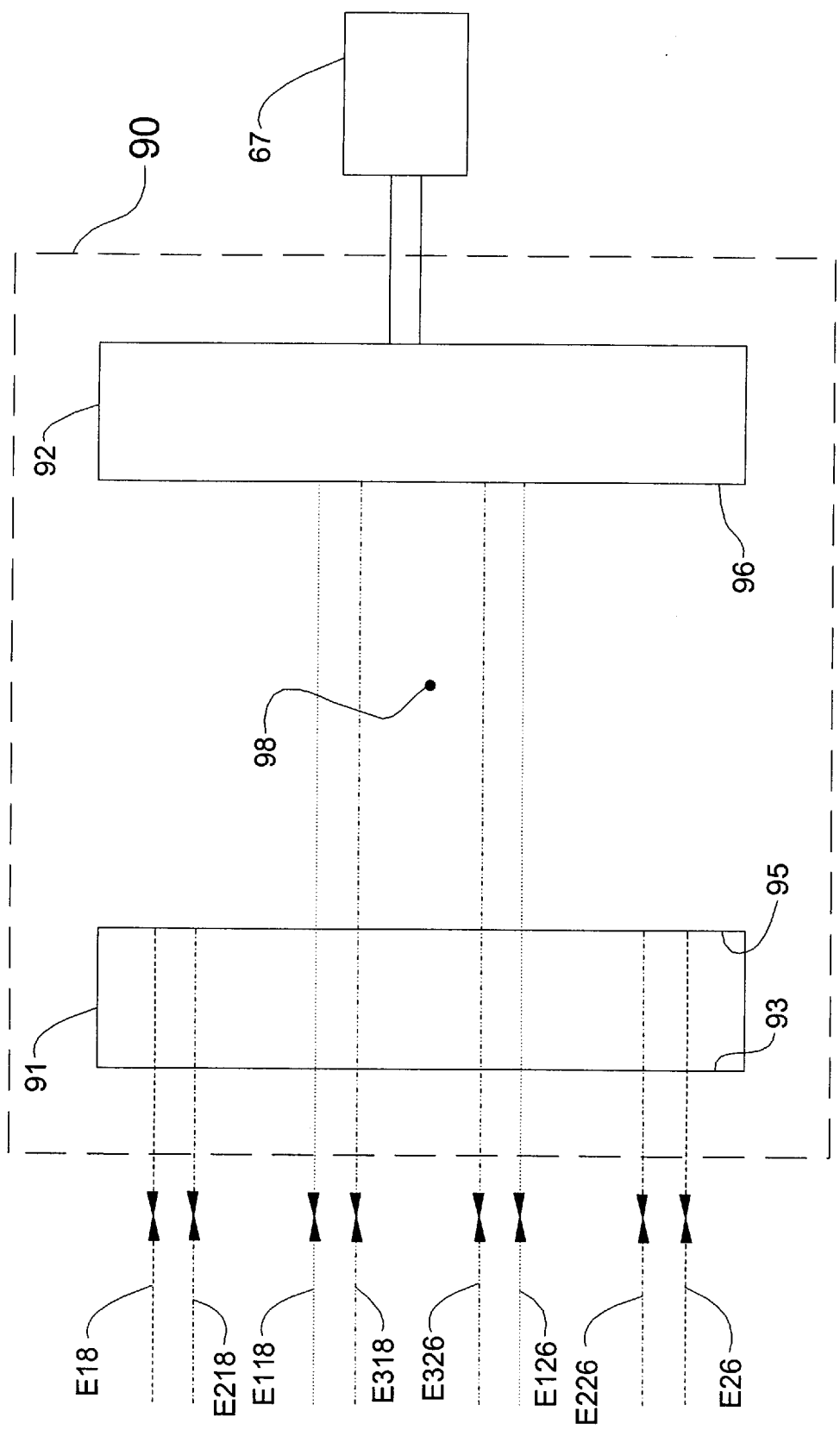
Figure 3F:
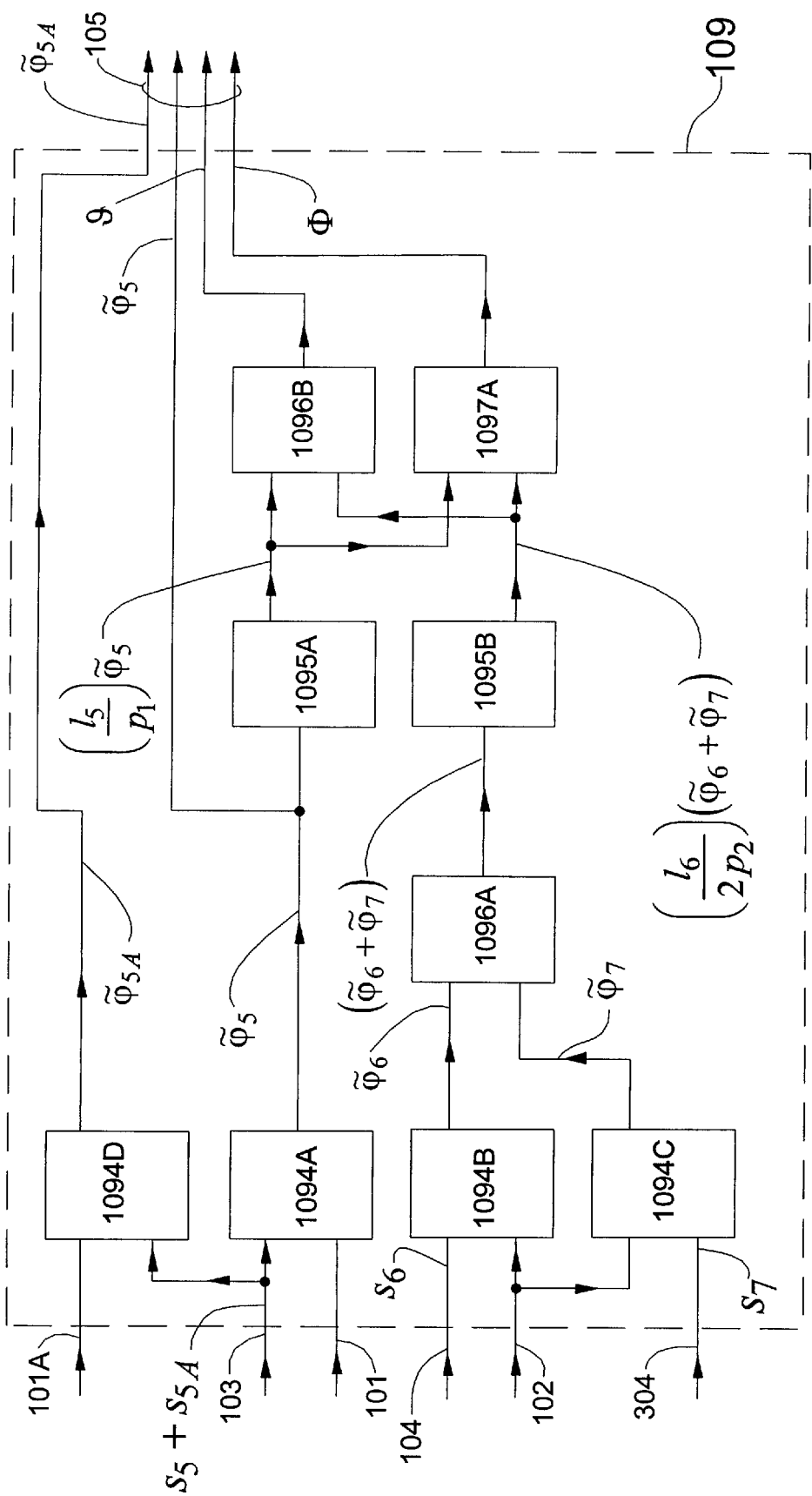

Referring now to FIG. 3f, electronic processor 109 comprises electronic processors 1094A, 1094B, 1094C and 1094D to determine the phases $\phi_5$, $\phi_6$, $\phi_7$, and $\phi_{5A}$ respectively, by either digital or analog signal processes, preferably digital processes, using time-based phase detection such as a digital Hilbert transform phase detector [see R. E. Best, ibid.] or the like and the phase of drivers 5, 5A, and 6.

The phases of drivers 5, 5A, and 6 are transmitted by electrical signals, reference signals 101, 101A, and 102, respectively, in either digital or analog format, preferably in digital format, to electronic processor 109. Reference signals, alternatives to reference signals 101, 101A, and 102, may also be generated by an optical pick off means and detectors (not shown in figures) by splitting off portions of beams 9 and 10 with beam splitters, preferably nonpolarizing beam splitters, mixing the portion of the beam 9 and the portion of the beam 10 that are split off, and detecting the mixed portions to produce heterodyne reference signals.

Referring again to FIG. 3f, electronic processor 109 comprises electronic processors 1096A add together $\phi_6$ and $\phi_7$. Next, the phase $\phi_5$ and the resulting phase sum ($\phi_6+\phi_7$) are multiplied by $l_5/p_1$ and $(l_6/p_2)(\frac{1}{2})$, respectively, in electronic processors 1095A and 1095B, respectively, preferably by digital processing, resulting in phases $(l_5/p_1)\phi_5$ and $(l_6/p_2)(\phi_6+\phi_7)/2$. The phases $(l_5/p_1)\phi_5$ and $(l_6/p_2)(\phi_6+\phi_7)/2$ are next added together in electronic processor 1096B and subtracted one from the other in electronic processor 1097A, preferably by digital processes, to create the phases $\Theta$ and $\Phi$, respectively. Formally, $$\vartheta = \left[\frac{l_5}{p_1}\tilde{\varphi}_5 + \frac{l_6}{p_2}\frac{(\tilde{\varphi}_6+\tilde{\varphi}_7)}{2}\right], \quad (53)$$

$$\Phi = \left[\frac{l_5}{p_1}\tilde{\varphi}_5 - \frac{l_6}{p_2}\frac{(\tilde{\varphi}_6+\tilde{\varphi}_7)}{2}\right]. \quad (54)$$

Note from Eqs. (53) and (54) that $\Theta$ and $\Phi$ are not sensitive to tilt and/or yaw of either mirror 91 or 92 of external mirror system 90, except for instantaneous changing of tilt and/or yaw of either mirror 91 or 92 of external mirror system 90 through the effect of the differences in the average time delay for light beams of differing wavelengths [see Eq. 46] and insensitive to thermal and mechanical disturbances that may occur in the interferometer beam splitting cubes and associated optical components as a consequence of the use of differential plane mirror interferometers.

The phase effects in $\Theta$ and $\Phi$ resulting from instantaneous changing of tilt and/or yaw of either mirror 91 or 92 through the effect of the differences in the average time delay for light beams of differing wavelengths are higher order effects, the effects being proportional to the instantaneous angular velocity in either tilt or yaw, the separation of beams incident on the mirror changing in tilt and/or yaw, and heterodyne frequencies and occur at low frequencies, typically less than or of the order of 10 Hz. The phase effects in $\Theta$ and $\Phi$ resulting from instantaneous changing of tilt and/or yaw at an angular velocity of $2\pi/10$ radians/sec of either mirror 91 or 92 through the effect of the differences in the average time delay for light beams of differing wavelengths with a heterodyne frequency of 20 MHz are approximately 0.6 radian/sec. It will be apparent to those skilled in the art that the phase effects in $\Theta$ and $\Phi$ resulting from instantaneous changing of tilt and/or yaw of either mirror 91 or 92 can be modeled and compensated, with knowledge of the instantaneous tilt and/or yaw angular velocities of mirror 91 or 92 and the approximate instantaneous average value for $L_i$, in subsequent signal processing to the required precision imposed on the output data by the final end use application.

Group delay effects may need to be taken into consideration. For a measuring path comprised of a vacuum, phase $\Phi$ should substantially be a constant independent of Doppler shifts due to a motion of one or both of the mirrors in the external mirror system 90, that motion which changes the mirror separation. This may not be the case in practice due to differences in the group delay experienced by the electrical signals $s_5$, $s_6$, and $s_7$. If phase $\Phi$ is not a constant for a measuring path comprised of a vacuum, techniques known to those skilled in the art can be used to compensate for departures of phase $\Phi$ from a constant (cf. Blinchikoff and Zveriv, ibid.).

It is important to note that the group delay effects in $\Phi$ can not only be detected but can also be determined for a measuring path comprising a vacuum by measuring $\Phi$ as a function of different translational velocities of mirror 92 produced by translator 67. It is also important to note that the group delay effects in $\Phi$ can be significantly reduced by performing analog-to-digital conversion of signals $s_5$, $s_{5A}$, $S_6$, and $s_7$ as close to the photoelectric detectors in detectors 85, 86, and 286, respectively, as practical followed by digital signal processing as opposed to transmitting the signals $s_5$, $s_{5A}$, $S_6$, and $s_7$ as analog signals for subsequent analog signal processing and/or analog-to-digital conversion downstream. The compensation for a particular group delay can generally be introduced before or after, or in part before and in part after, the processing elements producing the particular group delay.

Electronic processor 109 additionally comprises processors 1094A to determine the phase shift $\phi_{5A}$ using time-based phase detection or the like by analog or digital signal processing, preferably by digital processing, reference signal 101 serving as the reference signal in phase sensitive detection. The phases $\phi_5$, $\Theta$, and $\Phi$ are transmitted to computer 110 as signal 105, in either digital or analog format, preferably in digital format.

The refractivity of the gas, $(n_5-1)$, can be calculated using the formula $$n_5 - 1 = \frac{\Gamma}{\chi L[1-(K/\chi)^2]}\{[\vartheta(K/\chi)-\Phi]-Q\}, \tag{55}$$

where L is the average of physical lengths $L_i$, $$\chi(l_5 k_5 + l_6 k_6)/2, \tag{56}$$

$$K(l_5 k_5 - l_6 k_6)/2, \tag{57}$$

$$\Gamma = \frac{n_5 - 1}{n_6 - n_5}, \tag{58}$$

and second order correction terms have been omitted. The second order correction terms are due to a first order change in the index of refraction in the measurement path i from the average of the index of refraction over the measurement paths i and to the difference of the physical length $L_i$ from L. The quantity $\Gamma$ is the reciprocal dispersive power of the gas that is substantially independent of environmental conditions and turbulence in the gas. The offset term Q is defined as $$Q = \zeta(K/\chi) - Z, \tag{59}$$

where $$\xi = \left(\frac{l_5}{p_1}\zeta_5 + \frac{l_6}{p_2}\frac{\zeta_6 + \zeta_7}{2}\right), \tag{60}$$

$$Z = \left(\frac{l_5}{p_1}\zeta_5 - \frac{l_2}{p_2}\frac{\zeta_6 + \zeta_7}{2}\right). \tag{61}$$

It is evident from the definition of K given by Eq. (57) that $(K/\chi)=0$ corresponds to the wavelengths $\lambda_5$ and $\lambda_6$ being strictly harmonically related according to the known ratio $l_5/l_6$. For an application where $|K/\chi|>0$ and the value of $(K/\chi)$ must be known to a certain precision in the use of Eqs. (55) and/or (62) to meet an end use requirement, $(K/\chi)$ is measured by wavelength monitor 550. For an application where the value of $\chi$ must be known to another certain precision in the use of Eqs.(55), (62), (67) and/or (15), $\chi$ is also measured by wavelength monitor 550. Measured values of $(K/\chi)$ and/or $\chi$ are transmitted as signal 550S to electronic processor 527 and to $\Gamma$ monitor 552 for use in determination of $\Gamma$, preferably in digital format.

The reciprocal dispersive power $\Gamma$ is measured and monitored by monitor 552. The preferred embodiment for $\Gamma$ monitor 552 is from the second group of $\Gamma$ monitor embodiments subsequently described herein. Measured values of $\Gamma$ are transmitted as signal 552S to electronic processor 527, preferably in digital format.

In addition, Eq. (55) is valid for the case where the combined paths for optical beams at one wavelength are substantially coextensive with the combined paths for optical beams at a second wavelength, a preferred configuration which also serves to illustrate in the simplest manner the function of the invention in the third embodiment with respect to reduction of Doppler shift effects in dispersion related signals. To those skilled in the art, the generalization to the case where combined paths for optical beams at one wavelength are not substantially coextensive with the combined paths for optical beams at a second wavelength is a straight forward procedure.

For those applications related to distance measuring interferometry, the heterodyne phase $\phi_5$ and phases $\Theta$ and $\Phi$ may be used to determine the distance L, independent of the effects of the refractive index of the gas in the measuring path of a distance measuring interferometer, using the formula $$L = \frac{1}{(\chi + K)}\left\{\frac{l_1}{p_1}(\varphi_1 - \zeta_1) - \frac{\Gamma}{[1-(K/\chi)]}[(K/\chi)\vartheta - \Phi - Q]\right\}. \tag{62}$$

The ratio of the wavelengths can be expressed in terms of $(K/\chi)$ from Eqs. (56) and (57) with the result $$\frac{\lambda_5}{\lambda_6} = \left(\frac{l_5}{l_6}\right)\left[\frac{1-(K/\chi)}{1+(K/\chi)}\right]. \tag{63}$$

When operating under the condition $$|K/\chi| \ll \frac{(n_6 - n_5)}{(n_6 + n_5)}, \tag{64}$$

the ratio of the phases $\Phi$ and $\Theta$ has the approximate value $$(\Phi/\vartheta) \cong -\frac{(n_6 - n_5)}{(n_6 + n_5)}. \tag{65}$$

Therefore, for the case of the third embodiment, when the ratio of the wavelengths $(\lambda_5/\lambda_6)$ is the same as the ratio value $l_5/l_6$ to a relative precision of an order of magnitude or more less than the dispersion of the refractive index of the gas, $(n_6-n_5)$, times the relative precision $\epsilon$ desired for the measurement of the change in the optical path length of the measurement leg due to the gas, expressed formally by the inequality $$\left|\frac{\lambda_5}{\lambda_6} - \frac{l_5}{l_6}\right| \ll \left(\frac{l_5}{l_6}\right)(n_5 - n_6)\varepsilon, \tag{66}$$

Eqs. (55) and (62) reduce to the more simple forms of $$n_5 - 1 = -\frac{\Gamma}{\chi L}(\Phi + Q), \tag{67}$$

$$L = \frac{1}{\chi}\left[\frac{l_5}{p_1}(\varphi_5 - \zeta_5) + \Gamma(\Phi + Q)\right], \tag{68}$$

respectively. It will also be obvious to someone skilled in the art to perform similar calculations for L with respect to $n_6$, $$(n_6-1)=(n_5-1)(1+1/\Gamma) \tag{69}$$

in place of or in addition to $n_5$.

In a next step, electronic processing means 109 transmits to the computer 110 $\phi_5$ and $\Phi$ as electronic signal 105 in either digital or analog format, preferably a digital format, for the computation of $(n_5-1)$ and/or L. The resolution of phase redundancy in $(1/l_5)\Phi$ is required in the computation of either $(n_5-1)$ or changes in L due to the gas using either Eqs. (67) or (68), respectively. In addition the resolution of the phase redundancy in $\phi_5$ is required in the computation of L using Eq. (62) or (68) if $\chi$ is variable in time.

The equivalent wavelength comprising $(1/l_5)\Phi$ is significantly larger than either of the wavelengths $\lambda_5$ and $\lambda_6$ and as a consequence, produces a significant simplification in a procedure implemented for resolution of phase redundancy in $(1/l_5)\Phi$. The equivalent wavelength $\lambda_{(1/l_5)\Phi}$ for $(1/l_5)\Phi$ is $$\lambda_{(1/l_5)\Phi} = \frac{\lambda_5}{(n_6 - n_5)} \tag{70}$$

For the example of $\lambda_5=0.633$ $\mu$m, $(n_5-1)\equiv 3\times 10^{-4}$, and $(n_6-n_5)\equiv 1\times 10^{-5}$, the equivalent wavelength given by Eq. (70) is $$\lambda_{(1/l_5)\Phi} \equiv 63 \text{ mm} \tag{71}$$

Any one of several procedures may be easily employed to resolve the phase redundancy in $(1/l_5)\Phi$, given the equivalent wavelength as expressed by Eq. (70). For those applications where changes in the measurement path can be measured interferometrically, a feature for example of an application based on a distance measuring interferometer employed for measuring changes in the measurement path, the movable mirror 92 of the external mirror system 90 can be scanned by translator 67 in a controlled manner over a given length and the concomitant change in $(1/l_5)\Phi$ recorded. From the recorded change in $(1/l_5)\Phi$ and the length scanned, as recorded by the change in $\phi_5$, the equivalent wavelength $\lambda_{(1/l_5)\Phi}$ can be calculated. With the computed value for the equivalent wavelength $\lambda_{(1/l_5)\Phi}$, the phase redundancy in $(1/l_5)\Phi$ can be easily resolved in view of the relatively large value for the equivalent wavelength $\lambda_{(1/l_5)\Phi}$.

For those applications where the determination of the refractivity and/or or the change in the optical path length due to the gas in a measurement leg is made and mirror 92 of the external mirror system does not have a scanning capability such as considered in the preceding paragraph, other procedures are available for the resolution of the phase redundancy of $(1/l_5)\Phi$. One procedure which may be employed to resolve the phase redundancy in $(1/l_5)\Phi$ is based on the use of a series of external mirror systems where the round-trip physical lengths L for the measurement legs of the external mirror systems form a geometric progression. The smallest or first round-trip physical length in the series will be approximately $\lambda_5/[4(n_6-n_5)]$ divided by the relative precision that the initial value of $(1/l_5)\Phi$ is known. The round-trip physical length of the second external mirror system 90 in the series will be approximately the round-trip physical length of the first external mirror system 90 divided by the relative precision that $\Phi$ is measured using the first external mirror system 90. This is a geometric progression procedure, the resulting round-trip physical lengths forming a geometric progression, which is continued until the round-trip physical length of the external mirror system 90 used to measure the refractivity or the change in optical path length due to the refractivity of the gas would be exceeded if the number of external mirror systems in series were incremented by one.

A third procedure is based upon the use of a source (not shown in FIGS. 1a–1e) of a series of known wavelengths and measuring $\Phi$ for these wavelengths. The number of known wavelengths required for the resolution of the phase redundancy is generally comprised of a small set because of the relatively large value for $\lambda_{(1/l_5)\Phi}$ as given by Eq. (70).

Another procedure to resolve the phase redundancy in $(1/l_5)\Phi$ would be to observe the changes in $(1/l_5)\Phi$ as the measuring path 98 is changed from gas to an evacuated state (the vacuum pump and requisite gas handling system are not shown in FIGS. 1a–1e) to resolve the phase redundancy in $(1/l_5)\Phi$. The problems normally encountered in measuring absolute values for refractivity and changes in the optical path length due to the refractivity of the gas based in part on changing the gas pressure from a non-zero value to a vacuum are not present in the first preferred embodiment because of the relative large equivalent wavelength of $(1/l_5)\Phi$.

The resolution of the phase redundancy in $\phi_5$ if required presents a problem similar to the one as subsequently described with respect to the required resolution of phase redundancy in $\Theta$ in the second and third embodiments and variants thereof of the present invention. As a consequence, the procedures described for the resolution of phase redundancy in $\Theta$ with respect to the second and third embodiments and variants thereof can be adapted for use in the resolution of the phase redundancy in $\phi_5$ if required.

The offset terms involving $\zeta_5$ or/and Q that are present in Eqs. (55), (62), (67), and (68) and defined in Eqs. (52) and (66), respectively, are terms that require some combination of determination and/or monitoring depending on whether $\chi$ is variable in time, whether the refractivity or/and the length L are to be determined, respectively, or whether changes in refractivity or/and the length L are to be determined, respectively. One procedure for the determination of $\zeta_5$ and Q is based on replacement of mirror 91 of the external mirror system 90 with a mirror R91 (not shown in FIGS. 1d and 1e) having a surface R93 corresponding to surface 93 of mirror 91 coated so as be a reflecting surface for both wavelengths $\lambda_5$ and $\lambda_6$ and measuring the resulting values of $\phi_5$ and $\Phi$. Let the resulting values of $\phi_5$ and $\Phi$ be $\phi_{5R}$ and $\Phi_R$, respectively. Quantities $\zeta_5$ and Q are related to $\phi_{5R}$ and $\Phi_R$, respectively, as evident from Eqs. (52) and (68) by the formulae $$\zeta_5 = \phi_{5R}, \tag{72}$$

$$Q = -\Phi_R. \tag{73}$$

The non-electronic contributions to $\zeta_5$ and Q should be substantially constant in time because of the significant level of compensation that takes place in the differential plane mirror interferometer 69, the differential plane mirror interferometer group 70, beam splitter 65, and external mirror system 90. The electronic contributions to $\zeta_5$ and Q may be monitored by purely electronic means (not shown).

It will be apparent to someone skilled in the art that as a consequence of the incorporation of beam splitter 65 in the first preferred embodiment, the measuring paths for beams at $\lambda_5$ and $\lambda_6$ are coextensive in external mirror system 90, so that the dispersion of the gas can serve as a proxy to high precision for the gas column density in the measuring path, whereas polarizing coating 73 of beam splitter 71 and quarter-wave retardation plate 77 need only meet performance specifications at $\lambda_5$ while polarizing coating 74 of beam splitter 72 and quarter-wave retardation plate 78 need only meet performance specifications at $\lambda_6$. This assignment of critical operations according to wavelength as disclosed in the first embodiment can be an important feature of the present invention when requiring use of three or more light beams with different wavelengths having coextensive measuring paths in the gas, particularly in high precision applications such as the case of micro-lithographic fabrication of integrated circuits. However, the assignment of operations according to wavelength need not be done as disclosed in the first preferred embodiment, e.g. the function of beam splitters 71 and 72 being achieved by a single beam splitter with an appropriately modified polarizing surface, without departing from the spirit or scope of the present invention.

FIG. 3b depicts in schematic form one embodiment of the differential plane mirror interferometer 69 shown in FIG. 1a. It operates in the following way: beam 9 is incident on beam splitter 55A, preferably a polarizing beam splitter, with a portion of beam 9 being transmitted as beam 13. A second portion of beam 9 reflected by beam splitter 55A is reflected by mirror 55B and then transmitted by half-wave phase retardation plate 79 as beam 113, the half-wave phase retardation plate 79 rotating the plane of polarization of the reflected portion of beam 9 by 90°. Beams 13 and 113 have the same polarizations but still have different frequencies. The function of beam splitter 55A and mirror 55B is to spatially separate the two frequency components of beam 9 using conventional polarization techniques.

Beams 13 and 113 enter polarizing beam splitter 71, which has a polarizing coating 73, and are transmitted as beams 15 and 115, respectively. Beams 15 and 115 pass through quarter-wave phase retardation plate 77 and are converted into circularly polarized beams 17 and 117, respectively. Beams 17 and 117 are transmitted by beam splitter 65 with dichroic coating 66, reflected back on themselves by mirrors within external mirror system 90 as illustrated in FIG. 1d, pass back through beam splitter 65, and subsequently pass back through quarter-wave retardation plate 77 and converted back into linearly polarized beams that are orthogonally polarized to the original incident beams 15 and 115. These beams are reflected by polarizing coating 73 to become beams 19 and 119, respectively. Beams 19 and 119 are reflected by retroreflector 75 to become beams 21 and 121, respectively. Beams 21 and 121 are reflected by polarizing coating 73 to become beams 23 and 123, respectively. Beams 23 and 123 pass through quarter-wave phase retardation plate 77 and are converted into circularly polarized beams 25 and 125, respectively. Beams 25 and 125 are transmitted by beam splitter 65, reflected back on themselves by mirrors within external mirror system 90 as illustrated in FIG. 3d, pass back through beam splitter 65, and subsequently pass back through quarter-wave retardation plate 77 and converted back into linearly polarized beams, the linear polarizations being the same as the linear polarizations of the original incident beams 15 and 115. These beams are transmitted by polarizing coating 73 to become beams 27 and 125, respectively. Beam 27 is reflected by mirrors 57A and 57B and beam 127 is reflected by mirrors 59C and 59D to become beams 29 and 129, respectively.

Beams 29 and 129 enter polarizing beam splitter 71 and are transmitted by polarizing beam splitter 71 with polarizing coating 73 as beams 31 and 131, respectively. Beams 31 and 131 pass through quarter-wave phase retardation plate 77 and are converted into circularly polarized beams 33 and 133, respectively. Beams 33 and 133 are transmitted by beam splitter 65, reflected back on themselves by mirrors within external mirror system 90 as illustrated in FIG. 1d, pass back through beam splitter 65, and subsequently pass back through quarter-wave retardation plate 77 and converted back into linearly polarized beams that are orthogonally polarized to the original incident beams 31 and 131. These beams are reflected by polarizing coating 73 to become beams 35 and 135, respectively. Beams 35 and 135 are reflected by retroreflector 75 to become beams 37 and 137, respectively. Beams 37 and 137 are reflected by polarizing coating 73 to become beams 39 and 139, respectively. Beams 39 and 139 pass through quarter-wave phase retardation plate 77 and are converted into circularly polarized beams 41 and 141, respectively. Beams 41 and 141 are transmitted by beam splitter 65, reflected back on themselves by mirrors within external mirror system 90 as illustrated in FIG. 1d, pass back through beam splitter 65, and subsequently pass back through quarter-wave retardation plate 77 and are converted back into linearly polarized beams, the linear polarizations being the same as the linear polarizations of the original incident beams 15 and 115. These beams are transmitted by polarizing coating 73 to become beams 43 and 143, respectively. Beams 43 and 143 contain information at wavelength $\lambda_5$ about the optical path lengths through the gas in the measurement path 98 wherein the effects of the refractivity of the gas is to be determined and about the optical path lengths through reference leg, respectively.

Beam 43 is reflected by mirror 63B, and then a portion reflected by beam splitter 63A, preferably a non-polarizing type, as a first component of beam 45. Beam 143 is incident on beam splitter 63A with a portion of beam 143 being transmitted as a second component of beam 45, the first and second components of beam 45 having the same linear polarizations but still having different frequencies.

FIG. 3c depicts in schematic form one embodiment of differential plane mirror interferometer group 70 shown in FIG. 3a. It operates in the following way: beam 12 is incident on beam splitter 56A, preferably a polarizing beam splitter, with a portion of beam 12 being transmitted as beam 14. A second portion of beam 12 reflected by beam splitter 56A is reflected by mirror 56B and then transmitted by half-wave phase retardation plate 80 as beam 114, the half-wave phase retardation plate 80 rotating the plane of polarization of the incident portion of beam 12 by 90°. Beams 14 and 114 have the same polarizations but different frequencies. The function, in part, of beam splitter 56A and mirror 56B is to spatially separate the two frequency components of beam 12 using conventional polarization techniques.

Beams 14 and 114 enter polarizing beam splitter 72, which has a polarizing coating 74, and are transmitted as beams 16 and 116, respectively. Beams 16 and 116 pass through quarter-wave phase retardation plate 78 and are converted into circularly polarized beams 18 and 118, respectively. Beams 18 and 118 are reflected by beam splitter 65 with dichroic coating 66, reflected back on themselves by mirrors within external mirror system 90 as illustrated in FIG. 1e, reflected by surface 66 of beam splitter 65 a second time, and subsequently pass back through quarter-wave retardation plate 78 and converted back into linearly polarized beams that are orthogonally polarized to the original incident beams 16 and 116. These beams are reflected by polarizing coating 74 to become beams 20 and 120, respectively. Beams 20 and 120 are reflected by retroreflector 76 to become beams 22 and 122, respectively.

Beams 22 and 122 are reflected by polarizing coating 74 to become beams 24 and 124, respectively. Beams 24 a d 124 pass through quarter-wave phase retardation plate 78 and are converted into circularly polarized beams 26 and 126, respectively. Beams 26 and 126 are reflected by surface 66 of beam splitter 65, reflected back on themselves by mirrors within external mirror system 90 as illustrated in FIG. 3e, reflected by surface 66 of beam splitter 65 a second time, and subsequently pass back through quarter-wave retardation plate 78 and converted back into linearly polarized beams, the same linear polarizations as the linear polarizations of the original incident beams 16 and 116. These beams are transmitted by polarizing coating 74 to become beams 28 and 128, respectively. Beams 28 and 128 contain information at wavelength $\lambda_6$ about the optical path lengths through the gas in measurement path 98 wherein the effects of the refractivity of the gas is to be determined and about the optical path lengths through the reference leg, respectively.

Beam 28 is reflected by mirror 58B, and then a portion reflected by beam splitter 58A, preferably a non-polarizing type, as a first component of beam 30. Beam 128 is incident on beam splitter 58A with a portion of beam 128 being transmitted as a second component of beam 30, the first and second components of beam 30 having the same linear polarizations but still having different frequencies.

Beam 212 is incident on beam splitter 56A with a portion of beam 212 being transmitted as beam 214. A second portion of beam 212 is reflected by beam splitter 56A, subsequently reflected by mirror 56B, and then transmitted by half-wave phase retardation plate 80 as beam 314, the half-wave phase retardation plate 80 rotating the plane of polarization of the incident portion of beam 212 by 90°. Beams 214 and 314 have the same polarizations but still have different frequencies. The function, in part, of beam splitter 56A and mirror 56B is to spatially separate the two frequency components of beam 212 using conventional polarization techniques.

Beams 214 and 314 enter polarizing beam splitter 72, which has a polarizing coating 74, and are transmitted as beams 216 and 316, respectively. Beams 216 and 316 pass through quarter-wave phase retardation plate 78 and are converted into circularly polarized beams 218 and 318, respectively. Beams 218 and 318 are reflected by surface 66 of beam splitter 65, reflected back on themselves by mirrors within external mirror system 90 as illustrated in FIG. 1e, reflected by surface 66 of beam splitter 65 a second time, and subsequently pass back through quarter-wave retardation plate 78 and converted back into linearly polarized beams that are orthogonally polarized to the original incident beams 216 and 316. These beams are reflected by polarizing coating 74 to become beams 220 and 320, respectively. Beams 220 and 320 are reflected by retroreflector 76 to become beams 222 and 322, respectively. Beams 222 and 322 are reflected by polarizing coating 74 to become beams 224 and 324, respectively. Beams 224 and 324 pass through quarter-wave phase retardation plate 78 and are converted into circularly polarized beams 226 and 326, respectively. Beams 226 and 326 are reflected by surface 66 of beam splitter 65, reflected back on themselves by mirrors within external mirror system 90 as illustrated in FIG. 3e, reflected by surface 66 of beam splitter 65 a second time, and subsequently pass back through quarter-wave retardation plate 78 and converted back into linearly polarized beams, the linear polarizations being the same as the linear polarizations of the original incident beams 216 and 316. These beams are transmitted by polarizing coating 74 to become beams 228 and 328, respectively. Beams 228 and 328 contain information at wavelength $\lambda_6$ about the optical path lengths through the gas in measurement path 98 wherein the effects of the refractivity of the gas is to be determined and about the optical path lengths through the reference leg, respectively.

Beam 228 is reflected by mirror 58D and then a portion reflected by beam splitter 58C, preferably a non-polarizing type, as a first component of beam 230. Beam 328 is incident on beam splitter 58C with a portion of beam 328 being transmitted as a second component of beam 230, the first and second components of beam 230 having the same linear polarizations but still having different frequencies.

A first variant of the third preferred embodiment is disclosed wherein the description of the apparatus of the first variant of the first embodiment is the same as that given for the apparatus of the third embodiment except with regard to the frequencies $f_5$ and $f_6$ of drivers 5 and 6, respectively, shown in FIG. 3a. In the first variant of the third embodiment, the frequencies of the two drivers 5 and 6 are the same, i.e. $f_5=f_6$. This feature of the first variant of the first embodiment eliminates the effects of differences in group delays in the first embodiment resulting from $f_5 \neq f_6$. The remaining description of the first variant of the first embodiment is the same as corresponding portions of the description given for the first embodiment.

Reference is now made to FIGS. 3a–3e and 3g which taken together depict in diagrammatic form a second variant of the third preferred embodiment of the present invention for measuring the relative physical path length of a measurement path and reference path. The second variant of the third embodiment corresponds to a special case of the third embodiment wherein the wavelengths $\lambda 5$ and $\lambda_6$ are approximately harmonically related and the ratio $(l_5/l_6)$ is expressible as the ratio of low order non-zero integers $(p_5/p_6)$, i.e.

$$l_5 = p_5, l_6 = p_6, \qquad (74)$$

$$\left(\frac{l_5}{l_6}\right) = \left(\frac{p_5}{p_6}\right), p_5, p_6 = 1, 2, \ldots, p_5 \neq p_6.$$

The description of the sources of light beams 9 and 10 and of light beams 9 and 10 for the second variant of the third embodiment is the same as that for description of the sources of light beams 9 and 10 and of light beams 9 and 10 given for the third embodiment with the additional requirement that the wavelengths be harmonically related to a relative precision sufficient to meet the required precision imposed on the output data by the final end use application. The description of the apparatus for the second variant of the third embodiment depicted in FIGS. 3a–3e is the same as corresponding portions of the description given for the third embodiment for the case where $p_1=4$ and $p_2=2$.

Figure 3G:
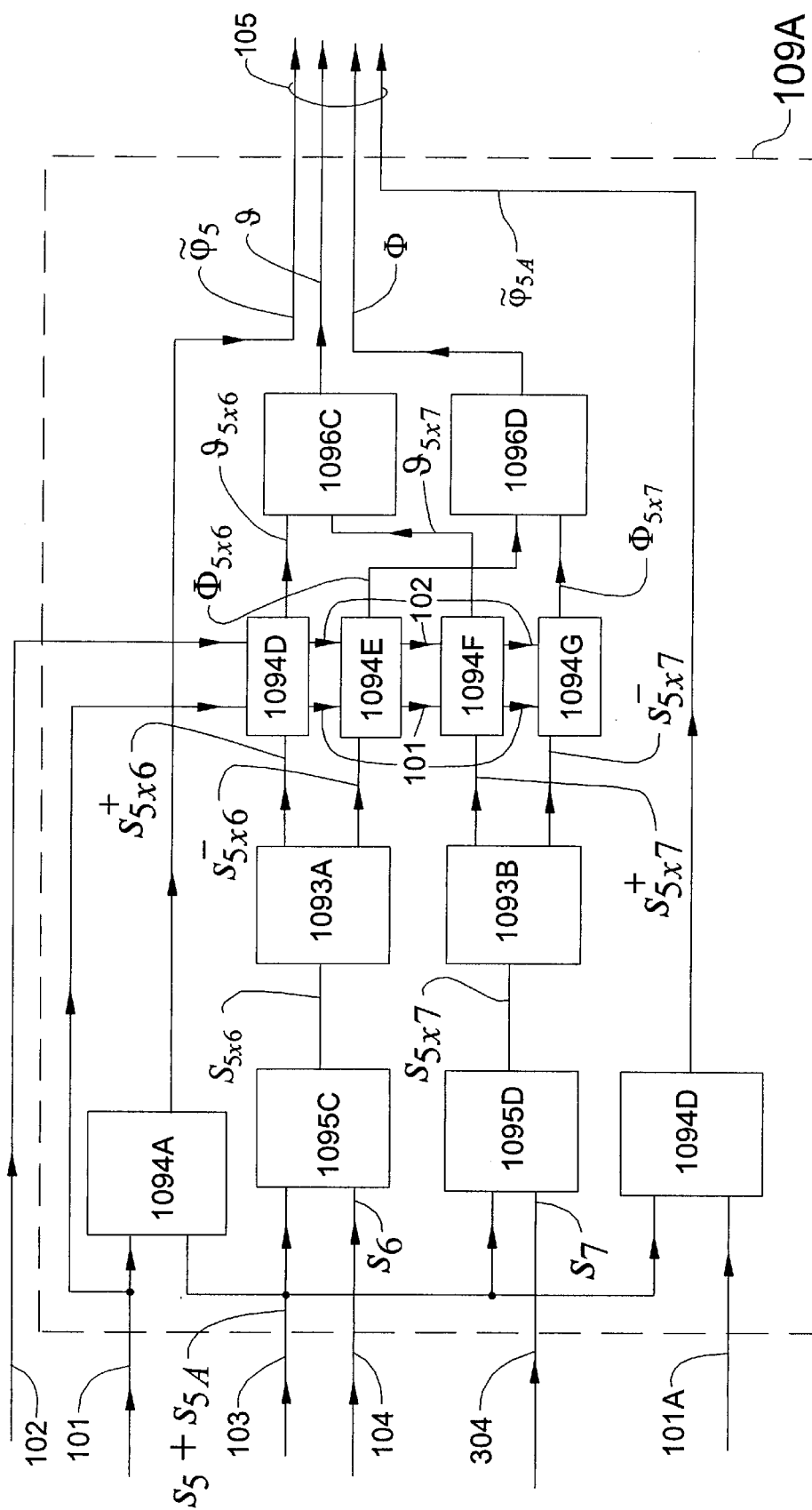
FIG. 3g depicts in diagrammatic form details of a variant of a portion of the embodiments shown in FIGS. 3a–3e.

Referring now to FIG. 3g, electronic processor 109A preferably comprises electronic processor 1095C for electronically multiplying together, either as an analog or digital process, preferably a digital process, heterodyne signals $s_5$ and $s_6$ to create a superheterodyne signal $S_{5 \times 6}$ having the mathematical form $$S_{5 \times 6} = s_5 s_6. \qquad (75)$$

Superheterodyne signal $S_{5 \times 6}$ is comprised of two sidebands with a suppressed carrier and may be rewritten as $$S_{5\times6} = S_{5\times6}^+ + S_{5\times6}^- \tag{76}$$

where $$S_{5\times6}^+ = \tfrac{1}{2}A_5A_6\cos(2\pi vt + \Theta_{5\times6}), \tag{77}$$

$$S_{5\times6}^- = \tfrac{1}{2}A_5A_6\cos(2\pi Ft + \Phi_{5\times6}), \tag{78}$$

$$v = (f_5 + f_6), \tag{79}$$

$$\Theta_{5\times6} = (\phi_5 + \phi_6), \tag{80}$$

$$F = (f_5 - f_6), \tag{81}$$

$$\Phi_{5\times6} = (\phi_5 - \phi_6). \tag{82}$$

Superheterodyne signal $S_{5\times6}$ is therefore comprised of two sidebands, $S_{5\times6}^+$ and $S_{5\times6}^-$, of equal amplitude, one sideband with frequency v and phase $\Theta_{5\times6}$ and a second sideband with frequency F and phase $\Phi_{5\times6}$.

In a next step, sidebands $S_{5\times6}^+$ and $S_{5\times6}^-$, are separated by electronic processor 1093A through high pass and low pass filtering or any of the like techniques for separating two signals that are separated in frequency. The frequency F of the lower frequency sideband of the superheterodyne signal is chosen to be very much smaller than the frequency v of the higher frequency sideband of the superheterodyne signal, so as to make it easier to calculate the phase $\phi_{5\times6}$ with high resolution, considerably simplifying the separating task of processor 1093A. Electronic processor 109A further comprises electronic processor 1094D and 1094E to determine the phases $\Theta_{5\times6}$ and $\Phi_{5\times6}$, respectively, using time-based phase detection such as a digital Hilbert transform phase detector (see R. E. Best, ibid.) or the like and the phases of the drivers 5 and 6.

Electronic processor 109A further comprises electronic processor 1095D which electronically multiplies together, either as an analog or digital process, preferably a digital process, heterodyne signals $s_5$ and $s_7$ to create a superheterodyne signal $S_{5\times7}$ having the mathematical form $$S_{5\times7} = s_5 s_7. \tag{83}$$

Superheterodyne signal $S_{5\times7}$ also comprised of two sidebands with a suppressed carrier and may be rewritten as $$S_{5\times7} = S_{5\times7}^+ + S_{5\times7}^- \tag{84}$$

where $$S_{5\times7}^+ = \tfrac{1}{2}A_5A_7\cos(2\pi vt + \Theta_{5\times7}), \tag{85}$$

$$S_{5\times7}^- = \tfrac{1}{2}A_5A_7\cos(2\pi Ft + \Phi_{5\times7}), \tag{86}$$

$$\Theta_{5\times7} = (\phi_5 + \phi_7), \tag{87}$$

$$\Phi_{5\times7} = (\phi_5 - \phi_7). \tag{88}$$

Superheterodyne signal $S_{5\times7}$ therefore comprises two sidebands, $S_{5\times7}^+$ and $S_{5\times7}^-$, of equal amplitude, one sideband with frequency v and phase $\Theta_{5\times7}$ and a second sideband with frequency F and phase $\Phi_{5\times7}$.

In a next step, the sidebands $S_{5\times7}^+$ and $S_{5\times7}^-$, are separated by electronic processor 1093B through high pass and low pass filtering or any of the like techniques for separating two signals that are separated in frequency. As noted in the discussion of electronic processor 1093A, the frequency F of the lower frequency sideband of superheterodyne signal $S_{5\times7}$ is chosen to be very much smaller than the frequency v of the higher frequency sideband of superheterodyne signal $S_{5\times7}$, considerably simplifying the separating task of processor 1093B. Electronic processor 109A further comprises processor 1094F and 1094G, respectively, to determine the phases $\Theta_{5\times7}$ and $\Phi_{5\times7}$ using time-based phase detection such as a digital Hilbert transform phase detector (see Best ibid.) or the like and the phases of the drivers 5 and 6.

Subsequently, the phases $\Theta_{5\times6}$ and $\Theta_{5\times7}$ are added together and divided by 2 in electronic processor 1096C, by an analog or digital process, preferably a digital process, and phases $\phi_{5\times6}$ and $\phi_{5\times7}$ are added together and divided by 2 in electronic processor 1096D, by an analog or digital process, preferably a digital process, to create the phases $\Theta$ and $\Phi$, respectively. Formally, $$\vartheta = \frac{(\vartheta_{5\times6} + \vartheta_{5\times7})}{2} = \left[\tilde{\varphi}_5 + \frac{(\tilde{\varphi}_6 + \tilde{\varphi}_7)}{2}\right], \tag{89}$$

$$\Phi = \frac{(\Phi_{5\times6} + \Phi_{5\times7})}{2} = \left[\tilde{\varphi}_5 - \frac{(\tilde{\varphi}_6 + \tilde{\varphi}_7)}{2}\right]. \tag{90}$$

Note from Eqs. (89) and (90) that $\Theta$ and $\Phi$ are not sensitive to tilt and/or yaw of mirrors 91 and 92 of external mirror system 90, except for instantaneous changing of tilt and/or yaw of mirrors 91 and 92 through higher order effects of the differences in the average time delay for light beams of differing wavelengths [see Eq. (74)], and insensitive to thermal and mechanical disturbances that may occur in the interferometer beam splitting cubes and associated optical components as a consequence of the use of differential plane mirror interferometers.

Electronic processor 109A, and shown in FIG. 3g, comprises electronic processor 1094A to determine phase $\phi_5$ from heterodyne signal $s_5$ using time-based phase sensitive detection with reference signal 101 or the like, preferably a digital process. Phases $\phi_5$, $\Theta$, and $\Phi$ are transmitted, in digital or analog format, preferably a digital format, to computer 110 as signal 105 for the computation of $(n_5-1)$ and/or L.

The refractivity $(n_5-1)$ of the gas or changes in L due to the gas in the measuring path can be expressed in terms of other quantities obtained in the second variant of the third embodiment by Eqs. (54), (56), (58), (59), (67), and (68) with $$l_5 = p_5,\ l_6 = p_6. \tag{91}$$

The remaining discussion of the second variant of the third embodiment is the same as corresponding portions of the descriptions given for the third embodiment.

The principal advantage of the second variant of the third embodiment is an option for the execution of critical electronic processing steps, such as the determination of phases $\phi_{5\times6}$ and $\phi_{5\times7}$ at substantially identical frequencies, the frequencies of heterodyne signals $s_5$, $s_6$, and $s_7$ being substantially identical in regard to $f_5$ being close to $f_6$ and to the Doppler shifts produced by the translation of mirror 92 of external mirror system 90 being substantially the same in $s_5$, $s_6$, and $s_7$ so as to substantially reduce the potential for generating differences in group delays experienced by heterodyne signals having significantly different frequencies. The discussion of the effects of group delay for the second variant of the third embodiment is the same as corresponding portions of the description given for the third embodiment.

A preferred second variant of the third embodiment of the invention having been disclosed in the previous paragraphs, the underlying advantages of the invention will be made more clear by the following discussion. It is evident from the calculation of the refractivity by Eq. (55) or the calculation of the effect of the refractivity of the gas in the optical path by Eq. (62), that the required accuracies to which the phases Θ and Φ must be determined are related to the values of the wavenumbers K and χ. In that frequency F can be very much smaller than the frequency ν, and since it is generally easier to calculate the phase with high resolution of an electronic signal of lower frequency, it is generally most advantageous to rely on a high-accuracy measurement of the superheterodyne derived sideband phase Φ. This is readily achieved in the inventive apparatus when the wavenumbers K and χ are related according to Eq. (64) whereupon the calculation of the refractivity by Eq. (55) or the calculation of the effect of the refractivity of the gas on the optical path by Eq. (62) substantially does not involve superheterodyne derived sideband phase Θ at all. Further, the magnitude of superheterodyne derived sideband phase Φ is less than the magnitude of the superheterodyne derived sideband phase Θ, less dependent by a factor of approximately $(n_6-n_5)/(n_6+n_5)$ as expressed by Eq. (65). This greatly improves the potential phase detection accuracy for moving objects, such as are commonly encountered in micro-lithography equipment. A corresponding analysis and summary also applies to the third embodiment and to the first variant of the third embodiment wherein there is an improvement in the phase detection accuracy for moving objects substantially proportional to the relative precision that the approximate ratio value $l_5/l_6$ can be expressed as the ratio of low order non-zero integers, all other factors being the same.

Eq. (66) also forms the basis for a conclusion that sources 1 and 2 need not be phase locked for the first variant of the first preferred embodiment. Eq. (66) is actually a weak condition when viewed in terms of a phase-locked requirement for sources 1 and 2. Consider for an example a desired precision of $\epsilon \equiv 3 \times 10^{-6}$ for measuring the refractivity $(n_5-1)$ of the gas or for the change in the optical path length of the measurement leg due to the gas, corresponding to a relative distance measuring precision of approximately $1 \times 10^{-9}$ in a distance measuring interferometer, $(n_5-1) \equiv 3 \times 10^{-4}$, and $(n_6-n_5) \equiv 1 \times 10^{-5}$. For the example, the condition expressed by Eq. (66) written in terms of source frequencies $v_5$ and $v_6$ instead of wavelengths $\lambda_5$ and $\lambda_6$, respectively, is $$\left| v_6 - \frac{p_5}{p_6} v_5 \right| \ll 3 \times 10^{-11} v_6. \quad (92)$$

For source wavelengths in the visible part of the spectrum and for low order integers for $p_5$ and $p_6$, Eq. (92) translates into a condition $$\left| v_6 - \frac{p_5}{p_6} v_5 \right| \ll 30 \text{ kHz}. \quad (93)$$

The result expressed in Eq. (93) is clearly a significantly less restrictive condition on the frequencies of sources 1 and 2 than a phase-locked condition.

The third embodiment and first and second variants thereof are each configured with differential plane mirror interferometers using an even number of passes of a beam through measurement path 98 of external mirror system 90. With an even number of passes by a beam in a differential plane mirror interferometer, the direction of propagation of an exit beam from the measurement leg and the direction of propagation of the corresponding exit beam from the reference leg are independent of tilt or yaw of either mirror in the external mirror system 90, in particular mirror 92, although there will be certain lateral shear of one of the exit beams relative to the other of the exit beams. For a distance measuring interferometer wherein the element or elements serving the function of mirror 92 generates the equivalent of translations but does not produce the equivalent of tilts or yaws, the differential plane mirror interferometers of the first embodiment and variants thereof can be configured with $p_6$ either an even or odd integer, generally reducing the number of required passes by two, while retaining the features of the first embodiment and variants thereof. This reduction by a factor of two in the required number of passes can lead to a significant simplification of the optical system. For example, the differential plane mirror interferometers illustrated in FIGS. 3a–3e can be replaced with differential plane mirror interferometers having $p_5=2$ and $p_6=1$, otherwise retaining the features of the third embodiment and variants thereof, similar to the differential plane mirror interferometers and accompanying signal processing more fully illustrated and described with respect to the second embodiment and variants thereof in commonly owned copending U.S. patent application Ser. No. 09/232,515 entitled "APPARATUS AND METHODS FOR MEASURING INTRINSIC OPTICAL PROPERTIES OF A GAS". As mentioned earlier, the contents of the foregoing application are incorporated herein by reference.

Figure 4:
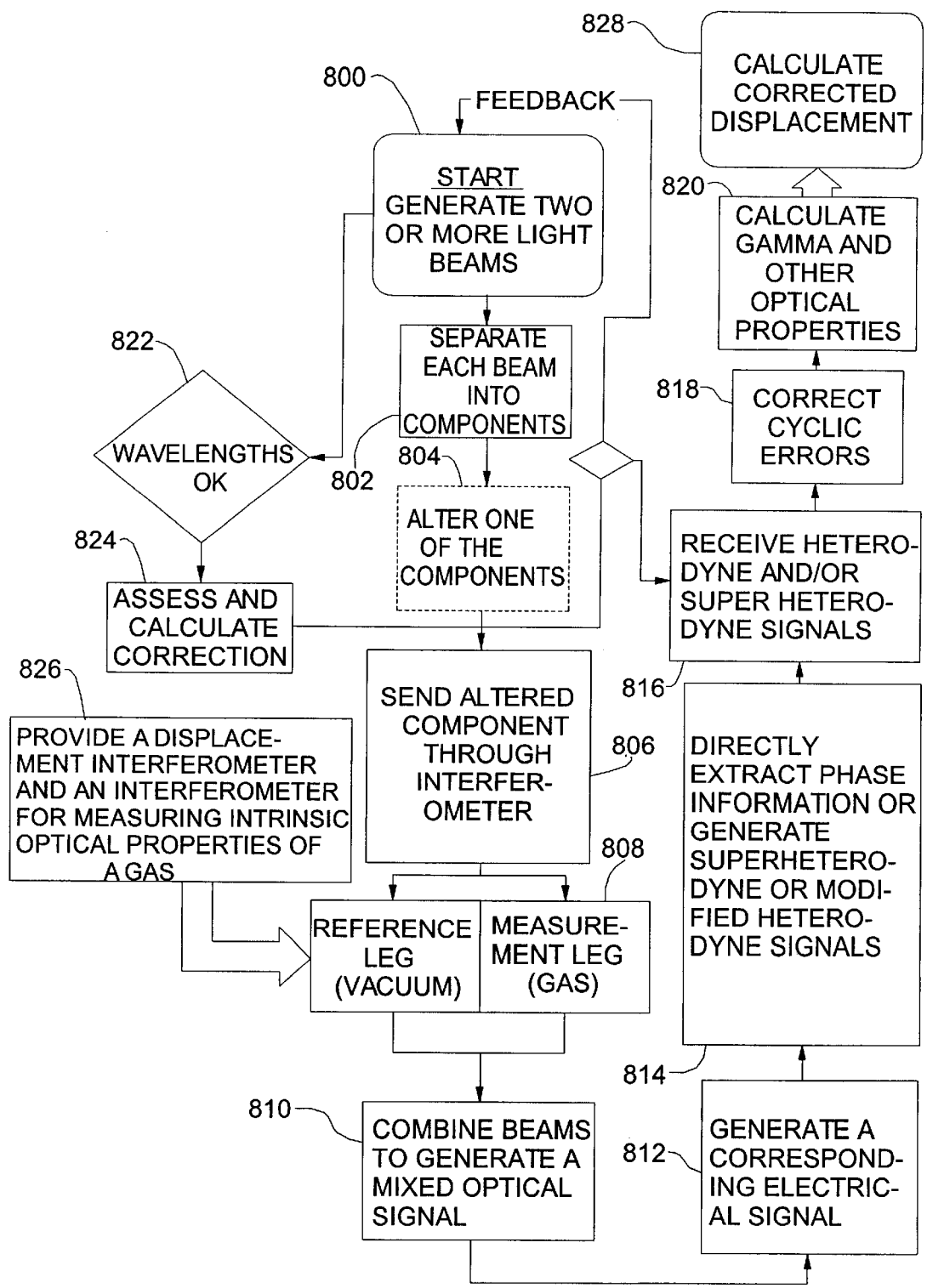
FIG. 4 is a high level flowchart showing various steps that are carried out in practicing the method of the invention.

Reference is now made to FIG. 4 which is a generalized flowchart depicting via blocks 800–828 various steps for practicing an inventive method for measuring and monitoring the refractivity of a gas in a measurement path and/or the change in the optical path length of the measurement path due to the gas wherein the refractivity of the gas may be changing and/or the physical length of the measurement path may be changing. While it will be evident that the inventive method depicted in FIG. 4 may be carried out using the inventive apparatus disclosed hereinabove, it will also be apparent to those skilled in the art that it may also be implemented with apparatus other than that disclosed. For example, it will be apparent that one need not use the interferometers such as those used in the preferred embodiments, but rather may use other conventional interferometric arrangements so long as the required reference and measurement legs are present. In addition, it will be evident that one may use either a homodyne approach or one in which heterodyning techniques are advantageously employed. As will be further appreciated, many of the steps in FIG. 4 may be carried out via appropriate software run on a general purpose computer or a suitably programmed microprocessor either of which may be used to control other elements of the system as needed.

As seen in FIG. 4, one starts in block 800 by providing two or more light beams having different wavelengths which preferably have an approximate harmonic relationship as previously described. In block 802, the light beams are separated into components which in block 804 are preferably altered by either polarization or spatial encoding, or frequency shifting or both. Otherwise, the light beams may simply be left unaltered and passed through to block 806.

As shown in blocks 822 and 824, the relationship of the wavelengths of the light beams and/or the wavelengths may be monitored and if their wavelengths are not within the limits previously discussed, one can adopt corrective measures to compensate from departures of the relationship of the wavelengths from the desired relationship of the wavelengths or of the wavelengths themselves. Either the departures can be used to provide feedback to control the wavelengths of the light beam sources or corrections can be established and used in subsequent calculations which are influenced by departures or some combination of both approaches can be implemented.

In parallel or contemporaneously with generating the light beams in block 800, one also provides as indicated in block 826 a displacement measuring interferometer having two legs, a reference leg and the other a measurement leg wherein a portion of the measurement path is in a gas whose refractivity and/or effect on the optical path length of the measurement path are to be measured along with an interferometer for use in measuring and monitoring select intrinsic optical properties of the gas.

As shown by blocks 806 and 808, the previously generated light beam components are introduced into the respective interferometer legs so that each component has its phase shifted based on the optical path length it experiences in traveling through the physical length of its assigned leg.

After the beams emerge from block 808, they are combined in block 810 to generate a mixed optical signal. These mixed optical signals are then sent to block 812 where by means of photodetection corresponding electrical signals, preferably heterodyne, are generated, and these electrical signals contain information about the relative phases between the light beam components. Preferably the electrical signals are heterodyne signals brought about by previously frequency shifting treatment.

In block 814, the electrical signals may be directly analyzed to extract relative phase information which can then be passed on to blocks 816–820 or, superheterodyne signals are generated and subsequently analyzed for the relative phase information.

In block 816, any phase ambiguities in homodyne, heterodyne, and/or superheterodyne signals are resolved, preferably by means and calculations previously elaborated in connection with describing the preferred embodiments.

In block 818 cylic errors are compensated along with wavelength corrections as previously determined.

In block 820, the refractivity of the gas and/or the effect of the refractivity of the gas on the optical path length of the measurement path are calculated, corrections are applied as previously decided, and output signals are generated for subsequent downstream applications or data format requirements. Here, changes or rates in chanage in intrinsic optical properties may be changed if they exceed predefined limits. Finally, in block 828, the corrected displacement is calculated.

Those skilled in the art may make other changes to the inventive apparatus and methods without departing from the scope of the inventive teachings. Therefore, it is intended that the embodiments shown and described be considered as illustrative and not in a limiting sense.

The interferometry systems described above can be especially useful in lithography applications (as diagrammatically indicated at 67) used for fabricating large scale integrated circuits such as computer chips and the like. Lithography is the key technology driver for the semiconductor manufacturing industry. Overlay improvement is one of the five most difficult challenges down to and below 100 nm line widths (design rules), see for example the *Semiconductor Industry Roadmap*, p82 (1997). Overlay depends directly on the performance, i.e. accuracy and precision, of the distance measuring interferometers used to position the wafer and reticle (or mask) stages. Since a lithography tool may produce $50–100M/year of product, the economic value from improved performance distance measuring interferometers is substantial. Each 1% increase in yield of the lithography tool results in approximately $1M/year economic benefit to the integrated circuit manufacturer and substantial competitive advantage to the lithography tool vendor.

The function of a lithography tool is to direct spatially patterned radiation onto a photoresist-coated wafer. The process involves determining which location of the wafer is to receive the radiation (alignment) and applying the radiation to the photoresist at that location (exposure).

To properly position the wafer, the wafer includes alignment marks on the wafer that can be measured by dedicated sensors. The measured positions of the alignment marks define the location of the wafer within the tool. This information, along with a specification of the desired patterning of the wafer surface, guides the alignment of the wafer relative to the spatially patterned radiation. Based on such information, a translatable stage supporting the photoresist-coated wafer moves the wafer such that the radiation will expose the correct location of the wafer.

During exposure, a radiation source illuminates a patterned reticle, which scatters the radiation to produce the spatially patterned radiation. The reticle is also referred to as a mask, and these terms are used interchangeably below. In the case of reduction lithography, a reduction lens collects the scattered radiation and forms a reduced image of the reticle pattern. Alternatively, in the case of proximity printing, the scattered radiation propagates a small distance (typically on the order of microns) before contacting the wafer to produce a 1:1 image of the reticle pattern. The radiation initiates photo-chemical processes in the photoresist that convert the radiation pattern into a latent image within the photoresist.

The interferometry systems described above are important components of the positioning mechanisms that control the position of the wafer and reticle, and register the reticle image on the wafer.

In general, the lithography system, also referred to as an exposure system, typically includes an illumination system and a wafer positioning system. The illumination system includes a radiation source for providing radiation such as ultraviolet, visible, x-ray, electron, or ion radiation, and a reticle or mask for imparting the pattern to the radiation, thereby generating the spatially patterned radiation. In addition, for the case of reduction lithography, the illumination system can include a lens assembly for imaging the spatially patterned radiation onto the wafer. The imaged radiation exposes photoresist coated onto the wafer. The illumination system also includes a mask stage for supporting the mask and a positioning system for adjusting the position of the mask stage relative to the radiation directed through the mask. The wafer positioning system includes a wafer stage for supporting the wafer and a positioning system for adjusting the position of the wafer stage relative to the imaged radiation. Fabrication of integrated circuits can include multiple exposing steps. For a general reference on lithography, see, for example, J. R. Sheats and B. W. Smith, in *Microlithography: Science and Technology* (Marcel Dekker, Inc., New York, 1998), the contents of which are incorporated herein by reference.

The interferometry systems described above can be used to precisely measure the positions of each of the wafer stage and mask stage relative to other components of the exposure system, such as the lens assembly, radiation source, or support structure. In such cases, the interferometry system can be attached to a stationary structure and the measurement object attached to a movable element such as one of the mask and wafer stages. Alternatively, the situation can be reversed, with the interferometry system attached to a movable object and the measurement object attached to a stationary object.

More generally, the interferometry systems can be used to measure the position of any one component of the exposure system relative to any other component of the exposure system in which the interferometry system is attached, or supported by one of the components and the measurement object is attached, or is supported by the other of the components.

Figure 5A:
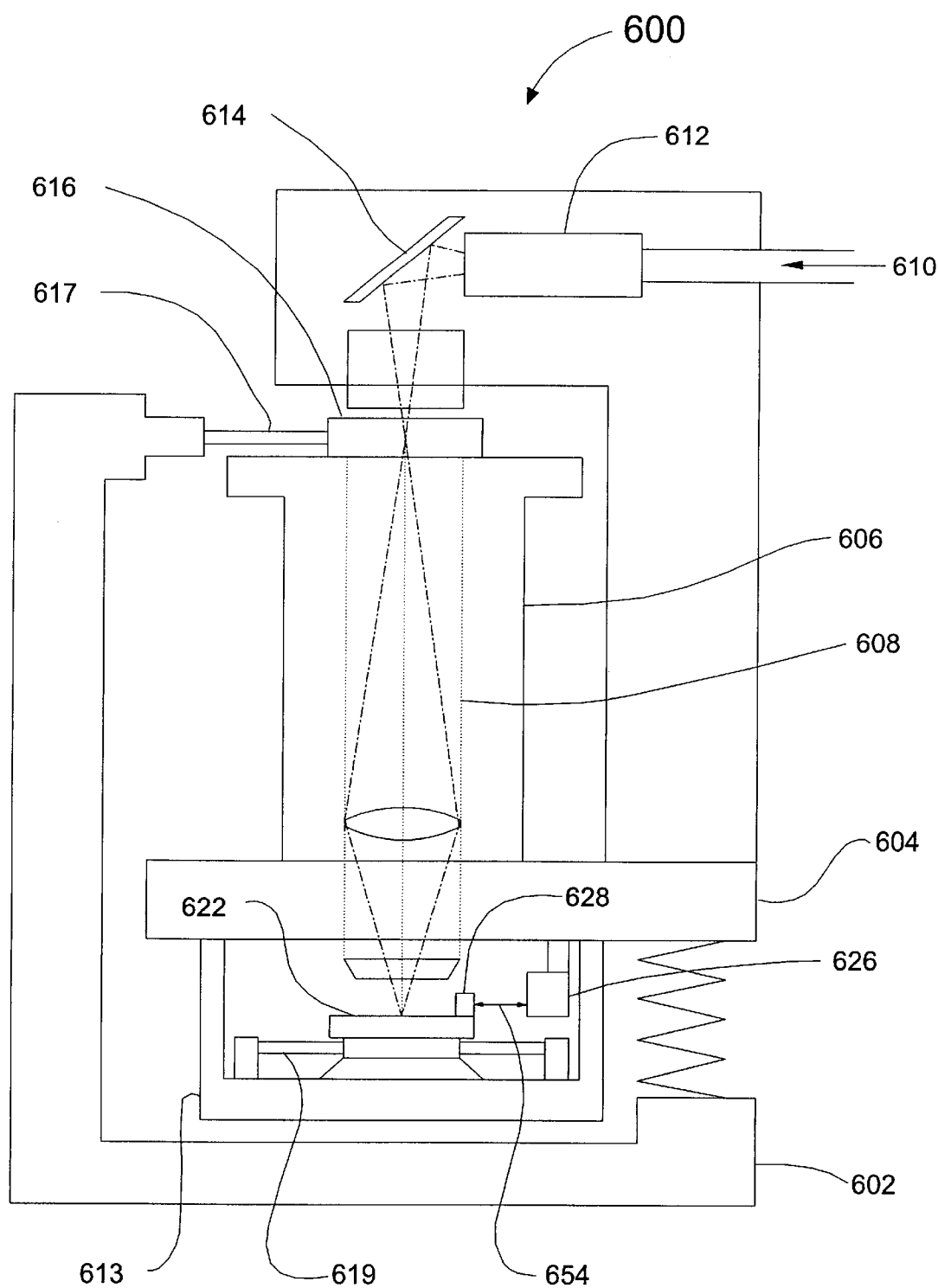

An example of a lithography scanner 600 using an interferometry system 626 is shown in FIG. 5a. The interferometry system is used to precisely measure the position of a wafer within an exposure system. Here, stage 622 is used to position the wafer relative to an exposure station. Scanner 600 comprises a frame 602, which carries other support structures and various components carried on those structures. An exposure base 604 has mounted on top of it a lens housing 606 atop of which is mounted a reticle or mask stage 616 used to support a reticle or mask. A positioning system for positioning the mask relative to the exposure station is indicated schematically by element 617. Positioning system 617 can include, e.g., piezoelectric transducer elements and corresponding control electronics. Although, it is not included in this described embodiment, one or more of the interferometry systems described above can also be used to precisely measure the position of the mask stage as well as other moveable elements whose position must be accurately monitored in processes for fabricating lithographic structures (see supra Sheats and Smith *Microlithography: Science and Technology*).

Suspended below exposure base 604 is a support base 613 that carries wafer stage 622. Stage 622 includes a plane mirror for reflecting a measurement beam 654 directed to the stage by interferometry system 626. A positioning system for positioning stage 622 relative to interferometry system 626 is indicated schematically by element 619. Positioning system 619 can include, e.g., piezoelectric transducer elements and corresponding control electronics. The measurement beam reflects back to the interferometry system, which is mounted on exposure base 604. The interferometry system can be any of the embodiments described previously.

During operation, a radiation beam 610, e.g., an ultraviolet (UV) beam from a UV laser (not shown), passes through a beam shaping optics assembly 612 and travels downward after reflecting from mirror 614. Thereafter, the radiation beam passes through a mask (not shown) carried by mask stage 616. The mask (not shown) is imaged onto a wafer (not shown) on wafer stage 622 via a lens assembly 608 carried in a lens housing 606. Base 604 and the various components supported by it are isolated from environmental vibrations by a damping system depicted by spring 620.

In other embodiments of the lithographic scanner, one or more of the interferometry systems described previously can be used to measure distance along multiple axes and angles associated for example with, but not limited to, the wafer and reticle (or mask) stages. Also, rather than a UV laser beam, other beams can be used to expose the wafer including, e.g., x-ray beams, electron beams, ion beams, and visible optical beams.

In addition, the lithographic scanner can include a column reference in which interferometry system 626 directs the reference beam to lens housing 606 or some other structure that directs the radiation beam rather than a reference path internal to the interferometry system. The interference signal produced by interferometry system 626 when combining measurement beam 654 reflected from stage 622 and the reference beam reflected from lens housing 606 indicates changes in the position of the stage relative to the radiation beam. Furthermore, in other embodiments the interferometry system 626 can be positioned to measure changes in the position of reticle (or mask) stage 616 or other movable components of the scanner system. Finally, the interferometry systems can be used in a similar fashion with lithography systems involving steppers, in addition to, or rather than, scanners.

Figure 5B:
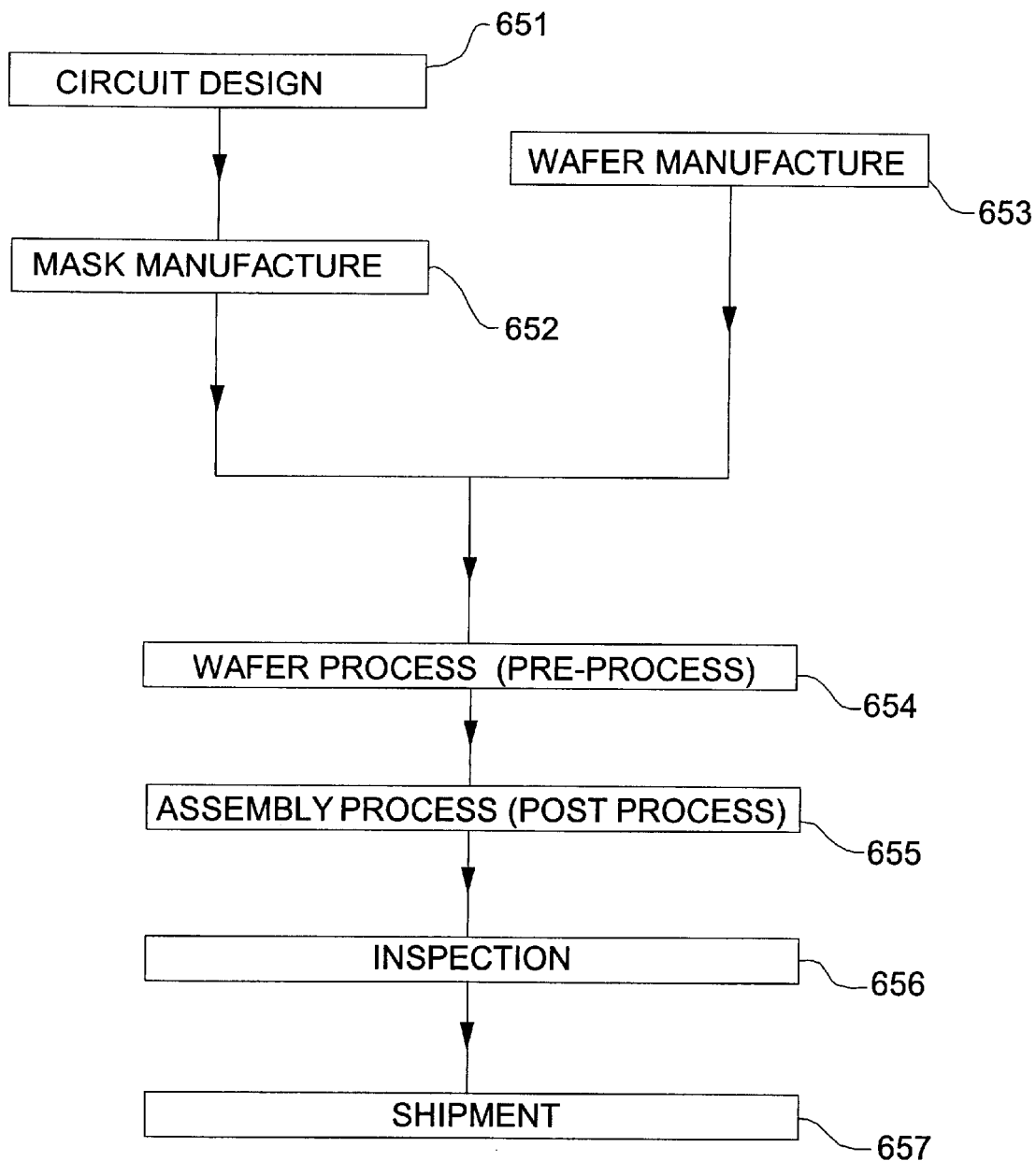

As is well known in the art, lithography is a critical part of manufacturing methods for making semiconducting devices. For example, U.S. Pat. No. 5,483,343 outlines steps for such manufacturing methods. These steps are described below with reference to FIGS. 5b and 5c. FIG. 5b is a flow chart of the sequence of manufacturing a semiconductor device such as a semiconductor chip (e.g. IC or LSI), a liquid crystal panel or a CCD. Step 651 is a design process for designing the circuit of a semiconductor device. Step 652 is a process for manufacturing a mask on the basis of the circuit pattern design. Step 653 is a process for manufacturing a wafer by using a material such as silicon.

Step 654 is a wafer process which is called a pre-process wherein, by using the so prepared mask and wafer, circuits are formed on the wafer through lithography. Step 655 is an assembling step, which is called a post-process wherein the wafer processed by step 654 is formed into semiconductor chips. This step includes assembling (dicing and bonding) and packaging (chip sealing). Step 656 is an inspection step wherein operability check, durability check, and so on of the semiconductor devices produced by step 655 are carried out. With these processes, semiconductor devices are finished and they are shipped (step 657).

Figure 5C:
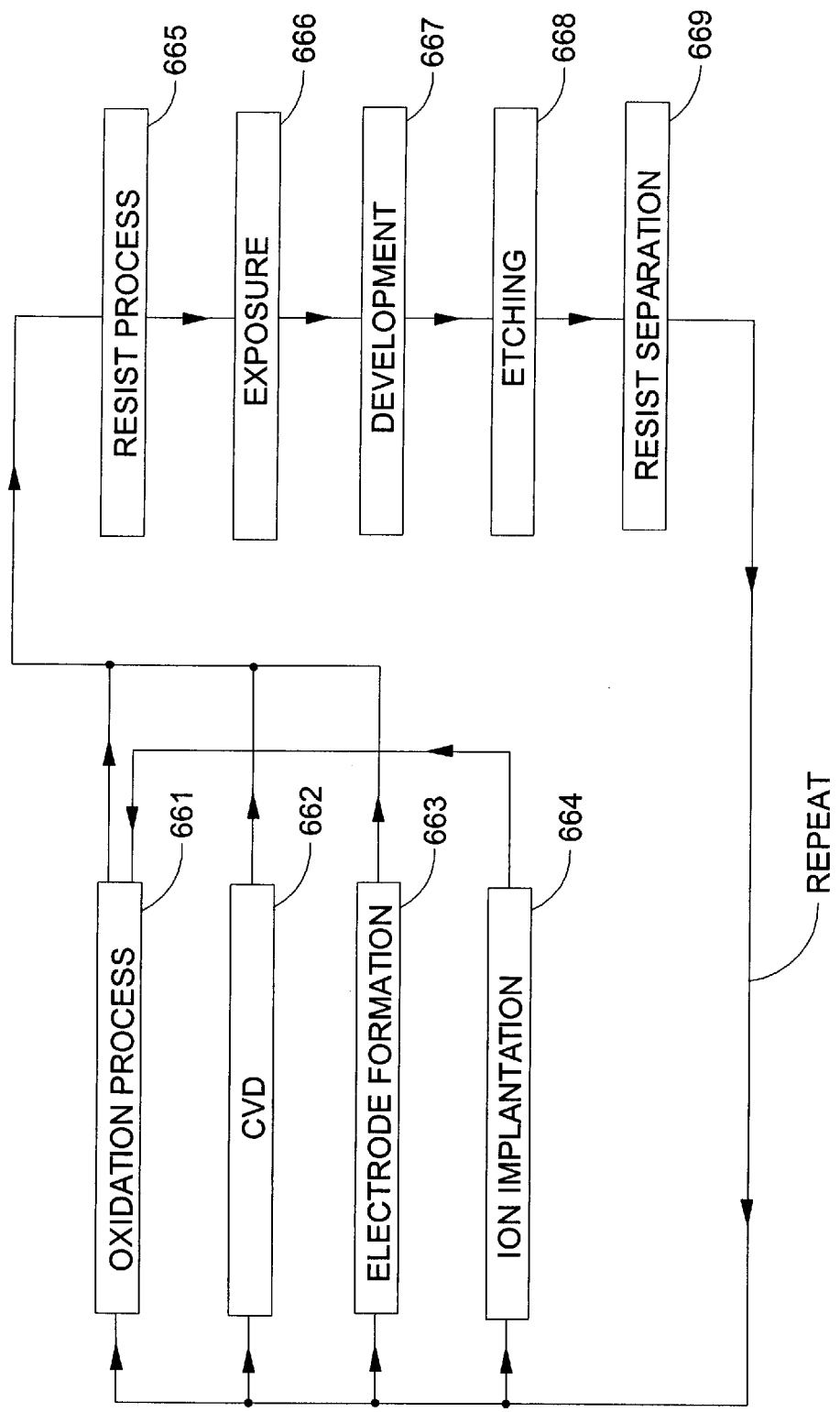

FIG. 5c is a flow chart showing details of the wafer process. Step 661 is an oxidation process for oxidizing the surface of a wafer. Step 662 is a CVD process for forming an insulating film on the wafer surface. Step 663 is an electrode forming process for forming electrodes on the wafer by vapor deposition. Step 664 is an ion implanting process for implanting ions to the wafer. Step 665 is a photoresist process for applying a photoresist (photosensitive material) to the wafer. Step 666 is an exposure process for printing, by exposure, the circuit pattern of the mask on the wafer through the exposure apparatus described above. Step 667 is a developing process for developing the exposed wafer. Step 668 is an etching process for removing portions other than the developed photoresist image. Step 669 is a photoresist separation process for separating the photoresist material remaining on the wafer after being subjected to the etching process. By repeating these processes, circuit patterns are formed and superimposed on the wafer.

The interferometry systems described above can also be used in other applications in which the relative position of an object needs to be measured precisely. For example, in applications in which a write beam such as a laser, x-ray, ion, or electron beam, marks a pattern onto a substrate as either the substrate or beam moves, the interferometry systems can be used to measure the relative movement between the substrate and write beam.

Figure 6:
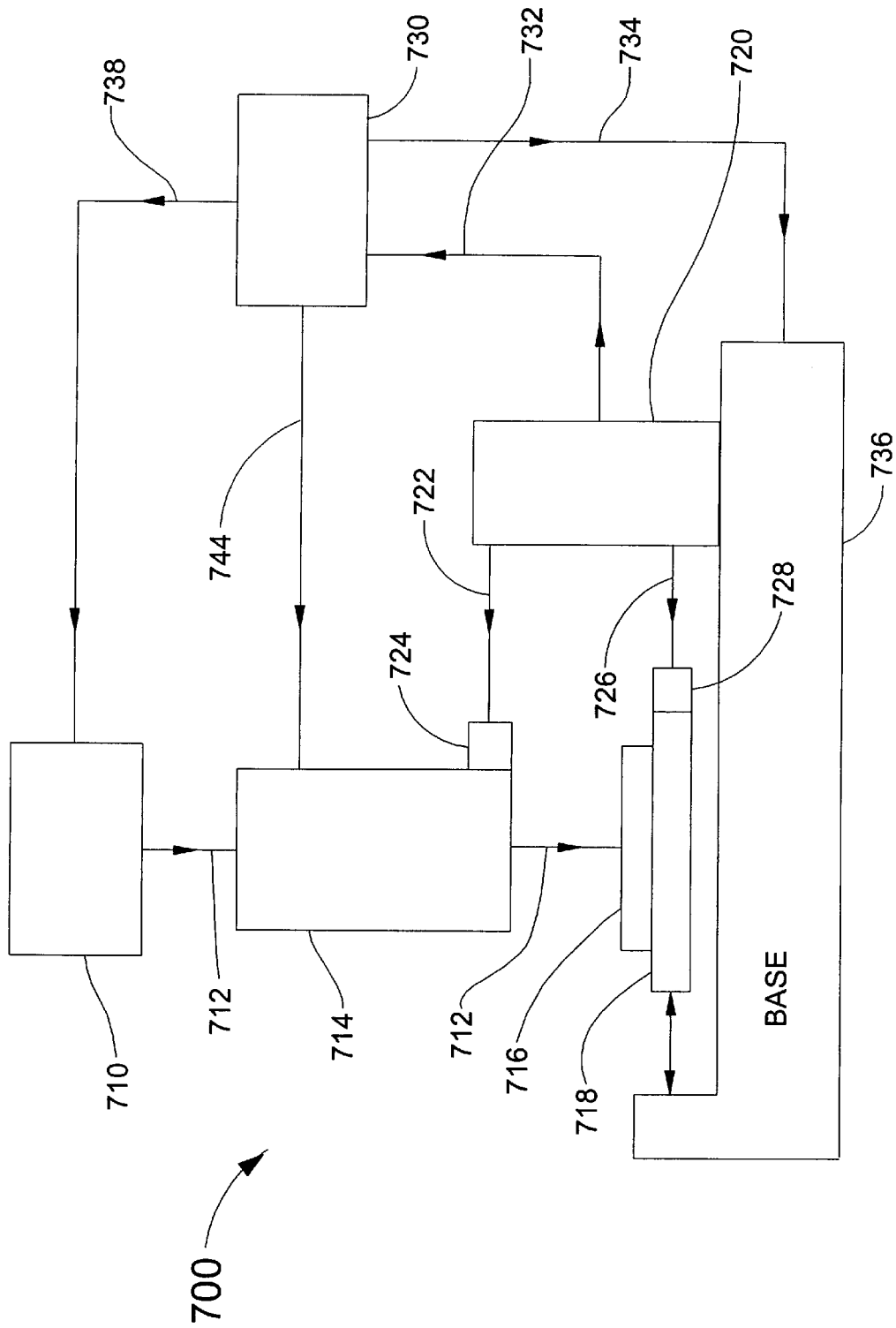
FIG. 6 is a schematic of a beam writing system employing the interferometry system.

As an example, a schematic of a beam writing system 700 is shown in FIG. 6. A source 710 generates a write beam 712, and a beam focusing assembly 714 directs the radiation beam to a substrate 716 supported by a movable stage 718. To determine the relative position of the stage, an interferometry system 720 directs a reference beam 722 to a mirror 724 mounted on beam focusing assembly 714 and a measurement beam 726 to a mirror 728 mounted on stage 718. Interferometry system 720 can be any of the interferometry systems described previously. Changes in the position measured by the interferometry system correspond to changes in the relative position of write beam 712 on substrate 716. Interferometry system 720 sends a measurement signal 732 to controller 730 that is indicative of the relative position of write beam 712 on substrate 716. Controller 730 sends an output signal 734 to a base 736 that supports and positions stage 718. In addition, controller 730 sends a signal 738 to source 710 to vary the intensity of, or block, write beam 712 so that the write beam contacts the substrate with an intensity sufficient to cause photophysical or photochemical change only at selected positions of the substrate. Furthermore, in some embodiments, controller 730 can cause beam focusing assembly 714 to scan the write beam over a region of the substrate, e.g., using signal 744. As a result, controller 730 directs the other components of the system to pattern the substrate. The patterning is typically based on an electronic design pattern stored in the controller. In some applications the write beam patterns a photoresist coated on the substrate and in other applications the write beam directly patterns, e.g., etches, the substrate.

An important application of such a system is the fabrication of masks and reticles used in the lithography methods described previously. For example, to fabricate a lithography mask an electron beam can be used to pattern a chromium-coated glass substrate. In such cases where the write beam is an electron beam, the beam writing system encloses the electron beam path in a vacuum. Also, in cases where the write beam is, e.g., an electron or ion beam, the beam focusing assembly includes electric field generators such as quadrapole lenses for focusing and directing the charged particles onto the substrate under vacuum. In other cases where the write beam is a radiation beam, e.g., x-ray, UV, or visible radiation, the beam focusing assembly includes corresponding optics for focusing and directing the radiation to the substrate.

Yet other changes may be made to the invention. For example, it may be desirable in certain applications to monitor the refractive index of the gas contained on both the reference and in the measurement legs of the interferometer. Examples include the well-known column reference style of interferometer, in which the reference leg comprises a target optic placed at one position within a mechanical system, and the measurement leg comprises a target optic placed at a different position within the same mechanical system. Another example application relates to the measurement of small angles, for which both the measurement and reference beams impinge upon the same target optic but at a small physical offset, thereby providing a sensitive measure of the angular orientation of the target optic. These applications and configurations are well known to those skilled in the art and the necessary modifications are intended to be within the scope of the invention.

Additional alternative means of achieving substantial insensitivity to Doppler shifting in a heterodyne interferometer is to track the Doppler shift and compensate by either (1) adjusting the frequency difference between the reference and measurement beams, (2) adjusting the clock frequency of one or both of the electronic A/D modules or (3) any similar means of continuously matching the apparent heterodyne beat frequency of the two wavelengths by active adjustment of the drive or detection electronics. Further examples of displacement measurement interferometers that may be used in the inventive apparatus and employ second harmonic generation (SHG) techniques include those described in U.S. Pat. Nos. 4,948,254 to Akira Ishida, 5,404,222 and 5,537,209 both to Steven A. Lis, 5,5,543,914 to Philip Henshaw, 5,757,489 to Jun Kawakami, and 5,748,315 and 5,767,971 both to Hitohsi Kawai, et al., all of which are incorporated herein by reference. For further examples of displacement interferometers that may be used in the inventive apparatus and which include means for compensating for Doppler shifts reference may be had to copending, commonly owned U.S. patent application Ser. Nos. 09/252,266 and 09/252,440, both of which were filed on Feb. 18, 1999 and are incorporated herein by reference.

It is understood that while the invention has been described in conjunction with the detailed description thereof, the foregoing description is intended to illustrate and not limit the scope of the invention, which is defined by the scope of the appended claims.

What is claimed is:

1. A gas insensitive interferometric apparatus for measuring physical displacement, said interferometric apparatus comprising:
   means for generating at least two light beams having different wavelengths;
   an interferometer having at least one measurement leg arranged to have a variable physical displacement that is to be measured while occupied by a gas and adapted to receive said light beams and generate non-intrinsic measurement information that varies in accordance with the optical path length and the instantaneous column density of the gas in said measurement leg;
   monitor means for determining the intrinsic optical properties of the gas in said measurement leg and generating a monitor signal indicative of said intrinsic optical properties; and
   electronic means for receiving said non-intrinsic measurement information and said monitor signal and determining the actual physical displacement in said measurement leg by substantially compensating for the presence of the gas in said measurement leg in accordance with both said non-intrinsic information and said intrinsic optical properties of the gas.

2. The interferometric apparatus of claim 1 wherein said interferometer comprises an amplitude splitting interferometer.

3. The interferometric apparatus of claim 2 wherein said amplitude splitting interferometer further comprises:
   a reference leg;
   means for dividing said light beams and directing at least a portion of both for travel along both said reference and said measurement legs to generate exit light beams containing information about the respective optical path lengths through said reference and measurement legs at said wavelengths;
   means for combining said exit light beams after having traveled along both said reference and measurement leg to generate mixed optical signals containing information corresponding to the phase differences between each of said exit beams that vary in accordance with the optical paths each experienced in traveling along said reference and said measurement legs at both of said wavelengths.

4. The interferometric apparatus of claim 3 further including means for detecting said mixed optical signals and generating electrical interference signals containing information corresponding to the effects of the index of refraction of the gas at said different beam wavelengths and the physical path length of said reference and measurement leg occupied by said gas.

5. The interferometric apparatus of claim 4 further including electronic means for analyzing said electrical interference signals to extract therefrom said non-intrinsic information and combine it with said intrinsic information to determine said displacement.

6. The interferometric apparatus of claim 2 wherein said amplitude splitting interferometer is selected from the group of interferometer forms including the Michelson, Mach-Zehnder, plane mirror, differential plane mirror, and angle compensating.

7. The interferometric apparatus of claim 1 further including means for doubling the frequency of one of said light beams at one of said wavelengths to generate the second of said light beams at the other of said wavelengths.

8. The interferometric apparatus of claim 1 further including means for doubling the frequency of at least one of said exit beams prior to combining said exit beams to produce said mixed optical signals.

9. The interferometric apparatus of claim 1 wherein said electronic means is configured to determine the intrinsic optical property, the reciprocal dispersive power, $\Gamma$, of the gas, as:

$$\Gamma = \frac{[n_1(\lambda_1) - 1]}{[n_3(\lambda_3) - n_2(\lambda_2)]}, \text{ and}$$

$\lambda_1$, $\lambda_2$, and $\lambda_3$ are wavelengths and $n_1$, $n_2$, and $n_3$ are indices of refraction and wherein the denominator may be replaced by $[n_3(\lambda_3)-n_1(\lambda_1)]$ or $[n_2(\lambda_2)-n_1(\lambda_1)]$.

10. The interferometric apparatus of claim 1 wherein said electronic means is configured to determine the refractivities of the gas corresponding to each light beam wavelength.

11. The interferometric apparatus of claim 1 wherein said electronic means is configured and arranged to calculate the intrinsic optical property, the reciprocal dispersive power, $\Gamma$, as:

$$\Gamma = \frac{[n_i(\lambda_i) - 1]}{[n_{j+1}(\lambda_{j+1}) - 1] - [n_j(\lambda_j) - 1]}, \text{ where}$$

i and j are integers corresponding to wavelengths.

12. The interferometric apparatus of claim 1 wherein said electronic means is configured to determine the intrinsic optical property, the relative refractivities at different beam wavelengths, where said relative refractivities are of the form:

$$\frac{n_{\lambda_i}-1}{n_{\lambda_j}-1}$$

where i and j are integers corresponding to wavelengths and are different from one another.

13. The interferometric apparatus of claim 1 wherein said electronic means further includes means for compensating for cyclic errors present in said non-intrinsic information corresponding to the dispersion of the gas, $(n_{\lambda_i}-n_{\lambda_j})$, in said measurement leg, where i and j are integers corresponding to wavelengths and different from one another.

14. The interferometric apparatus of claim 1 wherein said electronic means further includes means for compensating for cyclic errors present in at least one of said electrical interference signals.

15. The interferometric apparatus of claim 1 wherein said electronic means further includes means for compensating for cyclic errors in present in said non-intrinsic information corresponding to the dispersion of the gas, $(n_{\lambda_i}-n_{\lambda_j})$, in said measurement leg, where i and j are integers corresponding to wavelengths and different from one another and in at least one of said electrical interference signals.

16. The interferometric apparatus of claim 15 further including means for measuring the accuracy of said wavelengths and generating a wavelength accuracy signal indicative thereof.

17. The interferometric apparatus of claim 16 wherein said electronic means further includes means for receiving said wavelength accuracy signal and using its value in the determination of said actual physical displacement.

18. The interferometric apparatus of claim 16 further including wavelength correction means for receiving said wavelength accuracy signal and generating a control signal to adjust said means for generating said light beams so that said wavelengths thereof are within predetermined limits of accuracy.

19. The interferometric apparatus of claim 1 wherein said interferometer further comprises:

a reference leg and a beam steering assembly having a beam steering element and a positioning system to orient said beam steering element, said beam steering element being arranged to direct at least one of a reference and measurement beam associated, respectively, with said reference and measurement legs, and in contact with said beam steering element, and a control circuit which, during operation, causes said positioning system to reorient said beam steering element in response to changes in at least one of angular orientation and position of a measurement object.

20. The interferometric apparatus of claim 1 wherein said wavelengths of said light beams have an approximate harmonic relationship to each other, said approximate harmonic relationship being expressed as a sequence of ratios, each ratio being comprised of a ratio of low order non-zero integers.

21. The interferometric apparatus of claim 20 wherein said interferometer comprises means for generating multiple passes along at least said measurement leg for said light beams where the number of passes for said light beams are harmonically related in a relationship which is substantially the same as said substantially harmonic relationship between said wavelengths.

22. The interferometric apparatus of claim 21 wherein said means for generating at least two light beams further includes means for generating orthogonally polarized components for each of said light beams.

23. The interferometric apparatus of claim 22 further including means for separating said light beams into pairs of orthogonally polarized components of common wavelength.

24. The interferometric apparatus of claim 23 further including means for spatially separating said orthogonally polarized pairs of components for subsequent downstream use in said interferometer means.

25. The interferometric apparatus of claim 20 wherein the relative precision of relationship of said wavelengths, expressed as said sequence of ratios, is an order of magnitude or more less than the dispersion of the refractive index of said gas, $(n_2-n_1)$ where $n_1$ and $n_2$ are, respectively, the indices of refraction of said gas at said different wavelengths, times the relative precision, $\epsilon$, desired for the measurement of the refractivity $(n_1-1)$ of the gas or of the change in the difference in optical path lengths of said measurement legs due to the gas.

26. The interferometric apparatus of claim 25 further including means for monitoring said relative precision of said approximate harmonic relationship expressed as said sequence of ratios.

27. The interferometric apparatus of claim 25 further including means responsive to said means for monitoring said relative precision of said approximate harmonic relationship for providing a feedback signal to control said means for generating said light beams so that said relative precision of said approximate harmonic relationship is of an order of magnitude or more less than the dispersion of the refractive index of said gas times the relative precision $\epsilon$ desired for the measurement of the refractivity $(n_1-1)$ of the gas or of the change in the difference in optical path lengths of said measurement legs due to the gas.

28. The interferometric apparatus of claim 4 further including means for introducing a frequency difference between at least a first and second portion of each of said light beams to generate a set of frequency shifted light beams such that no two beams of said set of frequency shifted light beams have the same frequency.

29. The interferometric apparatus of claim 28 wherein said electrical interference signals comprise heterodyne electrical signals.

30. The interferometric apparatus of claim 4 wherein said electronic means further includes means for receiving said electrical interference signals and directly extracting therefrom phase information corresponding to the select intrinsic optical properties of the gas.

31. The interferometric apparatus of claim 1 wherein said different wavelengths have an approximate harmonic relationship to each other, said approximate harmonic relationship being expressed as a sequence of ratios, each ratio being comprised of a ratio of low order, non-zero integers.

32. The interferometric apparatus of claim 31 wherein said electronic means further includes phase analyzing means for receiving said electrical interference signals and generating initial electrical phase signals containing information corresponding to the effects of the index of refraction of the gas at said different beam wavelengths and the physical path lengths of said measurement legs occupied by said gas and their rates of change.

33. The interferometric apparatus of claim 32 wherein said electronic means further includes multiplying means for multiplying said initial phase signals by factors proportional to said wavelengths to generate modified phase signals.

34. The interferometric apparatus of claim 1 wherein said interferometer has a reference leg that is structured and arranged with said measurement leg so that beams at one of said wavelengths of said light beams travel through at least one of said reference and second measurement legs along predetermined optical paths a different number of passes than beams at the other of said wavelengths to compensate for the relative rates at which the physical path lengths of said reference and second measurement legs are changing.

35. The interferometric apparatus of claim 1 wherein said wavelengths of said light beams have an approximate harmonic relationship to each other, said approximate harmonic relationship being expressed as a sequence of ratios, each ratio being comprised of a ratio of low order non-zero integers.

36. The interferometric apparatus of claim 35 wherein said interferometer comprises means for generating multiple passes along at least one said measurement leg for said light beams where the number of passes for said light beams are harmonically related in a relationship which is substantially the same as said substantially harmonic relationship between said wavelengths.

37. The interferometric apparatus of claim 1 further including a microlithographic means operatively associated with said interferometric apparatus for fabricating integrated circuits on wafers, said microlithographic means comprising:

at least one stage;
an illumination system for imaging spatially patterned radiation onto the wafer; and
at least one positioning system for adjusting the position of said at least one stage;
wherein said interferometric apparatus is adapted to measure the position of said at least one stage.

38. The interferometric apparatus of claim 1 further including a microlithographic means operatively associated with said interferometric apparatus for use in fabricating integrated circuits on a wafer, said microlithographic means comprising:

at least one stage for supporting a wafer;
an illumination system including a radiation source, a mask, a positioning system, a lens assembly, and predetermined portions of said interferometric apparatus,
said microlithographic means being operative such that the source directs radiation through said mask to produce spatially patterned radiation, said positioning system adjusts the position of said mask relative to radiation from said source, said lens assembly images said spatially patterned radiation onto the wafer, and said interferometric apparatus measures the position of said mask relative to said radiation from said source.

39. The interferometric apparatus of claim 1 further including a beam writing system operatively associated with said interferometric apparatus for use in fabricating a lithography mask, said beam writing system comprising:

a source for providing a write beam to pattern a substrate;
at least one stage for supporting a substrate;
a beam directing assembly for delivering said write beam to the substrate; and
a positioning system for positioning said at least one stage and said beam directing assembly relative to one another,
said interferometric apparatus being adapted to measure the position of said at least one stage relative to said beam directing assembly.

40. The interferometric apparatus of claim 1 monitor means for determining said intrinsic optical properties is located proximate said measurement leg of said interferometer.

41. The interferometric apparatus of claim 1 monitor means for determining said intrinsic optical properties is located proximate to and upstream of said reference leg of said interferometer so as to capture changes in the upstream composition and environmental conditions of the gas prior to the gas reaching said measurement leg.

42. The interferometric apparatus of 41 further including means for periodically sampling the values of said intrinsic optical properties to assess any changes in them and update the values of said intrinsic optical properties for use in subsequent calculations should the changes exceed predetermined values.

43. Interferometric apparatus for measuring distances occupied by a gas whose optical properties may vary over the measured distance, said system comprising:

interferometer means comprising first and second measurement legs, said first and second measurement legs having optical paths structured and arranged such that at least one of them has a variable physical length and at least one of them is at least in part occupied by the gas and one of them may at least in part be occupied by a predetermined medium, the optical path length difference between said first and second measurement legs varying in accordance with the difference between the respective physical lengths of their optical paths and the properties of said gas and said predetermined medium;
means for generating at least two light beams having different wavelengths;

means for introducing first and second predetermined portions of each of said light beams into said first and second measurement legs, respectively, of said interferometer means so that each of said first and second predetermined portions of said light beams travels through said first and second measurement legs along predetermined optical paths, said predetermined first and second portions of said light beams emerging from said interferometer means as exit beams containing information about the respective optical path lengths through said first and second measurement legs at said wavelengths;

means for combining said exit beams to produce mixed optical signals containing information corresponding to the phase differences between each of said exit beams from corresponding ones of said predetermined optical paths of said first and second measurement legs at said wavelengths;

means for detecting said mixed optical signals and generating electrical interference signals containing information corresponding to the effects of the index of refraction of the gas at said different beam wavelengths and the physical path length of said first and second measurement legs occupied by said gas;

means for measuring intrinsic optical properties of the gas and generating corrective information for compensating for the variable optical properties of the gas in said first and second measurement legs; and electronic means for determining difference in physical length between said first and second reference legs based on the information contained in said interference signals and said corrective information.

44. The interferometric apparatus of claim 43 wherein said interferometer means is selected from the forms comprising the Michelson, the Mach-Zehnder, the plane mirror, the differential plane mirror, and the angle compensating.

45. The interferometric apparatus of claim 43 wherein said interferometer means, said beam wavelengths, and said electronic means are configured and arranged with respect to one another to compensate for Doppler shifts introduced by stage motion.

46. The interferometric apparatus of claim 43 further including means for compensating for cyclic errors in at least one of said electrical interference signals and the dispersion of the gas.

47. The interferometric apparatus of claim 43 wherein said means for measuring intrinsic optical properties comprises and interferometer selected from the forms comprising the Michelson, the Mach-Zehnder, the plane mirror, the differential plane mirror, and the angle compensating.

48. The interferometric apparatus of claim 43 wherein said means for measuring intrinsic optical properties uses portions of the same beams as are used by said interferometer means.

49. The interferometric apparatus of claim 43 further including photolithographic apparatus.

50. A gas insensitive interferometric apparatus for measuring physical length, said interferometric apparatus comprising:

an interferometer having a measurement leg of variable physical length that is to be measured while occupied by a gas, said interferometer being adapted to generate at least one signal indicative of the optical path length of said measurement leg and at least one other signal indicative of the non-intrinsic optical properties of the gas in said measurement leg;

a monitor for measuring the intrinsic optical properties of the gas and generating a corrective signal indicative of said intrinsic optical properties; and means for receiving said at least one signal and said at least one other signal and determining the actual physical length of said measurement leg by substantially compensating for the presence of the gas in said measurement leg.

51. A gas insensitive interferometric apparatus for measuring variable physical length in a gas, said interferometer comprising:

first interferometer means comprising a reference leg and a measurement leg whose physical length is variable and is occupied by the gas;

second interferometer means for use in the compensation of the presence of the gas in said first interferometer means, said second interferometer means comprising a reference leg and a measurement leg each of which has a predetermined physical path length, said reference leg being configured and arranged to be occupied by a predetermined medium and said measurement leg being configured and arranged to be occupied by the gas;

means for generating at least two light beams having different wavelengths;

means for introducing at least a portion of each of predetermined ones of said light beams into preselected ones of said reference and measurement legs of said first and second interferometers to generate optical signals that contain information corresponding to:
(a) the optical path length in the measurement path of said first interferometer means at a first one of said wavelengths,
(b) the optical path length in the measurement leg of said first interferometer means at at least one other one of said wavelengths, and
(c) intrinsic optical properties of the gas in said measurement leg of said second interferometer means at first and said at least one other one of said wavelengths;

means for converting said optical signals to electrical signals; and electronic means for processing said electrical signals to compensate for the presence of the gas in the measurement leg of said first interferometer and determine the physical path length of said measurement leg of said first interferometer means by substantially correcting for the presence of the gas in said measurement leg of said first interferometer means.

52. A gas insensitive interferometric apparatus comprising:

an interferometer having reference and measurement legs where said measurement leg is configured so that the physical path length, L, thereof can vary and is occupied by the gas;

an interferometric $\Gamma$-monitor;

means for generating at least two light beams having different wavelengths;

means for introducing at least a portion of predetermined ones of each of said light beams into said interferometer and said interferometric $\Gamma$-monitor and generating:
(a) a first signal for said physical path length, L, where $L=L_1-\Gamma(L_2-L_1)$, $L_1$ is the optical path length of said measurement leg divided by $p_1 k_1$ where $k_1$ is the wavenumber and $p_1$ the number of passes through said measurement leg at $\lambda_1$, $L_2$ is the optical path length of said measurement leg divided by $p_2 k_2$ where $k_2$ is the wavenumber and $p_2$ the number of passes through said measurement leg at wavelength $\lambda_2$, and $\Gamma=(n_1-1)/(n_2-n_1)$ where $n_1$ and $n_2$ are, respectively, the indices of refraction of the gas in said measurement leg at $\lambda_1$ and $\lambda_2$, and (b) a second signal containing information for calculating $\Gamma$ to correct said first signal for errors in said first signal related to the presence of the gas in said measurement leg at $\lambda_1$; and signal processing means for receiving said first and second signals and calculating $\Gamma$ and then said actual physical length, L, of said measurement leg.

53. A gas insensitive interferometric method for measuring physical displacement, said interferometric method comprising the steps of:

generating at least two light beams having different wavelengths;

providing an interferometer having at least one measurement leg arranged to have a variable physical displacement that is to be measured while occupied by a gas and adapted to receive said light beams and generate non-intrinsic measurement information that varies in accordance with the optical path length and the instantaneous column density of the gas in said measurement leg;

determining the intrinsic optical properties of the gas in said measurement leg and generating a monitor signal indicative of said intrinsic optical properties; and receiving said non-intrinsic measurement information and said monitor signal and determining the actual physical displacement in said measurement leg by substantially compensating for the presence of the gas in said measurement leg in accordance with both said non-intrinsic information and said intrinsic optical properties of the gas.

54. The interferometric method of claim 53 wherein said interferometer comprises an amplitude splitting interferometer.

55. The interferometric method of claim 54 wherein said amplitude splitting interferometer further comprises:

a reference leg;

means for dividing said light beams and directing at least a portion of both for travel along both said reference and said measurement legs to generate exit light beams containing information about the respective optical path lengths through said reference and measurement legs at said wavelengths;

means for combining said exit light beams after having traveled along both said reference and measurement leg to generate mixed optical signals containing information corresponding to the phase differences between each of said exit beams that vary in accordance with the optical paths each experienced in traveling along said reference and said measurement legs at both of said wavelengths.

56. The interferometric method of claim 55 further including the step of detecting said mixed optical signals and generating electrical interference signals containing information corresponding to the effects of the index of refraction of the gas at said different beam wavelengths and the physical path length of said reference and measurement leg occupied by said gas.

57. The interferometric method of claim 56 further including the step of analyzing said electrical interference signals to extract therefrom said non-intrinsic information and combine it with said intrinsic information to determine said displacement.

58. The interferometric method of claim 54 wherein said amplitude splitting interferometer is selected from the group of interferometer forms including the Michelson, Mach-Zehnder, plane mirror, differential plane mirror, and angle compensating.

59. The interferometric method of claim 53 further including the step of doubling the frequency of one of said light beams at one of said wavelengths to generate the second of said light beams at the other of said wavelengths.

60. The interferometric method of claim 53 further including the step of doubling the frequency of at least one of said exit beams prior to combining said exit beams to produce said mixed optical signals.

61. The interferometric method of claim 53 determining the intrinsic optical property, the reciprocal dispersive power, $\Gamma$, of the gas, as:

$$\Gamma = \frac{[n_1(\lambda_1)-1]}{[n_3(\lambda_3)-n_2(\lambda_2)]}, \text{ and}$$

$\lambda_1$, $\lambda_2$, and $\lambda_3$ are wavelengths and $n_1$, $n_2$, and $n_3$ are indices of refraction and wherein the denominator may be replaced by $[n_3(\lambda_3)-n_1(\lambda_1)]$ or $[n_2(\lambda_2)-n_1(\lambda_1)]$.

62. The interferometric method of claim 53 wherein said determining the refractivities of the gas corresponding to each light beam wavelength.

63. The interferometric method of claim 53 including the step of calculating the intrinsic optical property, the reciprocal dispersive power, $\Gamma$, as:

$$\Gamma = \frac{[n_i(\lambda_i)-1]}{[n_{j+1}(\lambda_{j+1})-1]-[n_j(\lambda_j)-1]}, \text{ where}$$

i and j are integers corresponding to wavelengths.

64. The interferometric method of claim 53 determining the intrinsic optical property, the relative refractivities at different beam wavelengths, where said relative refractivities are of the form:

$$\frac{n_{\lambda_i}-1}{n_{\lambda_j}-1}$$

where i and j are integers corresponding to wavelengths and are different from one another.

65. The interferometric method of claim 53 further includes the step of compensating for cyclic errors present in said non-intrinsic information corresponding to the dispersion of the gas, $(n_{\lambda_j}-n_{\lambda_i})$, in said measurement leg, where i and j are integers corresponding to wavelengths and different from one another.

66. The interferometric method of claim 53 further including the step of compensating for cyclic errors present in at least one of said electrical interference signals.

67. The interferometric method of claim 53 further including the step of compensating for cyclic errors in present in said non-intrinsic information corresponding to the dispersion of the gas, $(n_{\lambda_j}-n_{\lambda_i})$, in said measurement leg, where i and j are integers corresponding to wavelengths and different from one another and in at least one of said electrical interference signals.

68. The interferometric method of claim 67 further the step of measuring the accuracy of said wavelengths and generating a wavelength accuracy signal indicative thereof.

69. The interferometric method of claim 68 further including the step of receiving said wavelength accuracy signal and using its value in the determination of said actual physical displacement.

70. The interferometric method of claim 68 further including the step of receiving said wavelength accuracy signal and generating a control signal to adjust said means for generating said light beams so that said wavelengths thereof are within predetermined limits of accuracy.

71. The interferometric method of claim 53 wherein said interferometer further comprises:
  a reference leg and a beam steering assembly having a beam steering element and a positioning system to orient said beam steering element, said beam steering element being arranged to direct at least one of a reference and measurement beam associated, respectively, with said reference and measurement legs, and in contact with said beam steering element, and
  a control circuit which, during operation, causes said positioning system to reorient said beam steering element in response to changes in at least one of angular orientation and position of a measurement object.

72. The interferometric method of claim 53 wherein said wavelengths of said light beams have an approximate harmonic relationship to each other, said approximate harmonic relationship being expressed as a sequence of ratios, each ratio being comprised of a ratio of low order non-zero integers.

73. The interferometric method of claim 72 further including the step of generating multiple passes along at least said measurement leg for said light beams where the number of passes for said light beams are harmonically related in a relationship which is substantially the same as said substantially harmonic relationship between said wavelengths.

74. The interferometric method of claim 73 including the step of generating at least two light beams further includes the step of generating orthogonally polarized components for each of said light beams.

75. The interferometric method of claim 74 further including the step of separating said light beams into pairs of orthogonally polarized components of common wavelength.

76. The interferometric method of claim 75 further includes spatially separating said orthogonally polarized pairs of components for subsequent downstream use in said interferometer means.

77. The interferometric method of claim 72 wherein the relative precision of relationship of said wavelengths, expressed as said sequence of ratios, is an order of magnitude or more less than the dispersion of the refractive index of said gas, $(n_2-n_1)$ where $n_1$ and $n_2$ are, respectively, the indices of refraction of said gas at said different wavelengths, times the relative precision, $\epsilon$, desired for the measurement of the refractivity $(n_1-1)$ of the gas or of the change in the difference in optical path lengths of said measurement legs due to the gas.

78. The interferometric method of claim 77 further including monitoring said relative precision of said approximate harmonic relationship expressed as said sequence of ratios.

79. The interferometric method of claim 78 further the step of, responsive to monitoring said relative precision of said approximate harmonic relationship, providing a feedback signal to control said light beams so that said relative precision of said approximate harmonic relationship is of an order of magnitude or more less than the dispersion of the refractive index of said gas times the relative precision $\epsilon$ desired for the measurement of the refractivity $(n_1-1)$ of the gas or of the change in the difference in optical path lengths of said measurement legs due to the gas.

80. The interferometric method of claim 56 further including the step of introducing a frequency difference between at least a first and second portion of each of said light beams to generate a set of frequency shifted light beams such that no two beams of said set of frequency shifted light beams have the same frequency.

81. The interferometric method of claim 80 wherein said electrical interference signals comprise heterodyne electrical signals.

82. The interferometric method of claim 56 wherein said further including receiving said electrical interference signals and directly extracting therefrom phase information corresponding to the select intrinsic optical properties of the gas.

83. The interferometric method of claim 53 wherein said different wavelengths have an approximate harmonic relationship to each other, said approximate harmonic relationship being expressed as a sequence of ratios, each ratio being comprised of a ratio of low order, non-zero integers.

84. The interferometric apparatus of claim 83 further including the step of receiving and analyzing the phase of said electrical interference signals and generating initial electrical phase signals containing information corresponding to the effects of the index of refraction of the gas at said different beam wavelengths and the physical path lengths of said measurement legs occupied by said gas and their rates of change.

85. The interferometric method of claim 84 further including the step of multiplying said initial phase signals by factors proportional to said wavelengths to generate modified phase signals.

86. The interferometric method of claim 53 wherein said interferometer has a reference leg that is structured and arranged with said measurement leg so that beams at one of said wavelengths of said light beams travel through at least one of said reference and second measurement legs along predetermined optical paths a different number of passes than beams at the other of said wavelengths to compensate for the relative rates at which the physical path lengths of said reference and second measurement legs are changing.

87. The interferometric method of claim 53 wherein said wavelengths of said light beams have an approximate harmonic relationship to each other, said approximate harmonic relationship being expressed as a sequence of ratios, each ratio being comprised of a ratio of low order non-zero integers.

88. The interferometric method of claim 87 including the step of generating multiple passes along at least one said measurement leg for said light beams where the number of passes for said light beams are harmonically related in a relationship which is substantially the same as said substantially harmonic relationship between said wavelengths.

89. The interferometric method of claim 53 further including a microlithographic method operatively associated with said interferometric method for fabricating integrated circuits on wafers, said microlithographic method comprising the steps of:
  supporting a wafer on at least one stage;
  imaging spatially patterned radiation onto the wafer; and
  adjusting the position of said at least one stage;
  wherein said interferometric method is adapted to measure the position of said at least one stage.

90. The interferometric method of claim 53 further including a microlithographic method operatively associated with said interferometric apparatus for use in fabricating integrated circuits on a wafer, said microlithographic method comprising the steps of:
  supporting a wafer on at least one stage;
  providing an illumination system including a radiation source, a mask, a positioning system, a lens assembly, and predetermined portions of said interferometric apparatus, directing radiation through said mask to produce spatially patterned radiation, said positioning system adjusting the position of said mask relative to radiation from said source, said lens assembly imaging said spatially patterned radiation onto the wafer, and measuring the position of said mask relative to said radiation from said source.

91. The interferometric method of claim 53 further including a microlithographic method operatively associated with said interferometric apparatus for fabricating integrated circuits comprising first and second components, said first and second components being moveable relative to one another, said first and second components being connected with said first and second measurement legs, moving in concert therewith, such that said interferometric apparatus measures the position of said first component relative to said second component.

92. The interferometric method of claim 53 further including a beam writing method operatively associated with said interferometric method for use in fabricating a lithography mask, said beam writing method comprising the steps of:

provising a write beam to pattern a substrate;

supporting a substrate on at least one stage;

directing a beam to the substrate; and positioning said at least one stage and said beam relative to one another, said interferometric method being adapted to measure the position of said at least one stage relative to said beam.

93. The interferometric method of claim 53 wherein said intrinsic optical properties are determined proximate said measurement leg of said interferometer.

94. The interferometric method of claim 53 said intrinsic optical properties are monitored proximate to and upstream of said reference leg of said interferometer so as to capture changes in the upstream composition and environmental conditions of the gas prior to the gas reaching said measurement leg.

95. The interferometric method of claim 93 further including the step of periodically sampling the values of said intrinsic optical properties to assess any changes in them and update the values of said intrinsic optical properties for use in subsequent calculations should the changes exceed predetermined values.

96. The interferometric method of claim 53 further including the step of resolving phase redundancies in said electrical interference signals.

97. The interferometric apparatus of claim 1 further including microlithographic apparatus operatively associated with said interferometric apparatus for fabricating integrated circuits comprising first and second components, said first and second components being moveable relative to one another, said first and second components being connected with said first and second measurement legs, moving in concert therewith, such that said interferometric apparatus measures the position of said first component relative to said second component.

* * * * *